United States Patent
Vieira et al.

(10) Patent No.: US 6,319,493 B1
(45) Date of Patent: *Nov. 20, 2001

(54) TREATMENT OF NEOPLASTIC DISEASE WITH INTERLEUKIN-10

(75) Inventors: Paulo J. Vieira, Linda-a-velha (PT); Kevin W. Moore, Palo Alto, CA (US); Rene de Waal Malefyt, Sunnyvale, CA (US); Jan E. de Vries, Los Altos, CA (US); Anne-Catherine Fluckiger, Los Angeles, CA (US); Jacques Banchereau, Ecully (FR)

(73) Assignee: Schering Corporation, Kenilworth, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/552,613

(22) Filed: Apr. 19, 2000

Related U.S. Application Data

(63) Continuation of application No. 08/170,113, filed on Dec. 17, 1993, now Pat. No. 6,106,823, which is a continuation of application No. 07/933,419, filed on Aug. 21, 1992, now abandoned, which is a continuation of application No. 08/091,333, filed on Jul. 12, 1993, now abandoned, which is a continuation-in-part of application No. 08/020,018, filed on Feb. 17, 1993, now abandoned, which is a continuation of application No. 07/830,496, filed on Feb. 4, 1992, now abandoned, which is a continuation of application No. 07/641,347, filed on Jan. 16, 1991, now abandoned.

(51) Int. Cl.$^7$ .......................... A61K 38/19; A61K 38/20

(52) U.S. Cl. .................. 424/85.2; 514/2; 514/8; 514/12; 514/885

(58) Field of Search .................. 424/85.2, 85.1; 514/2, 8, 121, 885; 530/351

(56) References Cited

U.S. PATENT DOCUMENTS 6,106,823 * 8/2000 Vieira et al. .......................... 424/85.2

FOREIGN PATENT DOCUMENTS

| 0 405 980 | 1/1991 | (EP) . |
| WO 91/09127 | 6/1991 | (WO) . |
| WO 92/12725 | 6/1992 | (WO) . |

OTHER PUBLICATIONS

Azuma, et al., "CD28 interaction with B7 costimulates primary allogeneic proliferative responses and cytotoxicity mediated by small, resting T lymphocytes", *J Exp Med*, 175:353–359 (1992).

Chen and Zlotnik., "IL–10: a novel cytotoxic T cell differentiation factor", *J Immunol*, 147:528–534 (1991).

de Waal Malefyt, et al., "Interleukin 10 (IL–10) and viral IL–10 strongly reduce antigen–specific human T cell proliferation by diminishing the antigen–presenting capacity of monocytes via downregulation of class II major histocompatibility complex expression", *J Exp Med*, 174:915–924 (1991).

de Waal Malefyt, et al., "Interleukin 10 (IL–10) inhibits cytokine synthesis by human monocytes: an autoregulatory role of IL–10 produced by monocytes", *J Exp Med*, 174:1209–1220 (1991).

de Waal Malefyt, et al., "Interleukin–10", *Curr Opin Immunol*, 4:314–320 (1992).

de Waal Malefyt, et al., "IL–10 directly inhibits IL–2 transcription by human PBL T cells, ThO, Th1 and Th2 clones" *Abstract for the International Congress of Immunology in Budapest, Hungary*, 1992.

Defrance, et al., "Interleukin 10 and transforming growth factor beta cooperate to induce anti–CD40–activated naive human B cells to secrete immunoglobulin A", *J Exp Med*, 175:671–682 (1992).

Dighiero, et al., "B–cell chronic lymphocytic leukemia: present status and future directions. French Cooperative Group on CLL", *Blood*, 78:1901–1914 (1991).

Fiorentino, et al., "IL–10 acts on the antigen–presenting cell to inhibit cytokine production by Th1 cells", *J Immunol*, 146:3444–3452 (1991).

Go, et al., "Interleukin 10, a novel B cell stimulatory factor: unresponsiveness of X chromosome–linked immunodeficiency B cells", *J Exp Med*, 172:1625–1631 (1990).

Hsu et al., "Expression of interleukin–10 activity by Epstein–Barr virus protein BCRF1", *Science*, 250:830–832 (1990).

MacNeil, et al., "IL–10, a novel growth cofactor for mature and immature T cells", *J Immunol*, 145:4167–4173 (1990).

O'Garra, et al., "Production of cytokines by mouse B cells: B lymphomas and normal B cells produce interleukin 10", *Int Immunol*, 2:821–832 (1990).

Richter, et al., "Interleukin 10 transfected into Chinese hamster ovary cells prevents tumor growth and macrophage infiltration", *Cancer Res*, 53:4134–4137 (1993).

Rousset, et al., "Interleukin 10 is a potent growth and differentiation factor for activated human B lymphocytes", *Proc Natl Acad Sci USA*, 89:1890–1893 (1992).

Salmon, *Cecil Textbook of Medicine*, 19$^{th}$ ed., Wyngaarden et al. (eds.), W.B. Saunder & Co., Philadelphia, PA, pp. 1049–1067 (1992).

Shaw, et al., "Two antigen–independent adhesion pathways used by human cytotoxic T–cell clones", *Nature*, 323:262–264 (1986).

(List continued on next page.)

*Primary Examiner*—Prema Mertz
(74) *Attorney, Agent, or Firm*—David B. Schram; Immac J. Thampoe; Cynthis L. Foulke

(57) ABSTRACT

A method is provided for treating tumors, e.g., lymphocytic leukemias, which comprises administering to a mammal an effective amount of interleukin-10.

14 Claims, 18 Drawing Sheets

OTHER PUBLICATIONS

Spits, et al., "Alloantigen recognition is preceded by non-specific adhesion of cytotoxic T cells and target cells", *Science*, 232:403–405 (1986).

Tepper, et al., "Murine interleukin–4 displays potent antitumor activity in vivo", *Cell*, 57:503–512 (1989).

Thompson–Snipes, et al., "Interleukin 10: a novel stimulatory factor for mast cells and their progenitors", *J Exp Med*, 173:507–510 (1991).

Whicher, et al., "Cytokines in disease", *Clin Chem*, 36:1269–1281 (1990).

Fiorentino, et al., *J. Immunol.*, 1991, 146(10):3444–3452.

Thompson–Snipes, et al., *J. Exp. Med.*, 1991, 173(2):507–510.

MacNeil, et al., *J. Immunol.*, 1990, 145(12):4167–4173.

O'Garra, et al., *Int. Immunol.*, 1990, 2(9):821–832.

Chen, et al., *J. Immunol.*, 1991, 147(2):528–534.

de Waal Malefyt, et al., *J. Exp. Med.*, 1991, 174(4):915–924.

Spits, et al., *Science*, 1986, 232(4748):403–405.

Shaw, et al., *Nature*, 1986, 323(6085):262–264.

Azuma, et al., *J. Exp. Med.*, 1992, 175(2):353–359.

de Waal Malefyt, et al., *Curr. Opin. Immunol.*, 1992, 4(3):314–320.

de Waal Malefyt, et al., *J. Exp. Med.*, 1991, 174(5):1209–1220.

de Waal Malefyt, et al., *Abstract for the International Congress of Immunology in Budapest, Hungary*, 1992.

Defrance, et al., *J. Exp. Med.*, 1992, 175(3):671–682.

Dighiero, et al., *Blood*, 1991, 78(8):1901–1914.

Go, et al., *J. Exp. Med.*, 1990, 172(6):1625–1631.

Hsu, et al., *Science*, 1990, 250(4982):830–832.

Rousset, et al., *Proc. Natl. Acad. Sci. USA*, 1992, 89(5):1890–1893.

Tepper, et al., *Cell*, 1989, 57(3):503–512.

Whicher, et al., *Clin. Chem.*, 1990, 36(7):1269–1281.

\* cited by examiner

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 178 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

```
Met His Ser Ser Ala Leu Leu Cys Cys Leu Val Leu Leu Thr Gly Val
 1               5                  10                  15

Arg Ala Ser Pro Gly Gln Gly Thr Gln Ser Glu Asn Ser Cys Thr His
                20                  25                  30

Phe Pro Gly Asn Leu Pro Asn Met Leu Arg Asp Leu Arg Asp Ala Phe
            35                  40                  45
```

```
Ser Arg Val Lys Thr Phe Phe Gln Met Lys Asp Gln Leu Asp Asn Leu
     50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
                100                 105                 110

Gly Glu Asn Leu Lys Thr Leu Arg Leu Arg Leu Arg Arg Cys His Arg
                115                 120                 125

Phe Leu Pro Cys Glu Asn Lys Ser Lys Ala Val Glu Gln Val Lys Asn
                130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn (2) INFORMATION FOR SEQ ID NO:2:

(i) SEQUENCE CHARACTERISTICS:
        (A) LENGTH: 170 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Met Glu Arg Arg Leu Val Val Thr Leu Gln Cys Leu Val Leu Leu Tyr
1               5                   10                  15

Leu Ala Pro Glu Cys Gly Gly Thr Asp Gln Cys Asp Asn Phe Pro Gln
                20                  25                  30

Met Leu Arg Asp Leu Arg Asp Ala Phe Ser Arg Val Lys Thr Phe Phe
            35                  40                  45

Gln Thr Lys Asp Glu Val Asp Asn Leu Leu Leu Lys Glu Ser Leu Leu
    50                  55                  60

Glu Asp Phe Lys Gly Tyr Leu Gly Cys Gln Ala Leu Ser Glu Met Ile
65                  70                  75                  80

Gln Phe Tyr Leu Glu Glu Val Met Pro Gln Ala Glu Asn Gln Asp Pro
                85                  90                  95

Glu Ala Lys Asp His Val Asn Ser Leu Gly Glu Asn Leu Lys Thr Leu
                100                 105                 110

Arg Leu Arg Leu Arg Arg Cys His Arg Phe Leu Pro Cys Glu Asn Lys
                115                 120                 125

Ser Lys Ala Val Glu Gln Ile Leu Asn Ala Phe Asn Lys Leu Gln Glu
                130                 135                 140

Lys Gly Ile Tyr Lys Ala Met Ser Glu Phe Asp Ile Phe Ile Asn Tyr
145                 150                 155                 160

Ile Glu Ala Tyr Met Thr Ile Lys Ala Arg
                165                 170

(2) INFORMATION FOR SEQ ID NO:3:

(i) SEQUENCE CHARACTERISTICS:
        (A) LENGTH: 160 amino acids
        (B) TYPE: amino acid
        (C) STRANDEDNESS: single
```

(D) TOPOLOGY: linear (ii) MOLECULE TYPE: peptide (xi) SEQUENCE DESCRIPTION: SEQ ID NO:3:

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

(2) INFORMATION FOR SEQ ID NO:4:

(i) SEQUENCE CHARACTERISTICS:
            (A) LENGTH: 147 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:4:

Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Val Asp
            20                  25                  30

Asn Leu Leu Leu Lys Glu Ser Leu Leu Glu Asp Phe Lys Gly Tyr Leu
        35                  40                  45

Gly Cys Gln Ala Leu Ser Glu Met Ile Gln Phe Tyr Leu Glu Glu Val
50                  55                  60

Met Pro Gln Ala Glu Asn Gln Asp Pro Glu Ala Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
    130                 135                 140

Lys Ala Arg
145

(2) INFORMATION FOR SEQ ID NO:5:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
AGCCCAGGCC AGGGCACCCA GTCTGAGAAC AGCTGCACCC ACTTCCCAGG TAACCGGTAC      60
```

(2) INFORMATION FOR SEQ ID NO:6:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
GTAACCTGCC TAACATGCTT CGAGATCTCC GAGATGCCTT CAGCAGAGTG AAGACTTTCT      60
TT                                                                    62
```

(2) INFORMATION FOR SEQ ID NO:7:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
ACTTTCTTTC AAATGAAGGA TCAGCTGGAC AACTTGTTCT TAAG                       44
```

(2) INFORMATION FOR SEQ ID NO:8:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
GAGTCCTTGC TGGAGGACTT TAAGGGTTAC CTGGGTTGCC AAGCCTTGTC TGAGATGATC      60
CAGTTTTATC TAG                                                        73
```

(2) INFORMATION FOR SEQ ID NO:9:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
CTAGAGGAGG TGATGCCCCA AGCTGAGAAC CAAGACCCAG ACATCAAGGC GCATGTTAAC      60
```

(2) INFORMATION FOR SEQ ID NO:10:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
AACTCCCTGG GGGAGAACCT GAAGACCCTC AGGCTGAGGC TACGGCGCTG TCATCGATCT      60

GCA                                                                   63
```

(2) INFORMATION FOR SEQ ID NO:11:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

```
CGATTTCTTC CCTGTCAAAA CAAGAGCAAG GCCGTGGAGC AGGTGAAGAA CGCGTGCATG      60
```

(2) INFORMATION FOR SEQ ID NO:12:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

```
CGCGTTTAAT AATAAGCTCC AAGACAAAGG CATCTACAAA GCCATGAGTG AGTTTGAC        58
```

(2) INFORMATION FOR SEQ ID NO:13:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

```
GAGTTTGACA TCTTCATCAA CTACATAGAA GCCTACATGA CAATGAAGAT ACGAAACTGA      60

AGCT                                                                  64
```

(2) INFORMATION FOR SEQ ID NO:14:

(i) SEQUENCE CHARACTERISTICS:
        (A) LENGTH: 499 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

```
                                    -continued

AATTCATGGA GCGAAGGTTA GTGGTCACTC TGCAGTGCCT GGTGCTGCTT TACCTGGCAC      60

CTGAGTGTGG AGGTACAGAC CAATGTGACA ATTTTCCCCA GACCTAAGAG ATGCCTTCAG     120

TCGTGTTAAA ACCTTTTTCC AGACAAAGGA CGAGGTAGAT AACCTTTTGC TCAAGGAGTC     180

TCTGCTAGAG GACTTTAAGG ATGCCAGGCC CTGTCAGAAA TGATCCAATT CTACCTGGAG     240

GAAGTCATGC CACAGGCTGA AAACCAGGAC CCTGAAGCCA AAGACCATGT CAATTCTTTG     300

GGTGAAAATC TAAAGACCCT ACGGCTCCGC CTGCGCAGGT GCCACAGGTT CCTGCCGTGT     360

GAGAACAAGA GTAAAGCTGT GGAACAGATA AAAAATGCCT TTAACAAGCT GCAGGAAAAA     420

GGAATTTACA AAGCCATGAG TGAATTTGAC ATTTTTATTA ACTACATAGA AGCATACATG     480

ACAATTAAAG CCAGGTGAG                                                  499

(2) INFORMATION FOR SEQ ID NO:15:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

GAATTCCCAG GTTTAACGTA AGGAGGTTTA ACCATCGATG                            40

(2) INFORMATION FOR SEQ ID NO:16:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GGCTGCAGCG ACGAGCCATG GTTGCTGGGA GCGACGCG                              38

(2) INFORMATION FOR SEQ ID NO:17:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

TTCATCTTCT GGTACCAATC AATTGGAGTT GGTTC                                 35
```

US 6,319,493 B1

TREATMENT OF NEOPLASTIC DISEASE WITH INTERLEUKIN-10

This application is a continuation of commonly assigned U.S. patent application Ser. No. 08/170,113, filed Dec. 17, 1993, now U.S. Pat. No. 6,106,823 which is a continuation of commonly assigned U.S. patent application Ser. No. 07/933,419, filed Aug. 21, 1992, now abandoned and of commonly assigned U.S. patent application Ser. No. 08/091,333, filed Jul. 12, 1993, now abandoned which is a continuation-in-part of commonly assigned and U.S. patent application Ser. No. 08/020,018, filed Feb. 17, 1993, now abandoned which is a continuation of commonly assigned and U.S. patent application Ser. No. 07/830,496, filed Feb. 4, 1992, now abandoned which is a continuation of commonly assigned and then U.S. patent application Ser. No. 07/641,347, filed Jan. 16, 1991, now abandoned each of which is incorporated herein by reference.

FIELD OF THE INVENTION

The invention relates generally to methods and compositions for treating neoplasms, or cancers, in mammals. More particularly, it relates to the use of interleukin-10 (IL-10) compositions for treating various cancers, e.g., IL-2 dependent tumors, including B cell lymphocytic leukemia (B-CLL).

BACKGROUND OF THE INVENTION

Immunologic approaches to cancer therapy are based on the notion that cancer cells have somehow evaded the body's defenses against aberrant or foreign cells and molecules, and that these defenses might be therapeutically stimulated to regain the lost ground, see e.g., pp. 623–648 in Klein (1982) *Immunology*, Wiley-Interscience, New York. The recent observations that various immune effectors can directly or indirectly inhibit tumor growth has led to renewed interest in this approach to cancer therapy, see e.g., Herberman (1985) *Concepts Immunopathol.* 1:96–132 (1985) (natural killer cells resist tumor cell growth); Rosenberg, et al. (1988) *Ann. Rev. Immunol.* 4:681–709 (clinical use of IL-2-activated killer cells to treat cancer); Ralph, et al. (1988) *J. Exp. Med.* 167:712–717 (tumoricidal activity by macrophages stimulated by lymphokines); Tepper, et al. (1989) *Cell* 57:503≧512 (IL-4 has anti-tumor activity); M. Cohen, "Lymphokines and Tumor Immunity," pp. 237–253 in S. Cohen (ed.) (1990) *Lymphokines and the Immune Response*, CRC Press, Boca Raton; and the like.

For example, leukemias are a heterogeneous group of neoplasms arising from the malignant transformation of hematopoietic cells, and can be derived from either lymphoid or myeloid cell types. The transformed cells proliferate primarily in the bone marrow and lymphoid tissue where they interfere with normal hematopoiesis and immunity. They may also emigrate into the blood and infiltrate other tissues often leading to abnormal distributions of different cell types. Examples of leukemias include, acute lymphocytic leukemia (ALL), acute myelogenous leukemia (AML), chronic myelogenous leukemia (CML), chronic lymphocytic leukemia (CLL), hairy cell leukemia, and adult T cell leukemia (ATL).

Leukemias are typically identified as either acute or chronic. Acute forms have a rapid clinical course and without effective treatment can result in death within months. Acute leukemias are typically characterized by excessive proliferation of immature myeloid or lymphoid cells in the bone marrow, as a result of defects in the maturation process. In AML, the cells fail to mature beyond the myeloblast or promyelocyte level. In ALL, the cells fail to mature beyond the lymphoblastoid level.

Chronic leukemias have a more prolonged natural history. CLL is typically characterized by the overproduction and accumulation of mature appearing B lymphocytes. The neoplastic cells usually have B cell associated markers such as monoclonal surface IgM and Fc receptors. Approximately 5 percent of patients with CLL have the T cell form of CLL. The neoplastic cells in these diseases form rosettes with sheep erythrocytes and exhibit other T cell markers.

Hairy cell leukemia is a lymphoid neoplasm characterized by neoplastic cells having cytoplasmic projections. The disease is caused by the expansion of mature B cells which often produce monoclonal immunoglobulins.

Adult T cell leukemia (ATL) is associated with human T cell leukemia virus-I (HTLV-I). It is an aggressive malignancy of mature T cells, and is endemic to parts of Japan, the Caribbean, and Africa.

Lymphomas, in contrast to leukemias, are neoplastic transformations of cells that reside predominantly in lymphoid tissues. Lymphomas are typically divided between Hodgkin's disease and non-Hodgkin's lymphomas. In Hodgkin's disease the majority of the cells are small lymphocytes with a T cell phenotype. More than 90% of all cases of non-Hodgkin's lymphomas are of B cell derivation.

Treatment of the majority of these diseases has not been entirely successful. Prior art approaches have centered primarily on chemotherapy and radiation. To date, however, these treatments generally fail to effect long term remission or cure. Thus, the prior art lacks a safe, reliable treatment of neoplastic cell proliferation, particularly those which are IL-2-dependent. Recently, various models have provided data which support use of IL-10 to treat neoplastic conditions.

SUMMARY OF THE INVENTION

The invention relates to the use of interleukin-10 (IL-10) to reduce and/or prevent the growth of a tumor. The invention also includes pharmaceutical compositions comprising interleukin-10. Preferably, the interleukin-10 of the invention is selected from the group consisting of the mature polypeptides of the open reading frames defined by the following amino acid sequences:

```
Met His Ser Ser Ala Leu Leu Cys Cys   (SEQ ID NO: 1)

Leu Val Leu Leu Thr Gly Val Arg Ala

Ser Pro Gly Gln Gly Thr Gln Ser Glu

Asn Ser Cys Thr His Phe Pro Gly Asn

Leu Pro Asn Met Leu Arg Asp Leu Arg

Asp Ala Phe Ser Arg Val Lys Thr Phe

Phe Gln Met Lys Asp Gln Leu Asp Asn

Leu Leu Leu Lys Glu Ser Leu Leu Glu

Asp Phe Lys Gly Tyr Leu Gly Cys Gln

Ala Leu Ser Glu Met Ile Gln Phe Tyr

Leu Glu Glu Val Met Pro Gln Ala Glu

Asn Gln Asp Pro Asp Ile Lys Ala His
```

-continued

Val Asn Ser Leu Gly Glu Asn Leu Lys

Thr Leu Arg Leu Arg Leu Arg Arg Cys

His Arg Phe Leu Pro Cys Glu Asn Lys

Ser Lys Ala Val Glu Gln Val Lys Asn

Ala Phe Asn Lys Leu Gln Glu Lys Gly

Ile Tyr Lys Ala Met Ser Glu Phe Asp

Ile Phe Ile Asn Tyr Ile Glu Ala Tyr

Met Thr Met Lys Ile Arg Asn;

and

Met Glu Arg Arg Leu Val Val Thr Leu    (SEQ ID NO: 2)

Gln Cys Leu Val Leu Leu Tyr Leu Ala

Pro Glu Cys Gly Gly Thr Asp Gln Cys

Asp Asn Phe Pro Gln Met Leu Arg Asp

Leu Arg Asp Ala Phe Ser Arg Val Lys

Thr Phe Phe Gln Thr Lys Asp Glu Val

Asp Asn Leu Leu Leu Lys Glu Ser Leu

Leu Glu Asp Phe Lys Gly Tyr Leu Gly

Cys Gln Ala Leu Ser Glu Met Ile Gln

Phe Tyr Leu Glu Glu Val Met Pro Gln

Ala Glu Asn Gln Asp Pro Glu Ala Lys

Asp His Val Asn Ser Leu Gly Glu Asn

Leu Lys Thr Leu Arg Leu Arg Leu Arg

Arg Cys His Arg Phe Leu Pro Cys Glu

Asn Lys Ser Lys Ala Val Glu Gln Ile

Lys Asn Ala Phe Asn Lys Leu Gln Glu

Lys Gly Ile Tyr Lys Ala Met Ser Glu

Phe Asp Ile Phe Ile Asn Tyr Ile Glu

Ala Tyr Met Thr Ile Lys Ala Arg;

wherein the standard three letter abbreviation is used to indicate L-amino acids, starting from the N-terminus. These two forms of IL-10 are sometimes referred to as human IL-10 (or human cytokine synthesis inhibitory factor) and viral IL-10 (or BCRF1), respectively, e.g., Moore, et al. (1990) *Science* 248:1230–1234; Vieira, et al. (1991) *Proc. Nat'l Acad. Sci. USA* 88:1172–1176; Fiorentino, et al. (1989) *J. Exp. Med.* 170:2081–2095; Hsu, et al. (1990) *Science* 250:830–832. More preferably, the mature IL-10 used in the method of the invention is selected from the group consisting of:

Ser Pro Gly Gln Thr Gln Ser Glu    (SEQ ID NO: 3)

Asn Ser Cys Thr His Phe Pro Gly Asn

Leu Pro Asn Met Leu Arg Asp Leu Arg

Asp Ala Phe Ser Arg Val Lys Thr Phe

-continued

Phe Gln Met Lys Asp Gln Leu Asp Asn

Leu Leu Leu Lys Glu Ser Leu Leu Glu

Asp Phe Lys Gly Tyr Leu Gly Cys Gln

Ala Leu Ser Glu Met Ile Gln Phe Tyr

Leu Glu Glu Val Met Pro Gln Ala Glu

Asn Gln Asp Pro Asp Ile Lys Ala His

Val Asn Ser Leu Gly Glu Asn Leu Lys

Thr Leu Arg Leu Arg Leu Arg Arg Cys

His Arg Phe Leu Pro Cys Glu Asn Lys

Ser Lys Ala Val Glu Gln Val Lys Asn

Ala Phe Asn Lys Leu Gln Glu Lys Gly

Ile Tyr Lys Ala Met Ser Glu Phe Asp

Ile Phe Ile Asn Tyr Ile Glu Ala Tyr

Met Thr Met Lys Ile Arg Asn;

and

Thr Asp Gln Cys Asp Asn Phe Pro Gln    (SEQ ID NO: 4)

Met Leu Arg Asp Leu Arg Asp Ala Phe

Ser Arg Val Lys Thr Phe Phe Gln Thr

Lys Asp Glu Val Asp Asn Leu Leu Leu

Lys Glu Ser Leu Leu Glu Asp Phe Lys

Gly Tyr Leu Gly Cys Gln Ala Leu Ser

Glu Met Ile Gln Phe Tyr Leu Glu Glu

Val Met Pro Gln Ala Glu Asn Gln Asp

Pro Glu Ala Lys Asp His Val Asn Ser

Leu Gly Glu Asn Leu Lys Thr Leu Arg

Leu Arg Leu Arg Arg Cys His Arg Phe

Leu Pro Cys Glu Asn Lys Ser Lys Ala

Val Glu Gln Ile Lys Asn Ala Phe Asn

Lys Leu Gln Glu Lys Gly Ile Tyr Lys

Ala Met Ser Glu Phe Asp Ile Phe Ile

Asn Tyr Ile Glu Ala Tyr Met Thr Ile

Lys Ala Arg.

The present invention provides a method of treating a tumor in a mammal, said method comprising a step of administering an effective amount of interleukin-10 to the mammal. In various embodiments, the tumor is IL-2-dependent, a plasmacytoma, or a leukemia, including a lymphocytic leukemia such as a B cell lymphocytic leukemia. Preferably, the interleukin-10 is selected from the group consisting of viral interleukin-10 and human interleukin-10. Typically, the interleukin-10 is recombinantly produced, e.g., using a nucleotide sequence from a plasmid deposited with the ATCC® under accession number 68191 or 68192.

In additional embodiments, the method further comprises administering a therapeutically effective dose of a second biologically active agent. The administering can be by intravenous delivery. Various dosage ranges are provided, e.g., the effective amount is between about 2.5 and about 1000 µg/kg/day, between about 700 ng/kg/day and about 16 µg/kg/day; or between about 25 µg/kg/day and about 100 µg/kg/day. In other embodiments, the interleukin-10 is encapsulated in a liposome.

Alternatively, the invention provides a method of inhibiting interleukin-2 production by a neoplastic lymphocyte in a mammal suffering from neoplastic proliferation, where the method comprises administering to the mammal a therapeutically effective dose of a pharmaceutical composition comprising interleukin-10. Often, the neoplastic lymphocyte is a B cell, including a chronic lymphocytic leukemia cell. Preferably, the interleukin-10 is recombinant, e.g., produced using a nucleotide sequence from a plasmid deposited with the ATCC® under accession number 68191 or 68192.

In various embodiments, the administering is carried out by intravenous delivery. A preferred dosage ranges is between about 700 ng/kg/day and about 16 µg/kg/day. In another embodiment, the interleukin-10 is encapsulated in a liposome.

DETAILED DESCRIPTION OF THE INVENTION

Figure 1:
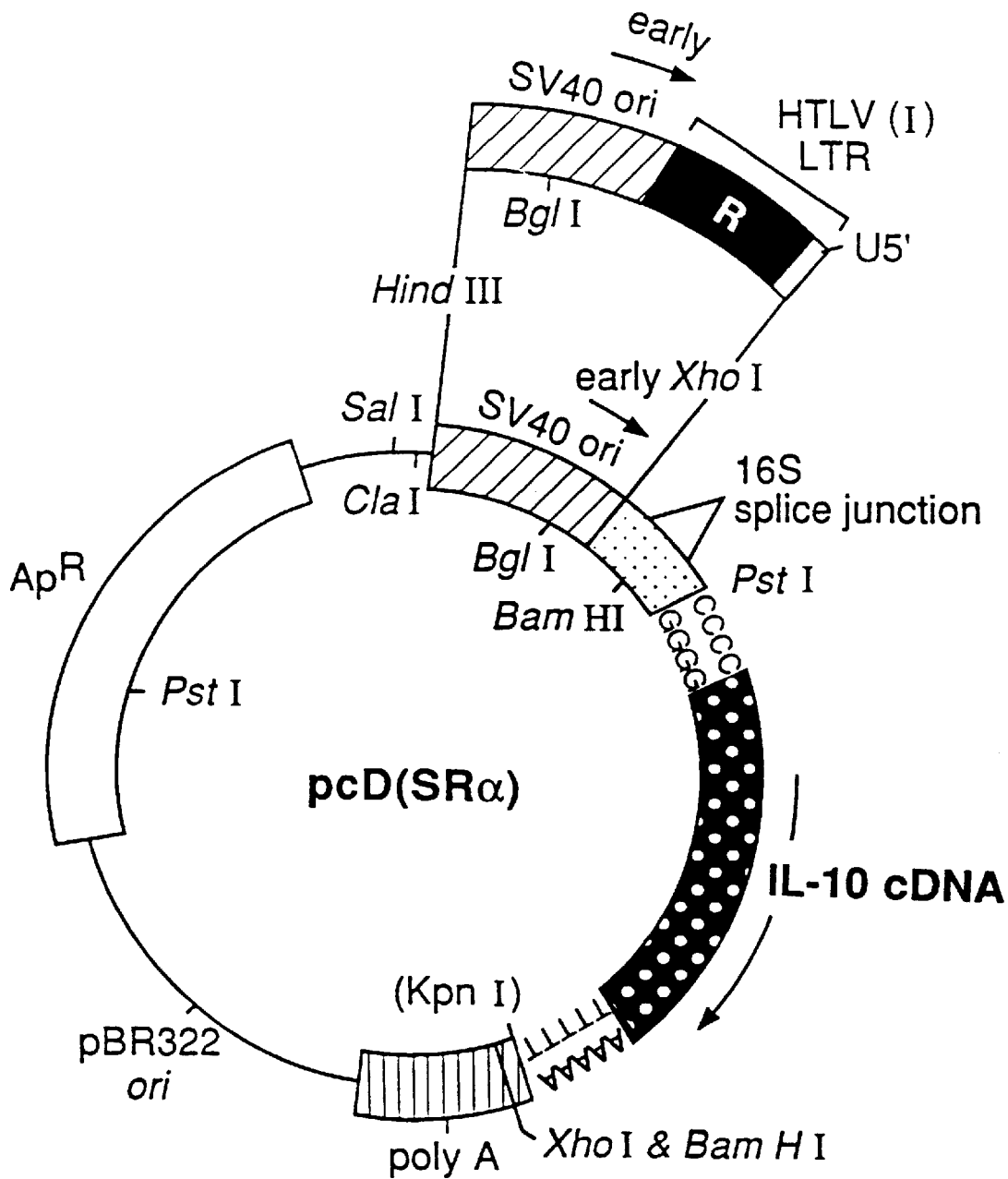
FIG. 1 shows a diagram of the vector pcD(SRα).

The present invention is directed to methods of using interleukin-10 (IL-10) to prevent and/or reduce the growth of cancers, including B cell lymphocytic leukemia (B-CLL). The invention also includes pharmaceutical compositions comprising IL-10 for carrying out the method.

Full length IL-10, fragments thereof, or IL-10 analogs can be isolated from appropriate cells and administered using standard methods. IL-10 for use in this invention is preferably selected from the group of mature polypeptides encoded by the open reading frames defined by the cDNA inserts of pH5C, pH15C, or pBCRF1 (SRα), which are deposited with the American Type Culture Collection (ATCC®), 10801 University Boulevard, Manassas, Va. 20110–22091, under accession numbers 68191, 68192, and 68193, respectively, and all deposited on Dec. 20, 1989. However, he terms "IL-10" and "IL-10 polypeptides" encompass naturally occurring or recombinant polypeptides or IL-10 agonists capable of specifically binding an IL-10 receptor and effecting a response to IL-10. These polypeptides useful in these methods include fragments, mutated forms, or modified polypeptides as described in detail, below. IL-10 is described, e.g., in U.S. Pat. No. 5,231,012, which is incorporated herein by reference.

I. Assays for Interleukin-10

IL-10 has been isolated from both mouse and human cells. IL-10s exhibit several biological activities which form the basis of assays and units. See, e.g., Moore, et al. (1993) Ann. Rev. Immunol. 11:165–190.

In particular, IL-10s have a property of inhibiting the synthesis of at least one cytokine in the group consisting of IFN-γ, lymphotoxin, IL-2, IL-3, and GM-CSF in a population of T helper cells induced to synthesize one or more of these cytokines by exposure to syngeneic antigen presenting cells (APCs) and antigen. In this activity, the APCs are treated so that they are incapable of replication, but their antigen processing machinery remains functional. This is conveniently accomplished by irradiating the APCs, e.g., with about 1500–3000 R (gamma or X-radiation) before mixing with the T cells.

Alternatively, cytokine inhibition may be assayed in primary or, preferably, secondary mixed lymphocyte reactions (MLR), in which case syngeneic APCs need not be used. MLRs are well known in the art, see, e.g., Bradley, pp. 162–166, in Mishell, et al. (eds.) (1980) Selected Methods in Cellular Immunology, Freeman, San Francisco; Battisto, et al. (1987) Meth. in Enzymol. 150:83–91; and Coligan et al. (eds.) (1991 and periodic supplements) Current Protocols in Immunology, Greene-Wiley, New York. Briefly, two populations of allogenic lymphoid cells are mixed, one of the populations having been treated prior to mixing to prevent proliferation, e.g., by irradiation. Preferably, the cell populations are prepared at a concentration of about $2 \times 10^6$ cells/ml in supplemented medium, e.g., RPMI 1640 with 10% fetal calf serum. For both controls and test cultures, mix 0.5 ml of each population for the assay. For a secondary MLR, the cells remaining after 7 days in the primary MLR are re-stimulated by freshly prepared, irradiated stimulator cells. The sample suspected of containing IL-10 may be added to the test cultures at the time of mixing, and both controls and test cultures may be assayed for cytokine production from 1 to 3 days after mixing.

Obtaining T cell populations and/or APC populations for IL-10 assays employs techniques well known in the art which are fully described, e.g., in Di Sabato, et al. (eds.) (1984) Meth. in Enzymol. 108:43–49. APCs for the preferred IL-10 assay are peripheral blood monocytes (PBMs). These are obtained using standard techniques, e.g., as described by Boyum (1984) Meth. in Enzymol. 108:88–102; Mage (1984) Meth. in Enzymol. 108:118–132; Litvin, et al. (1984) Meth. in Enzymol. 108:298–302; Stevenson (1989) Meth. in Enzymol. 108:242–249; and Romain, et al. (1984) Meth. in Enzymol. 108:148–153; which references are incorporated by reference. Preferably, helper T cells are used in the IL-10 assays, which are obtained by first separating lymphocytes from the peripheral blood then selecting, e.g., by panning or flow cytometry, helper cells using a commercially available anti-CD4 antibody, e.g., OKT4 described in U.S. Pat. No. 4,381,295 and available from Ortho Pharmaceutical Corp. The requisite techniques are described in Boyum (1968) Scand. J. Clin. Lab. Invest. 21(Suppl. 97):77–89; Mage (1984) Meth. in Enzymol., Vol. 108 (cited above), and in Bram, et al. (1986) Meth. in Enzymol. 121:737–748. Generally, PBLs are obtained from fresh blood by Ficoll-Hypaque density gradient centrifugation.

A variety of antigens can be employed in the assay, e.g., Keyhole limpet hemocyanin (KLH), fowl γ-globulin, or the like. Preferably, in place of antigen, helper T cells are stimulated with anti-CD3 monoclonal antibody, e.g., OKT3 disclosed in U.S. Pat. No. 4,361,549, in the assay.

Cytokine concentrations in control and test samples are measured by standard biological and/or immunochemical assays. Construction of immunochemical assays for specific cytokines is well known in the art when the purified cytokine is available, e.g., Campbell (1984) *Monoclonal Antibody Technology,* Elsevier, Amsterdam; Tijssen (1985) *Practice and Theory of Enzyme Immunoassays,* Elsevier, Amsterdam,; and U.S. Pat. No. 4,486,530 are exemplary of the extensive literature on the subject. ELISA kits for human IL-2, human IL-3, and human GM-CSF are commercially available from Genzyme Corp. (Boston, Mass.); and an ELISA kit for human IFN-γ is commercially available from Endogen, Inc. (Boston, Mass.). Polyclonal antibodies specific for human lymphotoxin are available from Genzyme Corp. which can be used in a radioimmunoassay for human lymphotoxin, e.g., Chard (1982) *An Introduction to Radioimmunoassay and Related Techniques,* Elsevier, Amsterdam.

Biological assays of the cytokines listed above can also be used to determine IL-10 activity. A biological assay for human lymphotoxin is disclosed in Aggarwal (1985) *Meth. in Enzymol.* 116:441–447; and Matthews, et al., pp. 221–225, in Clemens, et al. (eds.) (1987) *Lymphokines and Interferons: A Practical Approach,* IRL Press, Washington, D.C. Human IL-2 and GM-CSF can be assayed with factor dependent cell lines CTLL-2 and KG-1, available from the ATCC® under accession numbers TIB 214 and CCL 246, respectively. Human IL-3 can be assayed by its ability to stimulate the formation of a wide range of hematopoietic cell colonies in soft agar cultures, e.g., as described by Metcalf (1984) *The Hemopoietic Colony Stimulating Factors,* Elsevier, Amsterdam. INF-γ can be quantified with anti-viral assays, e.g., Meager, pp. 129–147, in Clemens, et al. (1987) (cited above).

Cytokine production can also be determined by mRNA analysis. Cytokine mRNAs can be measured by cytoplasmic mRNA dot hybridization as described by White, et al. (1982) *J. Biol. Chem.* 257:8569–8572; and Gillespie, et al., U.S. Pat. No. 4,483,920. Accordingly, these references are incorporated by reference. Other approaches include dot blotting using purified RNA, e.g., chapter 6, in Hames, et al. (eds.) *Nucleic Acid Hybridization A Practical Approach,* IRL Press, Washington, D.C.

In some cases, samples to be tested for IL-10 activity must be pretreated to remove predetermined cytokines that might interfere with the assay. For example, IL-2 increases the production of IFN-γ in some cells. Thus depending on the helper T cells used in the assay, IL-2 may have to be removed from the sample being tested. Such removals are conveniently accomplished by passing the sample over a standard anti-cytokine antibody affinity column.

For convenience, units of IL-10 activity are defined in terms of IL-10's ability to augment IL-4-induced proliferation of MC/9 cells, which are described in U.S. Pat. No. 4,559,310 and available from the ATCC® under accession number CRL 8306. One unit/ml is defined as the concentration of IL-10 which gives 50% of maximum stimulation of MC/9 proliferation above the level of IL-4 in the following assay. Prepare duplicate or triplicate dilutions of IL-4 and IL-10 in 50 μl of medium per well in a standard microtiter plate. Medium consists of RPMI 1640, 10% fetal calf serum, 50 μM 2-mercaptoethanol, 2 mM glutamine, penicillin (100 U/L), and streptomycin (100 μg/L). Add IL-4, 25 μl/well of 1600 U/ml (400 U/ml final) diluted in medium, and incubate overnight, e.g., 20–24 hours. $^3$H-thymidine (e.g., 50 μCi/ml in medium) is added at 0.5–1.0 μCi/well and the cells are again incubated overnight, after which cells are harvested and incorporated radioactivity measured.

In addition, IL-10 is involved in controlling the immune responses of different classes or subsets of T helper (Th) cells. Th cells can be divided into different subsets that are distinguished by their lymphokine production profiles. Th1 T cell clones produce interleukin-2 (IL-2) and interferon-γ (IFN-γ), whereas Th2 cell clones secrete IL-4 and IL-5 following activation by antigens or mitogenic lectins. Both classes of Th cell clones produce cytokines such as tumor necrosis factor-α (TNF-α), IL-3, and granulocyte-macrophage colony stimulating factor (GM-CSF). A third category of Th cells (Th0) produces IL-2, IFN-γ, IL-4, IL-5, TNF-α, IL-3, and GM-CSF simultaneously.

The different cytokine production patterns of Th1 and Th2 cells reflect their helper functions. Th1 cells are predominantly involved in delayed-type hypersensitivity responses, whereas Th2 cells are associated with antibody production. Since antibody (Th2 pathways) and delayed-type hypersensitivity (Th1 pathways) responses are often mutually exclusive, Th1 and Th2 cells are thought to have cross-regulatory effects. Indeed, IFN-γ produced by Th1 cells inhibits proliferation of Th2 cells, and, as shown here, IL-10 produced by Th2 cells inhibits cytokine synthesis, especially IFN-γ and IL-2 production, by Th1 cell clones.

Mouse (m)-IL-10 was cloned from a cDNA library established from activated TH2 cells. Moore, et al.(1990) *Science* 248:1230–1234. Human (h)-IL-10 was cloned from a cDNA library, established from a human Th0 CD4$^+$T-cell clone specific for tetanus toxin, using the mouse cDNA as a probe. Vieira, et al. (1991) *Proc. Nat'l. Acad. Sci. USA* 88:1172–1176. Human recombinant IL-10 consists of 160 amino acids with a predicted molecular size of 18.5 kD. It has only one potential N-glycosylation site but, in contrast to m-IL-10, h-IL-10 expressed in many mammalian cells is not glycosylated. Human IL-10 is a homodimer with a molecular weight of 39 kD. The h-IL-10 and m-IL-10 cDNAs are 81% homologous at the nucleotide level, whereas the overall amino acid sequence homology is approximately 73%. Both the human and mouse IL-10 genes are present as single copies in the genome and both are located on chromosome 1. Restriction mapping and DNA sequence analysis of a genomic m-IL-10 DNA clone demonstrated that the gene is encoded by five exons which span 5.1 kb. The structure of the h-IL-10 gene has not been as well characterized.

Mouse IL-10 is species-specific and does not act on human cells. In contrast, h-IL-10 is active on mouse cells. Both m-IL-10 and h-IL-10 have strong homology with a previously uncharacterized open reading frame in the Epstein-Barr virus (EBV) genome, BCRF1. This BCRF1 open reading frame was subcloned in an expression vector and the resulting BCRF1 protein produced by mammalian cells has biological activity. Hsu, et al. (1990) *Science* 250:830–832.

BCRF1 has a molecular size of approximately 17 kD and, like h-IL-10, it contains one potential N-linked glycosylation site, which is not normally used. Human IL-10 and BCRF1 have stronger homology at the amino-acid sequence level, whereas m-IL-10 and h-IL-10 are more closely related at the nucleotide sequence level. Based on these differences in sequence homologies, it has been proposed that BCRF1, now designated viral (v)-IL-10, represents a cellular IL-10 gene captured by the EBV during evolution and that there is selective pressure directed towards the preservation of a functional protein.

Viral-IL-10 and h-IL-10 share many biological activities when tested on human cells. Viral IL-10 inhibits cytokine synthesis by mouse Th1 cells, but lacks other m-IL-10 activities such as the induction of class II MHC expression on mouse B cells, and on mouse thymocytes, and mast cell proliferation, indicating that it conserved only some of the known IL-10 activities.

Human IL-10 is produced by Th2 cells as well as Th0 and Th1 clones following antigen-specific or polyclonal activation. In addition, approximately one-third of the CD8+ T-cell clones produced IL-10 following activation. Human B cells, EBV-transformed lymphoblastoid cell lines (LCLs), and monocytes also secrete IL-10 following activation. In particular, human monocytes are strong producers. In comparison to other T-cell derived cytokines, h-IL-10 is generally synthesized at a late stage following activation. The maximal production of IL-10 protein by CD4+ T-cell clones was observed between 24 and 48 h after activation, which correlated with the appearance of IL-10 mRNA 8 h after the activation of these cells and with maximal expression of IL-10 mRNA levels after 24 h.

Human IL-10 and v-IL-10 have cytokine synthesis inhibitory activity in human and mouse assay systems. Either h-IL-10 or v-IL-10 inhibited IFN-$\gamma$, GM-CSF, TNF-$\alpha$, lymphotoxin, and IL-3 production by peripheral blood mononuclear cells (PBM) activated by anti-CD3 mAbs or phytohemagglutin (PHA) antigen. This inhibition occurred at the transcriptional level. Vieira, et al. (1991) *Proc. Nat'l. Acad. Sci. USA,* 88:1172–1176. Reconstitution experiments in which human monocytes are pre-incubated with h-IL-10 or v-IL-10 indicate that the inhibition of cytokine production by T cells in this system is also mediated indirectly via the action of IL-10 on monocytes.

In contrast to m-IL-10, which has little or no inhibitory effect on antigen-induced proliferation of mouse Th1 T-cell clones, h-IL-10 and v-IL-10 strongly reduced the antigen-specific proliferative responses by human CD4+ T-cell clones when monocytes, but not when EBV-LCLs were used as APCs. Inhibition of the proliferative responses were also observed when antigenic peptides, which do not require antigen processing, were used, confirming the notion that h-IL-10 did not inhibit antigen processing. IL-10 strongly downregulated HLA-DR/DP and HLA-DQ expression on human monocytes. In addition, h-IL-10 inhibits the up-regulation of class II MHC molecules on monocytes by IFN-$\gamma$ and IL-4. The downregulation of class II MHC antigens by IL-10 may be responsible for the inhibition of antigen presentation by human monocytes. IL-10 and v-IL-10 had no effect on class II MHC expression on EBV-LCLs, which is compatible with the observation that IL-10 failed to reduce antigen-specific proliferative responses when EBV-LCLs were used as APCs. Thus, the reduced antigen-specific proliferative T-cell responses reflect a reduced capacity to stimulate T cells, rather than an active suppression of proliferative T-cell responses.

The present invention now provides evidence that h-IL-10 and v-IL-10 also have direct effects on human T cells. The Example section, below, shows the proliferative responses of human Th0-, Th1-, and Th2-like cells were inhibited by IL-10 when L cells transfected with Fc$\gamma$RII (CD32) were used in combination with either anti-CD3 mAbs, or a mitogenic pair of anti-CD2 mAbs. In addition, antigen-specific proliferative responses of human T-cell clones were inhibited by IL-10 when mouse L cells transfected with the relevant class II MHC molecules were used as APCs. IL-10 did not affect class II MHC expression in this system, since the constitutive expression of the transfected class II MHC genes is under the control the SV40 promoter.

Some of the inhibitory effects of IL-10 are due to a direct effect of IL-10 on the T cell clones via inhibition of IL-2 production at the mRNA level. The inhibitory effects were specific for IL-2, since IL-10 did not affect the production of IFN-$\gamma$, IL-4, IL-5, and GM-CSF. The interaction of IL-10 with an IL-10 receptor apparently triggers a signaling pathway that specifically inhibits IL-2 synthesis.

These results indicate that IL-10-induced inhibition of proliferation is mediated, at least in part, by a direct effect on T cell clones. Thus, IL-10 can now be used to inhibit IL-2-dependent cell proliferation that does not depend upon antigen presentation by MHC molecules, such as neoplastic cell proliferation.

Other assays can also be used to demonstrate the efficacy of the compositions of the present invention. For instance, nude mouse xenograft models can be used. Such models have been used to test a wide variety of chemotherapeutic agents (see, Howard, et al. (1991) *Cancer Res.* 51:3274–3280; and McLemore, et al. (1987) *Cancer Res.* 47:5132–5140.

II. Sources for IL-10

IL-10 suitable for use in the present invention can be obtained from a number of sources. For instance, it can be isolated from the culture medium of activated T cells capable of secreting the protein. In addition, IL-10 polypeptides can be synthesized using standard techniques as described in detail in published International Application, WO91/00349, which is incorporated herein by reference.

The protein is preferably recombinantly produced using isolated nucleic acids that encode IL-10 polypeptides. A wide range of single-cell and multicellular expression systems (i.e., host-expression vector combinations) can be used to produce the polypeptides of the invention by recombinant methods. Possible types of host cells include, but are not limited to, bacterial, yeast, insect, mammalian, and the like. Many reviews and references are available which provide guidance for making choices and/or modifications of specific expression systems, e.g., de Boer and Shepard, "Strategies for Optimizing Foreign Gene Expression in *Escherichia coli,"* pp. 205–247, in Kroon (ed.)(1983) *Genes: Structure and Expression,* John Wiley & Sons, New York, review several *E. coli* expression systems; Kucherlapati, et al. (1984) *Critical Reviews in Biochemistry* 16:349–379; and Banerji, et al. (1983) *Genetic Engineering* 5:19–31 review methods for transfecting and transforming mammalian cells; Reznikoff and Gold (eds.) (1986) *Maximizing Gene Expression,* Butterworths, Boston, review selected topics in gene expression in *E. coli,* yeast, and mammalian cells; and Thilly (1986) *Mammalian Cell Technology,* Butterworths, Boston, reviews mammalian expression systems. Likewise, many reviews are available which describe techniques and conditions for linking and/or manipulating specific cDNAs and expression control sequences to create and/or modify expression vectors suitable for use with the present invention, e.g., Sambrook, et al. (cited above); Ausubel, et al. (eds.) (1987 and periodic supplements) *Current Protocols in Molecular Biology,* Greene/Wiley. The isolation and characterization of such nucleic acids are also described in WO91/00349.

Clones comprising sequences that encode h-IL-10 have been deposited with the American Type Culture Collection (ATCC®), 10801 University Boulevard, Manassas, Va.

20110–22091, under the accession numbers 68191 and 68192. The following is a brief description of methods suitable for identification and recombinant expression of nucleic acid sequences that encode IL-10 polypeptides.

A. Isolation and Expression of IL-10 genes

Basic guides disclosing the general methods for identifying and expressing nucleotide sequences, e.g., one encoding IL-10, are Sambrook, et al. (1989) *Molecular Cloning, A Laboratory Manual* (2d ed.) Cold Spring Harbor Press, Cold Spring Harbor, N.Y.; and Ausubel, et al. (eds.) (1987 and periodic supplements) *Current Protocols in Molecular Biology*, Greene/Wiley, New York; which are incorporated herein by reference. Libraries are constructed from nucleic acid extracted from the appropriate cells, preferably Th2 cells.

Identification of clones harboring the sequences encoding IL-10 is performed by either nucleic acid hybridization, immunological, or expression and activity detection of the encoded protein, if an expression vector is used. Typically, oligonucleotide probes specific for sequences encoding IL-10 are used. For instance, oligonucleotide probes based on the deposited sequences disclosed in WO91/00349 are particularly useful. Oligonucleotide probes useful for identification of the sequences can also be prepared from conserved regions of related genes in other species. See, e.g., IntelliGenetics, Mountain View, Calif., or BCCG and other data bases, University of Wisconsin Biotechnology Center, Madison, Wis. Alternatively, degenerate probes based on the amino acid sequence of IL-10 can be used.

An alternative method for identification of IL-10 genes combines the use of synthetic oligonucleotide primers with polymerase extension on an mRNA or DNA template. Polymerase chain reaction (PCR) methods can be used to amplify the desired nucleotide sequence. Restriction endonuclease sites can also be incorporated into the primers to facilitate subsequent cloning steps. See, e.g., U.S. Pat. Nos. 4,683,195 and 4,683,202 and Innis (ed.)(1990) *PCR Protocols: A Guide to Methods and Applications*, Academic Press, New York, which are incorporated herein by reference. Genes amplified by the PCR reaction can be purified from agarose or polyacrylamide gels and cloned into an appropriate vector.

Standard transfection methods can be used to produce prokaryotic, mammalian, yeast or insect cell lines which express large quantities of IL-10. Exemplary *E. coli* strains suitable for both expression and cloning include W3110 (ATCC® No. 27325), JA221, C600, ED767, DH1, LE392, HB101, X1776 (ATCC® No. 31244), X2282, and RR1 (ATCC® No. 31343). Exemplary mammalian cell lines include COS-7 cells, CHO, and mouse L cells.

The particular expression vector used to express the gene is not particularly critical, though some expression systems may function at higher efficiencies. Conventional vectors used for expression of recombinant proteins in prokaryotic or eukaryotic cells may be used. A number of preferred vectors derived from SV40 are disclosed in WO91/00349. Preferred vectors include the pcD vectors described in Okayama, et al. (1983) *Mol. Cell. Biol.* 3:280–289; and Takebe, et al. (1988) *Mol. Cell. Biol.* 8:466–472, which are incorporated herein by reference. Other SV40-based mammalian expression vectors include those disclosed, e.g., in Kaufman, et al. (1982) *Mol. Cell. Biol.* 2:1304–1319; and U.S. Pat. No. 4,675,285, both of which are incorporated herein by reference. These SV40-based vectors are particularly useful in COS7 monkey cells (ATCC® No. CRL 1651), as well as other mammalian cells such as mouse L cells.

An *E. coli* expression system is disclosed by Riggs in U.S. Pat. No. 4,431,739, which is incorporated by reference. A particularly useful prokaryotic promoter for high expression in *E. coli* is the tac promoter, disclosed by de Boer in U.S. Pat. No. 4,551,433, which is incorporated herein by reference. Secretion expression vectors are also available for *E. coli* hosts. Particularly useful are the pIN-III-ompA vectors, disclosed by Ghrayeb, et al. (1984) *EMBO J.* 3:2437–2442, in which the cDNA to be transcribed is fused to the portion of the *E. coli* OmpA gene encoding the signal peptide of the ompA protein which, in turn, causes the mature protein to be secreted into the periplasmic space of the bacteria. U.S. Pat. Nos. 4,336,336 and 4,338,397 also disclose secretion expression vectors for prokaryotes. Accordingly, these are incorporated by reference.

Numerous strains of bacteria are suitable hosts for prokaryotic expression vectors including, e.g., *E. coli* strains W3110 (ATCC® No. 27325), JA221, C600, ED767, DH1, LE392, HB101, X1776 (ATCC® No. 31244), X2282, RR1 (ATCC® No. 31343), MRCI; strains of *Bacillus subtilis;* and other enterobacteriaceae such as *Salmonella typhimurium* or *Serratia marcescens,* and various species of Pseudomonas. General methods for deriving bacterial strains, such as *E. coli* K12 X1776, useful in the expression of eukaryotic proteins is disclosed by Curtis III in U.S. Pat. No. 4,190,495. Accordingly this patent is incorporated by reference.

In addition to prokaryotic and eukaryotic microorganisms, expression systems comprising cells derived from a multicellular organism may also be used to produce proteins of the invention. Of particular interest are mammalian expression systems because their posttranslational processing machinery is more likely to produce biologically active mammalian proteins. Several DNA tumor viruses have been used as vectors for mammalian hosts. Particularly important are the numerous vectors which comprise SV40 replication, transcription, and/or translation control sequences coupled to bacterial replication control sequences, e.g., the pcD vectors described by Okayama and Berg (1982) *Mol. Cell. Biol.* 2:161–170; and (1983) *Mol. Cell. Biol.* 3:280–289; and modified by Takebe, et al. (1988) *Mol. Cell. Biol.* 8:466–472. Accordingly, these references are incorporated herein by reference. Other SV40-based mammalian expression vectors include those disclosed by Kaufman and Sharp (1982) *Mol. Cell. Biol.* 2:1304–1319: and Clark, et al., in U.S. Pat. No. 4,675,285, both of which are incorporated herein by reference. Monkey cells are usually the preferred hosts for the above vectors. Such vectors containing the SV40 ori sequences and an intact A gene can replicate autonomously in monkey cells (to give higher copy numbers and/or more stable copy numbers than nonautonomously replicating plasmids). Moreover, vectors containing the SV40 ori sequences without an intact A gene can replicate autonomously to high copy numbers (but not stably) in COS7 monkey cells, described by Gluzman (1981) *Cell* 23:175–182 and available from the ATCC® (accession no. CRL 1651). The above SV40-based vectors are also capable of transforming other mammalian cells, such as mouse L cells, by integration into the host cell DNA.

Multicellular organisms can also serve as hosts for the production of the polypeptides of the invention, e.g., insect larvae, Maeda, et al. (1985) *Nature* 315:592–594; and (1989) *Ann. Rev. Entomol.* 34:351–372; Luckow, et al. (1988) *Bio/Technology* 6:47–55; O'Reilly, et al. (1992) *Baculovirus Expression Vectors: A Laboratory Manual* Freeman and Co., New York; and transgenic animals, Jaenisch (1988) *Science* 240:1468–1474.

Alternatively, the polypeptides may be commercially available from, e.g., PeproTech, Inc., Rocky Hill, N.J. See also U.S. patent application Ser. No. 07/917,806 for description of IL-10 and the means to make IL-10 or assay its activity.

B. Production of modified IL-10 polyteptides

The nucleotide sequences used to transfect the host cells can be modified according to standard techniques to yield IL-10 polypeptides or fragments thereof, with a variety of desired properties. IL-10 polypeptides can be readily designed and manufactured utilizing various recombinant DNA techniques well known to those skilled in the art. A number of preferred modifications are described. e.g., in WO91/00349. Modified IL-10 polypeptides can vary from the naturally-occurring sequence at the primary structure level by amino acid insertions, substitutions, deletions, and the like. These modifications can be used in a number of combinations to produce a final modified protein chain.

The amino acid sequence variants can be prepared with various objectives in mind, including increasing serum half life, facilitating purification or preparation, improving therapeutic efficacy, and lessening the severity or occurrence of side effects during therapeutic use. The amino acid sequence variants are usually predetermined variants not found in nature. The variants typically exhibit similar biological activity as naturally occurring IL-10. However, variants that are not capable of binding the IL-10 receptor on the target cell are useful nonetheless (a) as a reagent in diagnostic assays for IL-10, (b) as agents for purifying antibodies from antisera or hybridoma culture supernatants when insolubilized in accord with known methods, or (c) as immunogens for raising antibodies to IL-10, so long as at least one IL-10 epitope remains active.

In general, modifications of the sequences encoding the IL-10 polypeptides may be readily accomplished by a variety of well-known techniques, such as site-directed mutagenesis (see, e.g., Gillman and Smith (1979) *Gene* 8:81–97; and Roberts, et al. (1987) *Nature* 328:731–734, both of which are incorporated herein by reference). Most modifications are evaluated by routine screening in a suitable assay for the desired characteristic. For instance, WO91/00349 describes a number of in vitro assays suitable for identifying IL-10 activity. In addition, the assays described below can be used to measure the ability of modified protein to inhibit IL-2 synthesis. Modifications of other properties, e.g., redox or thermal stability, hydrophobicity, susceptibility to proteolysis, or the tendency to aggregate, are assayable according to standard techniques.

Insertional variants of the present invention are those in which one or more amino acid residues are introduced, typically into a predetermined site, in the protein. These may be added to or displace the preexisting residues. For instance, cleavable sequences may be fused to the protein (e.g., sequences from viral proteins) which allow ready affinity chromatographic purification of a recombinantly produced fusion protein. Once isolated, the cleavable sequences are removed by treatment with an appropriate protease and the desired molecule is recovered.

Substitutional variants are those in which at least one residue has been removed and a different residue inserted in its place. Non-natural amino acids (i.e., amino acids not normally found in native proteins), as well as isosteric analogs (amino acid or otherwise) are also suitable for use in this invention.

Substantial changes in function or immunological identity are made by selecting substituting residues that differ in their effect on the structure of the polypeptide backbone (e.g., as a sheet or helical conformation), the charge, or hydrophobicity of the molecule at the target site, or the bulk of the side chain. Substitutions which, in general, are expected to produce the greatest changes in function will be those in which (a) a hydrophilic residue, e.g., serine or threonine, is substituted for (or by) a hydrophobic residue, e.g., leucine, isoleucine, phenylalanine, valine, or alanine; (b) a cysteine or proline is substituted for (or by) any other residue; (c) a residue having an electropositive side chain, e.g., lysine, arginine, or histidine, is substituted for (or by) an electronegative residue, e.g., glutamine or asparagine; or (d) a residue having a bulky side chain, e.g., phenylalanine, is substituted for (or by) one having a less substantial side chain, e.g., glycine.

Substitutional variants of the subunits also include variants in which functionally homologous (having at least about 70% homology) domains of other proteins are substituted by routine methods for one or more of the domains of the IL-10 protein.

Another class of variants are deletional variants. Deletions are characterized by the removal of one or more amino acid residues from the IL-10 polypeptide sequence. Like many proteins, IL-10 contains separate functional regions, each having one or more distinct biological activities. Thus, polypeptide fragments comprising only a portion (usually at least about 60–80%, typically 90–95%) of the primary structure may be produced. Preferred deletional variants are disclosed in WO91/00349.

In addition, deletions of cysteine, methionine, or other labile residues may be desirable to increase the oxidative stability of the protein. Deletion or substitutions of potential proteolysis sites, e.g., Arg Arg, is accomplished by deleting one of the basic residues or substituting one by, e.g., glutaminyl or histidyl residues.

Use of posttranslational, e.g., glycosylation, variants are also provided. Variants, e.g., with different glycosylation patterns from native protein, may be produced, e.g., by expression in cells which process proteins differently from the natural source, or by treatment of the product with enzymes, e.g., which effect carbohydrate addition or removal.

C. Purification of IL-10 polypeptides

IL-10 polypeptides can be purified from the appropriate cells using standard techniques. Typically, following the growth of the recombinant cells and secretion of IL-10 into the culture medium, the medium is harvested and clarified by centrifugation or filtration to remove cells and cell debris. The proteins contained in the clarified medium are concentrated, e.g., by adsorption to a suitable resin, ammonium sulfate precipitation, polyethylene glycol precipitation, or ultrafiltration. Insoluble and intracellular proteins may be processed similarly, following solubilization, e.g., by detergent treatment. Other routine means known in the art may be equally suitable. Further purification of the proteins can be accomplished by routine modification of standard procedures known to those skilled in the art. Purification may require the use of, e.g., affinity chromatography, ion exchange chromatography, sizing chromatography, or other protein purification techniques to obtain homogeneity. See, e.g., Deutscher (ed.) (1990) *Guide to Protein Purification*, Methods in Enzymology, Vol. 182, Academic Press, New York, and other volumes of the Methods in Enzymology series.

III. Preparation and Administration of Pharmaceutical Compositions

When polypeptides of the present invention are expressed in soluble form, for example, as a secreted product of transformed yeast or mammalian cells, they can be purified according to standard procedures of the art, including steps of ammonium sulfate precipitation, ion exchange chromatography, gel filtration, electrophoresis, affinity chromatography, and/or the like, see e.g., Kaufman (1977) "Enzyme Purification and Related Techniques," *Methods in Enzymology* 22:233–577, and Scopes (1982) *Protein Purification: Principles and Practice*, Springer-Verlag, New York, which provide guidance in such purifications. Likewise, when polypeptides of the invention are expressed in insoluble form, e.g., as aggregates, inclusion bodies, or the like, they can be purified by standard procedures in the art, including separating the inclusion bodies from disrupted host cells by centrifugation, solubilizing the inclusion bodies with chaotropic and reducing agents, diluting the solubilized mixture, and lowering the concentration of chaotropic agent and reducing agent so that the polypeptide takes on a biologically active conformation. The latter procedures are disclosed, e.g., in the following references, which are incorporated by reference: Winkler, et al. (1986) *Biochemistry*, 25:4041–4045; Winkler, et al. (1985) *Biotechnology* 3:992–998; Koths, et al., U.S. Pat. No. 4,569,790; and European patent applications 86306917.5 and 86306353.3.

As used herein "effective amount" means an amount sufficient to reduce or prevent tumor cell growth. The effective amount for a particular individual may vary depending on such factors as the state and type of the neoplastic disease being treated, the overall health of the individual, method of administration, the severity of side-effects, and the like. Generally, IL-10 is administered as a pharmaceutical composition comprising an effective amount of IL-10 and a pharmaceutical carrier. A pharmaceutical carrier can be a compatible, non-toxic substance suitable for delivering the compositions of the invention to a patient. Generally, compositions useful for parenteral administration of such drugs are well known, see e.g., *Remington's Pharmaceutical Science*, 15th Ed. (Mack Publishing Company, Easton, Pa. 1980); *Goodman and Gilman's: The Pharmacological Bases of Therapeutics*, Pergamon Press, Parrytown, N.Y.; and various treatises on Pharmaceutical Dosage Forms (parenteral medications, tablets, or disperse systems) of the Pharmaceutical Science Series from Dekker, N.Y. Alternatively, compositions of the invention may be introduced into a patient's body by implantable or injectable drug delivery system, e.g. Urquhart, et al., *Ann. Rev. Pharmacol. Toxicol.*, Vol. 24, pp. 199–236 (1984); Lewis, ed. *Controlled Release of Pesticides and Pharmaceuticals* (Plenum Press, New York, 1981); U.S. Pat. Nos. 3,773,919; 3,270,960; and the like. See also, Langer, *Science*, 249:1527–1533 (1990). Various forms of gene therapy by introduction of recombinant DNA may also be used to introduce the protein into the mammal. See, e.g., Rosenberg (1992) *J. Clinical Oncology* 10:180–199; and Cournoyer and Caskey (1993) *Ann. Rev. Immunol.* 11:297–329.

When administered parenterally, the IL-10 is formulated in a unit dosage injectable form (solution, suspension, emulsion) in association with a pharmaceutical carrier. Examples of such carriers are normal saline, Ringer's solution, dextrose solution, and Hank's solution. Nonaqueous carriers such as fixed oils and ethyl oleate may also be used. A preferred carrier is 5% dextrose/saline. The carrier may contain minor amounts of additives such as substances that enhance isotonicity and chemical stability, e.g., buffers and preservatives. The IL-10 is preferably formulated in purified form substantially free of aggregates and other proteins at a concentration in the range of about 5 to 20 $\mu$g/ml. Preferably, IL-10 is administered by continuous infusion. Administration will be performed in an amount at least about 0.3 $\mu$g/kg, generally at least 1 $\mu$g/kg, more generally at least 2.5 $\mu$g/kg, often at least 5 $\mu$g/kg, more often at least 10 $\mu$g/kg, typically at least 25 $\mu$g/kg, and more typically at least 50 $\mu$g/kg. Generally, the dose will be less than about 2.5 mg/kg, more generally less than 1 mg/kg, often less than 500 $\mu$g/kg, more often less than 250 $\mu$g/kg, preferably less than 100 $\mu$g/kg, and more preferably less than 50 $\mu$g/kg. Thus, therapeutic doses will, e.g., fall into a range of about 50–800 $\mu$g/per/day for a 20–50 kg mammal (i.e., about 1–16 $\mu$g/kg/day). The daily infusion rate may be varied based on monitoring of side effects, blood cell counts, and efficacy. See Gilman, et al. (eds.) (1990) *Goodman and Gilman's: The Pharmacological Bases of Therapeutics* 8th ed., Pergamon Press, Parrytown, N.Y.; (1990) *Remington's Pharmaceutical Sciences*, 17th ed., Mack Publishing Co., Easton, Penn.; Avis, et al. (eds.) (1993) *Pharmaceutical Dosage Forms: Parenteral Medications* Dekker, N.Y.; Lieberman, et al. (eds.) (1990) *Pharmaceutical Dosage Forms: Tablets* Dekker, New York; and Lieberman, et al. (eds.) (1990) *Pharmaceutical Dosage Forms: Disperse Systems* Dekker, New York; each of which is incorporated herein by reference. Single dose packaging will typically be preferred.

The therapy of this invention may be combined with or used in association with or used in association with other chemotherapeutic or chemopreventive agents. See Thorn, et al. (eds.) *Harrison's Principles of Internal Medicine*, McGraw-Hill, New York; Wyngaarden, et al. (eds.) *Cecil Textbook of Medicine* Saunders, Pa.; and Weatherall, et al. (eds.) *Oxford Textbook of Medicine* Oxford University Press, New York.

Neoplastic conditions can be classified into three groups, benign, invasive non-metastatic, and metastatic, e.g., cancers,. See, e.g., DeVita, et al. (eds.) *Cancer: Principles and Practice of Oncology* Lippincott Co., Philadelphia. Cancers can be caused by genetic, environmental, and/or physiological causes. Among genetically derived cancers are multiple endocrine neoplasia, Gardner's syndrome, polyposis coli, nevoid basal cell carcinoma, and trichoepithelioma. See, e.g., Berkow, et al. (eds.) *The Merck Manual* Merck, Rahway, N.J. Various premalignant conditions include hamartomas, genodermatosis, immune deficiency syndromes, and various chromosomal abnormalities. For example, chromosomal abnormalities have been correlated with various myeloid leukemias, lymphomas, lymphocytic leukemias, myeloproliferative diseases, small cell lung cancer, Wilms' and Ewing's tumors, and retinoblastoma. Other environmental factors include various radiation and chemical mutagens, plus various parasitic or infectious agent caused conditions. Various immunologic disorders also lead to neoplastic conditions. Symptoms characterizing each of these neoplastic conditions will be found in standard oncology texts.

As discussed above, IL-10 polypeptides are particularly useful in therapeutic applications, e.g., to inhibit IL-2 dependent neoplastic cell proliferation. As used herein "IL-2 dependent neoplastic cell proliferation" encompasses any new or abnormal growth of tissue in which the growth is uncontrolled, progressive, and depends upon IL-2 for continued proliferation. The growth can be either benign or malignant. Malignant growth is typically characterized by greater degree of anaplasia (dedifferentiation) in the neoplastic cells. The IL-2-dependent neoplastic cells are typically derived from lymphoid or myeloid lines.

As discussed above, IL-2 is produced by T cells and has multiple activities on various cell types including T cells, NK cells, and B cells. IL-2 has been shown to act as a T cell growth factor and enhances the production of cytokines by T cells when stimulated in the presence of IL-2. IL-2 activates natural killer (NK) cells to kill target cells in a MHC non-specific manner. In addition, IL-2 is involved in the differentiation of B cells to switch to antibody production of certain isotypes.

Based on these activities of IL-2, the inhibition of IL-2 production by IL-10 could be important in several disease situations. For example, as means to reduce IL-2 driven proliferation of T cells in situations where T cell proliferation and growth is undesirable such as autoimmune disease, graft versus host reactions, and the like. It can also be used to prevent IL-2 dependent activation of NK cells and antibody production in autoimmune diseases.

Preferred diseases involving neoplastic growth that can be treated with the pharmaceutical compositions of the present invention include leukemias known to be dependent on IL-2 such as B cell chronic lymphocytic leukemia and adult T cell leukemia (ATL).

Pharmaceutical compositions of the invention are suitable for use in a variety of drug delivery systems. For a brief review of current methods for drug delivery, see, Langer (1990) *Science* 249:1527–1533, which is incorporated herein by reference. Methods for preparing administrable compounds will be known or apparent to those skilled in the art and are described in more detail in, e.g., *Remington's Pharmaceutical Science*, 17th ed., Mack Publishing Company, Easton, Pa. (1985), which is incorporated herein by reference.

The IL-10 peptides may be administered with a second biologically active agent, such as standard chemotherapeutic agents. Such agents include chemotherapeutic agents well known to the skilled clinician such as vincristine, daunorubicin, L-asparaginase, mitoxantrone, amsacrine, and the like. See also Thorn, et al. (eds.) *Harrison's Principles of Internal Medicine*, McGraw-Hill; and the *Merck Manual* and the *Merck Index*.

The IL-10 polypeptides of the invention may be prepared as formulations in pharmaceutically acceptable media, for example, saline, phosphate buffered saline (PBS), Ringer's solution, dextrose/saline, Hank's solution, and glucose. The compositions may contain pharmaceutically acceptable auxiliary substances as required to approximate physiological conditions, such as buffering agents, tonicity adjusting agents, wetting agents, detergents, and the like. Additives may also include additional active ingredients, e.g., bactericidal agents, or stabilizers. The amount administered to the patient will vary depending upon what is being administered, the purpose of the administration, such as prophylaxis or therapy, the state of the host, the manner of administration, and the like.

The pharmaceutical compositions are typically intended for transdermal or parenteral administration, e.g., intravenously, subcutaneously, or intramuscularly. Orally administrative forms are also desired and can be provided by modifying the composition to bypass the stomach environment. The composition can be used for prophylactic and/or therapeutic treatment. Preferably, the pharmaceutical compositions are administered intravenously. Thus, the invention provides compositions which comprise an IL-10 polypeptide dissolved or suspended in an acceptable carrier, preferably an aqueous carrier. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration.

In therapeutic applications, the pharmaceutical compositions are administered to a patient in an amount sufficient to inhibit neoplastic cell proliferation in the patient. An amount adequate to accomplish this is defined as a "therapeutically effective dose." The therapeutically effective dose of IL-10 will vary according to, for example, the particular use for which the treatment is made, the manner of administration, the health and condition of the patient, and the judgment of the prescribing physician. For example, the dose for continuous infusion will typically be the range of about 500 ng to about 800 $\mu$g per day for a 70 kg patient, preferably between about 10 $\mu$g and about 300 $\mu$g. The dose will typically be between 700 ng/kg/day and 16 $\mu$g/kg/day.

The concentration of IL-10 in the pharmaceutical formulations can vary widely, i.e., from about 10 $\mu$g about 5 mg/ml, preferably between about 100 $\mu$g and about 2 mg/ml. The concentration will usually be selected primarily by fluid volumes, viscosities, etc., in accordance with the particular mode of administration selected. Thus, a typical pharmaceutical composition for intravenous infusion could be made up to contain 250 ml of dextrose/saline solution and 2.5 mg IL-10.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, an IL-10 polypeptide of the invention, preferably 25%–75%. See, e.g., the Pharmaceutical Science Series from Dekker edited by Lieberman, including those on parenteral medications, tablets, and disperse systems.

For aerosol administration, the IL-10 polypeptides are preferably supplied in finely divided form along with a surfactant and propellant. Typical percentages of polypeptides are 0.01%–20% by weight, preferably 1%–10%. The surfactant should, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arbitol, mannitol, sorbitol, the hexitol anhydrides derived from sorbitol, and the polyoxyethylene and polyoxypropylene derivatives of these esters. Mixed esters, such as mixed or natural glycerides may be employed. The surfactant may constitute 0.1%–20% by weight of the composition, preferably 0.25–5%. The balance of the composition is ordinarily propellant. Liquified propellants are typically gases at ambient conditions, and are condensed under pressure. Among suitable liquified propellants are the lower alkanes containing up to 5 carbons, such as butane and propane; and preferably fluorinated or fluorochlorinated alkanes. Mixtures of the above may also be employed. In producing the aerosol, a container equipped with a suitable valve is filled with the appropriate propellant, containing the finely divided peptide(s) and surfactant. The ingredients are thus maintained at an elevated pressure until released by action of the valve.

In order to enhance the serum half-life, the IL-10 polypeptides may be encapsulated, introduced into the lumen of liposomes, prepared as a colloid, or another conventional technique may be employed which provides an extended lifetime of the peptides. Thus, in certain embodiments, the IL-10 may be encapsulated in a liposome. A variety of methods are available for preparing liposomes, as described in, e.g., Szoka, et al. (1980) *Ann. Rev. Biophys. Bioeng.* 9:467–508, U.S. Pat. Nos. 4,235,871; 4,501,728; and 4,837,028, all of which are incorporated herein by reference.

Following liposome preparation, the liposomes may be sized to achieve a desired size range and relatively narrow distribution of liposome sizes. Several techniques are available for sizing liposome to a desired size. One sizing method is described in U.S. Pat. No. 4,737,323, incorporated herein by reference.

Even under the most efficient encapsulation methods, the initial sized liposome suspension may contain up to 50% or more drug in a free (non-encapsulated) form. Several methods are available for removing non-entrapped compound from a liposome suspension. In one method, the liposomes in the suspension are pelleted by high-speed centrifugation leaving free compound and very small liposomes in the supernatant. Another method involves concentrating the suspension by ultrafiltration, then resuspending the concentrated liposomes in a replacement medium. Alternatively, gel filtration can be used to separate large liposome particles from solute molecules.

Following the above treatment, the liposome suspension is brought to a desired concentration for use in intravenous administration. This may involve resuspending the liposomes in a suitable volume of injection medium, where the liposomes have been concentrated, for example by centrifugation or ultrafiltration, or concentrating the suspension, where the drug removal step has increased total suspension volume. The suspension is then sterilized by filtration as described above. The liposomes comprising the peptides of the invention may be administered parenterally as described above.

It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled. The following examples are provided by way of illustration, not limitation.

EXAMPLES

The following examples serve to illustrate the present invention. Selection of vectors and hosts as well as the concentration of reagents, temperatures, and the values of other variable parameters are only to exemplify application of the present invention and are not to be considered as limitations thereof. See also, e.g., Maniatis, et al. (1982) *Molecular Cloning, A Laboratory Manual,* Cold Spring Harbor Laboratory, Cold Spring Harbor Press; Sambrook, et al. (1989) *Molecular Cloning: A Laboratory Manual,* (2d ed.), vols 1–3, CSH Press, NY; Ausubel, et al., *Biology,* Greene Publishing Associates, Brooklyn, N.Y.; or Ausubel, et al. (1987 and Supplements) *Current Protocols in Molecular Biology,* Greene/Wiley, New York; Innis, et al. (eds.) (1990) *PCR Protocols: A Guide to Methods and Applications* Academic Press, N.Y.; all of which are each incorporated herein by reference. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology,* vol. 182, and other volumes in this series; and manufacturer's literature on use of protein purification products, e.g., Pharmacia, Piscataway, N.J., or Bio-Rad, Richmond, Calif.; which are incorporated herein by reference. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe, et al. (1992) *OIAexpress: The High Level Expression & Protein Purification System* QUIAGEN, Inc., Chatsworth, Calif.: which are incorporated herein by reference.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

Example 1
Expression of Human CSIF in a Bacterial Host

A synthetic human CSIF gene is assembled from a plurality of chemically synthesized double stranded DNA fragments to form an expression vector designated TAC-RBS-hCSIF. Cloning and expression are carried out in a standard bacterial system, for example, *E. coli* K-12 strain JM101, JM103, or the like, described by Viera and Messing (1982) *Gene* 19:259–268. Restriction endonuclease digestions and ligase reactions are performed using standard protocols, e.g., Maniatis, et al. (1982) *Molecular Cloning: A Laboratory Manual,* Cold Spring Harbor Laboratory, New York, the Sambrook, et al. revision, and Ausubel, et al. (1987 and periodic supplements) *Current Protocols in Molecular Biology,* Greene/Wiley.

The alkaline method (Maniatis, et al., cited above) is used for small scale plasmid preparations. For large scale preparations a modification of the alkaline method is used in which an equal volume of isopropanol is used to precipitate nucleic acids from the cleared lysate. Precipitation with cold 2.5 M ammonium acetate is used to remove RNA prior to cesium chloride equilibrium density centrifugation and detection with ethidium bromide.

For filter hybridizations Whatman 540 filter circles are used to lift colonies which are then lysed and fixed by successive treatments with 0.5 M NaOH, 1.5 M NaCl; 1 M Tris-HCl pH 8.0, 1.5 M NaCl (2 min each); and heating at 80° C. (30 min). Hybridizations are in 6×SSPE, 20% formamide, 0.1% sodium dodecylsulphate (SDS), 100 $\mu$g/ml *E. coli* tRNA, at 42° C. for 6 hrs using $^{32}$P-labeled (kinased) synthetic DNAs. (20×SSPE is prepared by dissolving 174 g of NaCl, 27.6 g of NaH$_2$PO$_4$9H$_2$O, and 7.4 g of EDTA in 800 ml of H$_2$O. pH is adjusted to 7.4 with NaOH, volume is adjusted to 1 liter, and sterilized by autoclaving.) Filters are washed twice (15 min, room temperature) with 1×SSPE, 0.1% SDS. After autoradiography (Fuji RX film), positive colonies are located by aligning the regrown colonies with the blue-stained colonies on the filters. DNA is sequenced by the dideoxy method, see Sanger, et al. (1977) *Proc. Natl. Acad. Sci.*74:5463–5467. Templates for the dideoxy reactions are either single stranded DNAs of relevant regions recloned into M13mp vectors, e.g., Messing, et al. (1981) *Nucleic Acids Res.*9:309–321, or double-stranded DNA prepared by the minialkaline method and denatured with 0.2 M NaOH (5 min, room temperature) and precipitated from 0.2 M NaOH, 1.43 M ammonium acetate by the addition of 2 volumes of ethanol. DNA is synthesized by phosphoramidite chemistry using Applied Biosystems 380A synthesizers or equivalent. Synthesis, deprotection, cleavage, and purification (7M urea PAGE, elution, DEAE-cellulose chromotography) are performed as described in the 380A synthesizer manual.

Complementary strands of synthetic DNAs to be cloned (400 ng each) are mixed and phosphorylated with polynucleotide kinase in a reaction volume of 50 µl. This DNA is ligated with 1 µg of vector DNA digested with appropriate restriction enzymes, and ligations are in a volume of 50 µl at room temperature for 4 to 12 hours. Conditions for phosphorylation, restriction enzyme digestions, polymerase reactions, and ligation have been described (Maniatis, et al., cited above). Colonies are scored for lacZ- (when desired) by plating on L agar supplemented with ampicillin, isopropyl-1-thio-beta-D-galactoside (IPTG) (0.4 mM), and 5-bromo-4-chloro-3-indolyl-beta-D-galactopyranoside (X-gal) (40 mg/ml).

Figure 3:
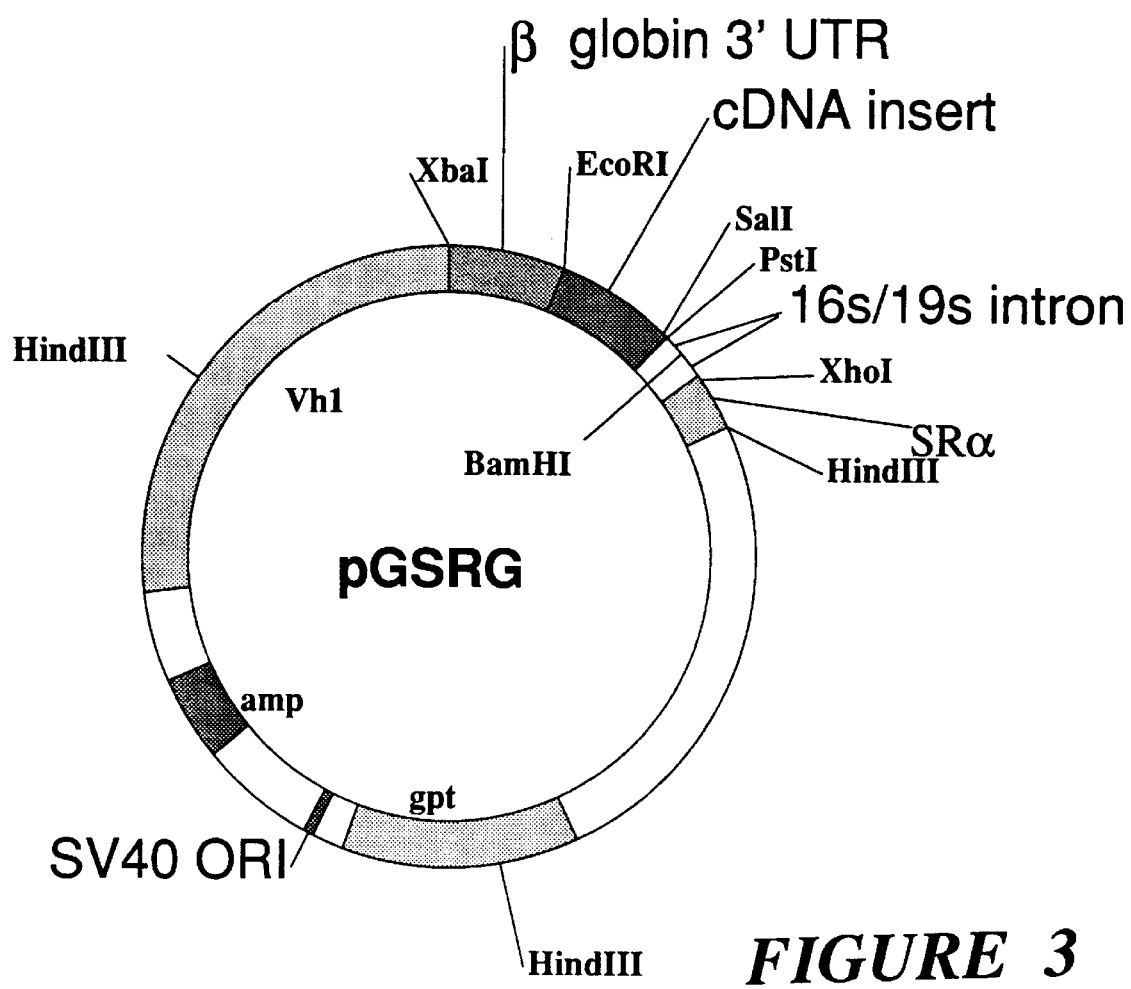
FIG. 3 shows a diagram of the vector pGSRG.

The TAC-RBS vector is constructed by filling-in with DNA polymerase the single BamHI site of the tacP-bearing plasmid pDR540 (Pharmacia). This is then ligated to unphosphorylated synthetic oligonucleotides (Pharmacia) which form a double-stranded fragment encoding a consensus ribosome binding site (RBS, GTAAGGAGGTTTAAC). After ligation, the mixture is phosphorylated and religated with the SstI linker ATGAGCTCAT. This complex was then cleaved with SstI and EcoRI, and the 173 bp fragment isolated via polyacrylamide gel electrophoresis (PAGE) and cloned into EcoRI-SstI restricted pUC19 (Pharmacia) (as described below). The sequence of the RBS-ATG-polylinker regions of the final construction (called TAC-RBS) is shown in FIG. 3.

The synthetic IL-10 gene is assembled into a pUC19 plasmid in eight steps. At each step inserts free of deletions and/or inserts can be detected after cloning by maintaining the lacZ(α) gene of pUC19 in frame with the ATG start codon inserted in step 1. Clones containing deletion and/or insertion changes can be filtered out by scoring for blue colonies on L-ampicillin plates containing x-gal and IPTG. Alternatively, at each step sequences of inserts can be readily confirmed using a universal sequencing primer on small scale plasmid DNA preparations, e.g., available from Boehringer Mannheim.

In step 1 the TAC-RBS vector is digested with SstI, treated with T4 DNA polymerase (whose 3' exonuclease activity digests the 3' protruding strands of the SstI cuts to form blunt end fragments), and after deactivation of T4 DNA polymerase, treated with EcoRI to form a 173 base pair (bp) fragment containing the TAC-RBS region and having a blunt end at the ATG start codon and the EcoRI cut at the opposite end. Finally, the 173 bp TAC-RBS fragment is isolated.

In step 2 the isolated TAC-RBS fragment of step 1 is mixed with EcoRI/KpnI digested plasmid pUC19 and synthetic fragment 1A/B which, as shown below, has a blunt end at its upstream terminus and a staggered end corresponding to an KpnI cut at its downstream terminus. This KpnI end is adjacent to and downstream of a BstEII site. The fragments are ligated to form the pUC19 of step 2.

In step 3 synthetic fragment 2A/B and 3A/B (shown below) are mixed with BstEII/SmaI digested pUC19 of step 2 (after amplification and purification) and ligated to form pUC19 of step 3. Note that the downstream terminus of fragment 3A/B contains extra bases which form the SmaI blunt end. These extra bases are cleaved in step 4. Also fragments 2A/B and 3A/B have complementary 9 residue single stranded ends which anneal upon mixture, leaving the upstream BstEII cut of 2A/B and the downstream blunt end of 3A/B to ligate to the pUC19.

In step 4 AflII/XbaI digested pUC19 of step 3 (after amplification and purification) is repurified, mixed with synthetic fragment 4A/B (shown below), and ligated to form pUC19 of step 4.

In step 5 XbaI/SalI digested pUC19 of step 4 (after amplification and purification) is mixed with synthetic fragment 5A/B (shown below) and ligated to form the pUC19 of step 5. Note that the SalI staggered end of fragment 5A/B is eliminated by digestion with HpaI in step 6.

In step 6 HpaI/PstI digested pUC19 of step 5 (after amplification and purification) is mixed with synthetic fragment 6A/B (shown below) and ligated to form the pUC19 of step 6.

In step 7 ClaI/SphI digested pUC19 of step 6 (after amplification and purification) is mixed with synthetic fragment 7A/B (shown below) and ligated to form the pUC19 of step 7.

In step 8 MluI/HindIII digested pUC19 of step 7 (after amplification and purification) is mixed with synthetic fragments 8A/B and 9A/B and ligated to form the final construction. The final construction is inserted into E. coli K-12 strain JM101, e.g., available from the ATCC® under accession number 33876, by standard techniques. After culturing, protein is extracted from the JM101 cells and dilutions of the extracts are tested for biological activity.

Fragment 1A/B                                (SEQ ID NO: 5)

AGCCCAGGCC AGGGCACCCA GTCTQAGAAC AGCTGCACCC ACTTC-
TCGGGTCCGG TCCCGTGGGT CAGACTCTTG TCGACGTGGG TGAAG-

CCAGGtAACC ggtac
GGTCCaTTGG c

Fragment 2A/B                                (SEQ ID NO: 6)

GtAACCTGCC TAACATGCTT CGAGATCTCC GAGATGCCTT CAGCA-
    GACGG ATTGTACGAA GCTCTAGAGG CTCTACGGAA GTCGT-

GAGTGAAGAC TTTCTTT
CTCACTTC

Fragment 3A/B                                (SEQ ID NO: 7)

CAAATGAAGG ATCAGCTGGA CAACTTGTTc TtAAG
TGAAAGAAA GTTTACTTCC TAGTCGACCT GTTGAACAAg AaTTC

Fragment 4A/B                                (SEQ ID NO: 8)

GAGTCCTTGC TGGAGGACTT TAAGGGTTAC CTGGGTTGCC AAGCC-
CTCAGGAACG ACCTCCTGAA ATTCCCAATG GACCCAACGG TTCGG-

TTGTCTGAGA TGATCCAGTT TTAt
AACAGACTCT ACTAGGTCAA AATaGAtC

Fragment 5A/B                                (SEQ ID NO: 9)

CTaGAGGAGG TGATGCCCCA AGCTGAGAAC CAAGACCCAG ACATC-
GAtCTCCTCC ACTACGGGGT TCGACTCTTG GTTCTGGGTC TGTAG-

AAGGCGCATG TtAACg
TTCCGCGTAC AaTTGcagct

Fragment 6A/B                                (SEQ ID NO: 10)

AACTCCCTGG GGGAGAACCT GAAGACCCTC AGGCTGAGGC TACGG-
TTGAGGGACC CCCTCTTGGA CTTCTGGGAG TCCGACTCCG ATGCC-

CGCTGTCATC GATctgca
GCGACAGTAG CTAg

Fragment 7A/B                                (SEQ ID NO: 11)

CGATTTCTTC CCTGTCAAAA CAAGAGCAAG GCCGTGGAGC AGGTG-

```
                    -continued
TAAAGAAG GGACAGTTTT GTTCTCGTTC CGGCACCTCG TCCAC- AAGAAcGCgT gcatg
TTCTTgCGCA c Fragment 8A/B                           (SEQ ID NO: 12)

CGCGTTTAAT AATAAGCTCC AAGACAAAGG CATCTACAAA GCCAT-
   AAATTA TTATTCGAGG TTCTGTTTCC GTAGATGTTT CGGTA-

GAGTGAGTTT GAC
CTCA

Fragment 9A/B                           (SEQ ID NO: 13)

ATCTTCATCA ACTACATAGA AGCCTACATG ACAAT-
CTCAAACTG TAGAAGTAGT TGATGTATCT TCGGATGTAC TGTTA-

GAAGATACGA AACTGA
CTTCTATGCT TTGACTtCga
(Lower case letters indicate that a base differs
from that of the native sequence at the same site)
```

Example 2
Expression of vIL-10 in COS 7 Monkey Cells

A gene encoding the open reading frame for vIL-10 was amplified by polymerase chain reaction using primers that allowed later insertion of the amplified fragment into an Eco RI-digested pcD(SRα) vector (FIG. 1). The coding strand of the inserted fragment is shown below (the open reading frame being given in capital letters).

```
aattaATGGA GCGAAGGTTA GTGGTCACTC       (SEQ ID NO: 14)
TGCAGTGCCT

GGTGCTGCTT TACCTGGCAC CTGAGTGTGG
AGGTACAGAC

CAATGTGACA ATTTTCCCCA GACCTAAGAG
ATGCCTTCAG

TCGTGTTAAA ACCTTTTTCC AGACAAAGGA
CGAGGTAGAT

AACCTTTTGC TCAAGGAGTC TCTGCTAGAG
GACTTTAAGG

ATGCCAGGCC CTGTCAGAAA TGATCCAATT
CTACCTGGAG

GAAGTCATGC CACAGGCTGA AAACCAGGAC
CCTGAAGCCA

AAGACCATGT CAATTCTTTG GGTGAAAATC
TAAAGACCCT

ACGGCTCCGC CTGCGCAGGT GCCACAGGTT
CCTGCCGTGT

GAGAACAAGA GTAAAGCTGT GGAACAGATA
AAAAATGCCT

TTAACAAGCT GCAGGAAAAA GGAATTTACA
AAGCCATGAG tGAATTTGAC ATTTTTATTA ACTACATAGA
AGCATACATG

ACAATTAAAG CCAGGTGAg
```

Clones carrying the insert in the proper orientation were identified by expression of vIL-10 and/or the electrophoretic pattern of restriction digests. One such vector carrying the vIL-10 gene was designated pBCRF1(SRα) and was deposited with the ATCC® under accession number 68193. pBCRF1(SRα) was amplified in *E. coli* MC1061, isolated by standard techniques, and used to transfect COS 7 monkey cells as follows: One day prior to transfection, approximately $1.5 \times 10^6$ COS 7 monkey cells were seeded onto individual 100 mm plates in Dulbecco's modified Eagle medium (DME) containing 5% fetal calf serum (FCS) and 2 mM glutamine. To perform the transfection, COS 7 cells were removed from the dishes by incubation with trypsin, washed twice in serum-free DME, and suspended to $10^7$ cells/ml in serum-free DME. A 0.75 ml aliquot was mixed with 20 μg DNA and transferred to a sterile 0.4 cm electroporation cuvette. After 10 minutes, the cells were pulsed at 200 volts, 960 μF in a BioRad Gene Pulser unit. After another 10 minutes, the cells were removed from the cuvette and added to 20 ml of DME containing 5% FCS, 2 mM glutamine, penicillin, streptomycin, and gentamycin. The mixture was aliquoted to four 100 mm tissue culture dishes. After 12–24 hours at 370° C., 5% $CO_2$, the medium was replaced with similar medium containing only 1% FCS and the incubation continued for an additional 72 hours at 37° C., 5% $CO_2$, after which the medium was collected and assayed for its ability to inhibit IFN-γ synthesis.

Ten ml aliquots of freshly isolated PBLs (about $2 \times 10^6$ cells/ml) were incubated at 37° C. with PHA (100 ng/ml) in medium consisting of (i) 90% DME supplemented with 5% FCS and 2 mM glutamine, and (ii) 10% supernatant from COS 7 cells previously transfected with pBCRF1(SRα). After 24 hours the cells and supernatants were harvested to assay for the presence of either IFN-γ mRNA or IFN-γ protein, respectively. Controls were treated identically, except that the 10% supernatant was from COS 7 cultures previously transfected with a plasmid carrying an unrelated cDNA insert. The vIL-10-treated samples exhibited about a 50% inhibition of IFN-γ synthesis relative to the controls.

Example 3
Expression of vIL-10 in *Escherichia coli*

A gene encoding the following mature vIL-10 may be expressed in *E. coli*.

```
Thr Asp Gln Cys Asp Asn Phe Pro Gln   (SEQ ID NO: 4)

Met Leu Arg Asp Leu Arg Asp Ala Phe

Ser Arg Val Lys Thr Phe Phe Gln Thr

Lys Asp Glu Val Asp Asn Leu Leu Leu

Lys Glu Ser Leu Leu Glu Asp Phe Lys

Gly Tyr Leu Gly Cys Gln Ala Leu Ser

Glu Met Ile Gln Phe Tyr Leu Glu Glu

Val Met Pro Gln Ala Glu Asn Gln Asp

Pro Glu Ala Lys Asp His Val Asn Ser

Leu Gly Glu Asn Leu Lys Thr Leu Arg

Leu Arg Leu Arg Arg Cys His Arg Phe

Leu Pro Cys Glu Asn Lys Ser Lys Ala

Val Glu Gln Ile Lys Asn Ala Phe Asn

Lys Leu Gln Glu Lys Gly Ile Tyr Lys

Ala Met Ser Glu Phe Asp Ile Phe Ile

Asn Tyr Ile Glu Ala Tyr Met Thr Ile

Lys Ala Arg
```

The cDNA insert of pBCRF1(SRα) is recloned into an M13 plasmid where it is altered twice by site-directed mutagenesis: first to form a Cla I site at the 5' end of the coding region for the mature vIL-10 polypeptide, and second to form a Bam HI site at the 3' end of the coding region for the mature vIL-10 polypeptide. The mutated sequence is then readily inserted into the TRPC11 expression vector described below.

Figure 2:
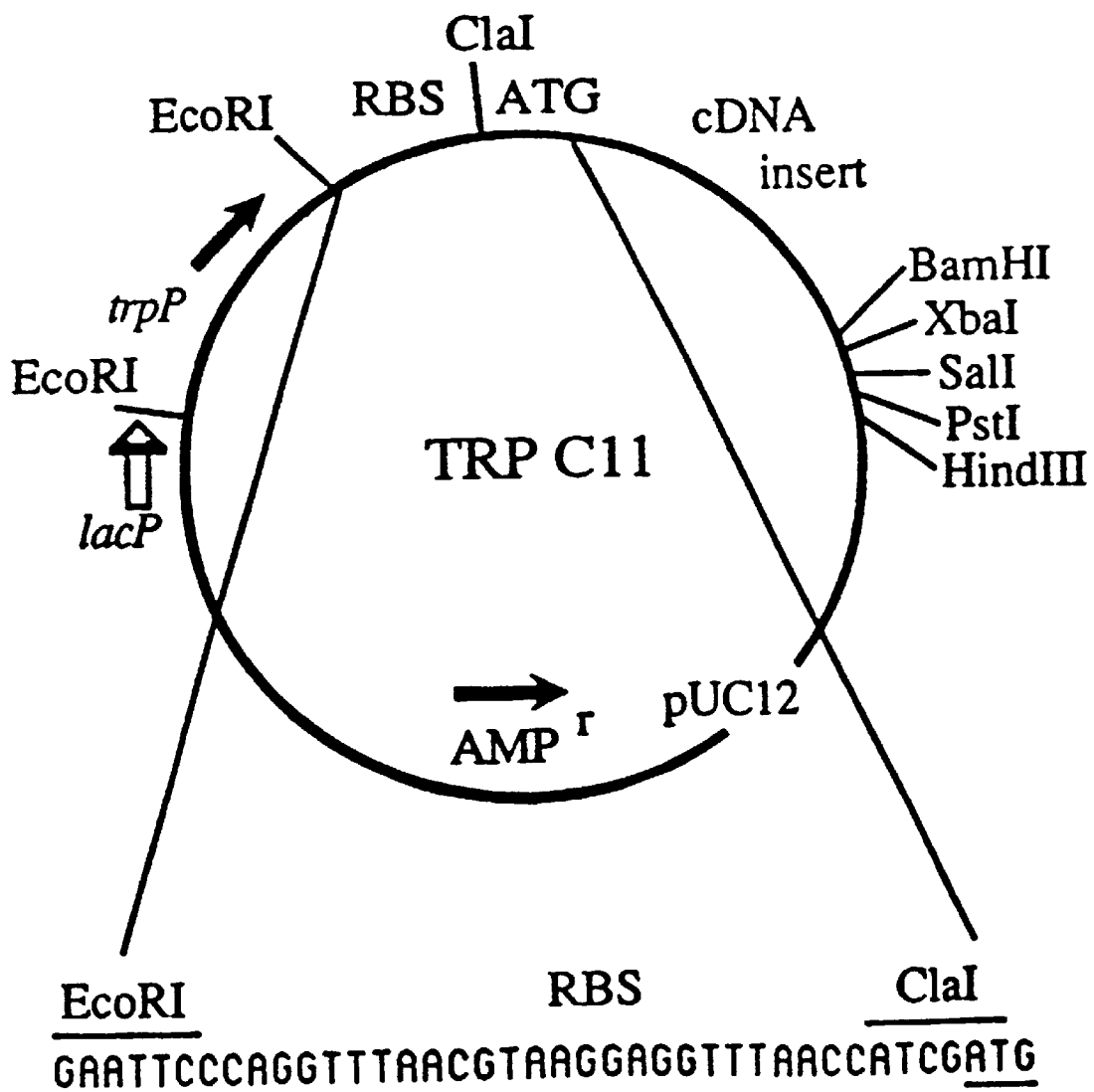
FIG. 2 shows a diagram of the vector TRP-C11.

The TRPC11 vector was constructed by ligating a synthetic consensus RBS fragment to ClaI linkers (ATGCAT) and by cloning the resulting fragments into ClaI restricted pMT11hc (which had been previously modified to contain the ClaI site). pMT11hc is a small (2.3 kilobase) high copy, $AMP^R$, $TET^S$ derivative of pBR322 that bears the πVX plasmid EcoRI-HindIII polylinker region. πVX is described by Maniatis, et al. (1982) *Molecular Cloning: A Laboratory Manual,* Cold Spring Harbor Laboratory. This was modified to contain the ClaI site by restricting pMT11hc with EcoRI and BamHI, filling in the resulting sticky ends and ligating with ClaI linker (CATCGATG), thereby restoring the EcoRI and BamHI sites and replacing the SmaI site with a ClaI site. One transformant from the TRPC11 construction had a tandem RBS sequence flanked by ClaI sites. One of the ClaI sites and part of the second copy of the RBS sequence were removed by digesting this plasmid with PstI, treating with Bal31 nuclease, restricting with EcoRI, and treating with T4 DNA polymerase in the presence of all four deoxynucleotide triphosphates. The resulting 30–40 bp fragments, e.g., SEQ ID NO: 15, were recovered via PAGE and cloned into SmaI restricted pUC12. A 248 bp *E. coli* trpP-bearing EcoRI fragment derived from pKC101 (described by Nichols, et al. (1983) *Methods in Enzymology* 101:155–164, Academic Press, N.Y., was then cloned into the EcoRI site to complete the TRPC11 construction, which is illustrated in FIG. 2. TRPC11 is employed as a vector for vIL-10 by first digesting it with ClaI and Bam HI, purifying it, and then mixing it in a standard ligation solution with the ClaI-Bam HI fragment of the M13 containing the nucleotide sequence coding for the mature BCRF1. The insert-containing TRPC11, referred to as TRPC11-BCRF1, is propagated in *E. coli* K12 strain JM101, e.g., available from the ATCC® under accession number 33876.

Example 4
Suppression of Tumors in a Mammal by IL-10

The effect of IL-10 on tumor growth was tested in an assay similar to that described by Tepper, et al. (1989) *Cell* 57:503–512. Briefly, the assay as applied here involves separately injecting mice with two groups of cells from a syngenic tumor cell line, one group being stably transfected with an IL-10-expressing plasmid, and the other being a non-transfected control. The incidence of tumor formation was then compared in mice separately injected with cells of the two groups.

In all experiments BALB/c mice were injected with either transfected or non-transfected plasmacytoma cells, e.g., NS1 myeloma tumor cells, available from the ATCC® under accession number TIB 18. NS1 cells were transfected by electroporation with plasmid pGSRG (illustrated in FIG. 3) carrying either the open reading frame (ORF) of mouse IL-10, viral IL-10, or human IL-10 inserted into the Xho I restriction site. pGSRG contains a marker for determining stably transfected NS1 cells and is a derivative of pSVDtβ described by Schnee, et al. (1987) *Proc. Natl. Acad. Sci.* 84:6904–6908. The IL-10 inserts for pGSRG were obtained as follows. PCR primers containing EcoRI linker sequences were prepared for each of pH5C, pBCRF1, and pcD(SRα)-F115 so that the ORFs of the respective cDNA inserts could be amplified. The amplified ORFs were then recloned into EcoRI digested pcD(SRα) vectors and separately expressed to select vectors containing the ORFs in the correct orientation. Finally, the XhoI fragments of the pcD(SRα)s were recloned into respective XhoI digested pGSRG plasmids.

The NS1 cells were transfected with the pGSRGs as follows. Cells (2–3×10$^6$) from a half-confluent 100 mm diameter petri dish were centrifuged, washed once in 10 ml of sterile phosphate buffered saline (PBS), centrifuged, and resuspended in 0.5 ml PBS. 20–100 µg of plasmid DNA were suspended in 1 ml PBS. The cells and DNA were mixed, placed in a cuvette on ice, and electrically shocked in a Bio-Rad Gene Pulser set to 960 microFarad capacitance and 200–300 volts. After 10 min on ice the cells were then plated onto a standard 96-well microtiter plate in 100 µl volumes. 48–78 hours later, 100 µl of mycophenolic acid selection medium (0.5 µg/ml mycophenolic acid, 100 µg/ml xanthine, 15 µg/ml hypoxanthine, 12–15% fetal calf serum, 600 µg/ml glutamine in DME High Glucose) was added to each well.

In a first experiment, 4, 3, 4, and 5 mice were each injected intraperitoneally with 5×10$^6$ non-transformed cells (control), pGSRG-mIL10-transformed cells, pGSRG-vIL10-transformed cells, and pGSRG-hIL10-transformed cells, respectively. After 4 weeks, 3 out of 4 of the control mice had developed visable tumors; none of the experimental mice developed tumors after 4 weeks.

In a second experiment, 16 mice were intraperitoneally injected with 5×10$^6$ non-transformed cells and 15 mice were intraperitoneally injected with 5×10$^6$ pGSRG-mIL10-transformed cells. After two weeks, 8 of the 16 control mice were re-injected with 5×10$^6$ non-transformed cells, and 7 of the 15 experimental mice were re-injected with 5×10$^6$ pGSRG-mIL10-transformed cells. 4 weeks after the initial injections the mice were examined for evidence of tumor development. 16 out of 16 of the control mice had developed visable tumors, and none of the experimental mice had developed any signs of tumors.

Example 5
IL-10 Inhibits Proliferation of Human Th0-, Th1-, and Th2- "Like" Clones Following Activation by Anti-CD3 mAbs Crosslinked on Mouse L Cells Transfected with CD32

Cells and cell lines. The T cell lines used in Examples 5 through 12 were CD2$^+$, CD3$^+$, CD4$^+$, and CD8$^-$. The clones HY-06,827, and 837 have been described previously in Yssel, et al. (1986) *Eur. J. Immunol.* 16:1187–1193; and Haanen, et al. (1991) *J. Exp. Med.* 174:583–592. T cell clone 827 recognizes tetanus toxin (TT) in the context of HLA-DR3 and T cell clone HY-06 recognizes peptide 2–12 from the 65 kD heat shock protein of Mycobacterium leprae. The antigen specificity of T cell clone 837 is not known.

The T cell clones SP-B21 and SP-A3 were obtained from a patient suffering from severe combined immunodeficiency (SCID) who was successfully reconstituted by fetal thymus and fetal liver transplantation. See Roncarolo, et al. (1988) *J. Exp. Med.* 168:2139–2152. T cell clones NP12, NP14, and NP-44 were established from PBMC of an atopic patient and proliferate specifically in response to the p89-117 peptide of the Der pI molecule, a major allergen of the house dust mite. Yssel, et al. (1992) *J. Immunol.* 148:738–745. T cell clones CR253, CR378, CR380, AP74, and AP75 were isolated from PBMC from patients suffering from chronic Lyme arthritis and are reactive with Borrelia burgdorferi 60 kD heat shock protein homologue (HSP60). Shanafelt, et al. (1991) *J. Immunol.* 146:3985–3992.

These T cell clones have been assigned to T helper subsets based on their lymphokine production profiles (see Table 1). T cell clones (2×10$^5$ cells/ml) were stimulated at two week intervals by a feeder cell mixture consisting of 10$^6$ irradiated (4000 rad) allogeneic peripheral blood leukocytes (PBL) per ml, $10^5$ irradiated (5000 rad) cells per ml of the Epstein-Barr Virus transformed B cell line (EBV-LCL) JY, and 0.1 mg/ml purified PHA (Wellcome Diagnostics, Beckenham, Kent, UK) in 24 well Linbro plates (Flow, Mc Lean, Va.), as described by Spits, et al. (1982) *J. Immunol.* 128:95–99. Three to four days after each restimulation, the cultures were split and further expanded in medium containing 20 U/ml rIL-2. All cloned T cell lines and EBV-LCL were cultured in Yssel's medium, see Yssel, et al. (1984) *J. Immunol. Methods* 72:219–227, supplemented with 1% human $AB^+$ serum.

Mouse L cells transfected with CD32 (FcγRII) (16.2CG7) were prepared as described in Peltz (1988) *J. Immunol.* 141:1891–1896, which is incorporated herein by reference. Briefly, an FcγRII cDNA clone, 16.2, isolated from human monocytic cell line U937 mutant was used (see Stuart, et al. (1987) *J. Exp. Med.* 166:1668–1684, which is incorporated herein by reference). Using standard site specific mutagenesis techniques, a mutant lacking the cytoplasmic domain was constructed by introducing mutations which altered the two lysine codons, after the first amino acid (arginine) of the predicted cytoplasmic domain, to stop codons. Transient transfection of mouse L cells was preformed according to standard techniques.

Reagents. Recombinant IL-10 was expressed in *E. coli* and purified according to the methods described in de Waal Malefyt, et al. (1991) *J. Exp. Med.* 174:915–924, which is incorporated herein by reference, and WO/91/00349, supra.

Proliferation assays. The cloned T cells were used 10 to 12 days after stimulation with feeder cells. At this stage the T cell clones were small and in a "resting" state. T cell clones ($2\times10^4$ cells/well) were incubated with CD32 transfected L cells ($2\times10^4$ cells/well) in the presence of anti-CD3 mAbs (SPV-T3b) (1 μg/ml) (Spits, et al. (1983) *Hybridoma* 2:423–437) in 200 μl flat-bottom plates (Falcon, Becton Dickinson, Lincoln Park, N.J.). The L cells were preincubated with the mAbs (1 μg/ml) for 1 hr in the presence or absence of IL-10 (100 U/ml) before the T cells were added and cultured for 72 hours. L cells were treated with mitomycin C (50 mg/ml) (Sigma Chemical Co. St. Louis, Mo.) at 37° C. for 45 min and subsequently washed four times before use. Cells were incubated for 72 h at 37° C. and 5% $CO_2$, pulsed with [$^3$H]TdR for 4 h and harvested as described previously in Yssel, et al. (1986) *Eur. J. Immunol.* 16:1187–1193, which is incorporated herein by reference. The results were expressed as cpm of [$^3$H]TdR incorporation and represent the mean of triplicate cultures.

Results

The effects of IL-10 on the proliferation of the T cell clones did not differ depending on the T cell lymphokine production patterns. T cell clones 837, SP-B21, and 827 produce IL-2, IL-4, and IFN-γ upon activation and therefore they are considered to represent human Th0 clones. HY-06, CR 253, CR 378, CR 380, AP 74, and AP75 produce high levels of IFN-γ and no detectable or low levels of IL-4 and IL-5. These clones are considered to represent human Th1-like clones, whereas NP12 and NP44 are human Th2-like clones, since they produced high levels of IL-4 and IL-5 and no detectable or low levels of IFN-γ following activation by their specific antigen. T cell clone SP-A3 produced IL-2, IL-5, IFN-γ, and GM-CSF, but not IL-4 following activation.

As shown in Table 1, IL-10 inhibited the proliferation of T cell clones 837, SP-B21, SP-A3, 827, HY-06, CR 253, CR 378, CR 380, AP 74, AP 75, NP 12 and NP 44 following activation. Thus, IL-10 was able to inhibit the proliferation of T cell clones belonging to all T helper subsets. Generally, IL-10 inhibited the proliferation of the T cell clones under the present test conditions by 20–50%. This inhibition was dose dependent and specific since it could be reversed by the neutralizing anti-IL-10 mAb 19F1.

TABLE 1

Effect of IL-10 on the proliferative responses of human Th0, Th1, and Th2 clones following activation by anti-CD3 mAbs crosslinked on CD32 (FcγRII) transfected L cells.

| | | [$^3$H]TdR incorporation (cpm × $10^{-3}$) | |
|---|---|---|---|
| Type T cell clone | T cell clone | control | +IL-10 (100 U/ml) |
| T helper 0 | 837 | 69 | 51 |
| | SP-B21 | 88 | 51 |
| | 827 | 5.5 | 3.5 |
| | SP-A3 | 28 | 12 |
| T helper 1 | HY-06 | 11 | 8 |
| | CR 253 | 12.8 | 10 |
| | CR 378 | 14.9 | 4.3 |
| | CR 380 | 19.8 | 8.5 |
| | AP 74 | 22 | 9 |
| | AP 75 | 38 | 33 |
| T helper 2 | NP 12 | 72 | 49 |
| | NP 44 | 15.3 | 7 |

In addition, murine IL-10, which is species specific, had no effect on the proliferation of these human T cell clones. This indicates that IL-10 acts directly on the T cell clones and not via the CD32 transfected mouse L cells used to crosslink the anti-CD3 mAbs. These results show that IL-10 directly inhibited proliferation of human Th0, Th1, and Th2 clones following activation via the TCR/CD3 complex by anti-CD3 mAbs crosslinked on L cells transfected with CD32.

Example 6
IL-10 Inhibits Proliferation of CD4$^+$ T Cell Clones Independently of Costimulatory Signals Provided by ICAM-1, LFA-3, or B7

Activation of human T cell clones can be modulated by interaction of accessory molecules on T cells with their counterstructures on antigen presenting cells (APC). Interactions between LFA-1 and ICAM1, CD2 and LFA3, CD28 and B7, or CTLA-4 and B7 have been shown to provide costimulatory signals enhancing proliferation and effector functions of T cells. To determine whether IL-10 inhibited T cell proliferation by affecting the costimulatory function of these accessory molecules L cells expressing CD32 and ICAM-1, LFA-3, or B7 were constructed.

Construction of pCD-SRα-LFA-3 HYG, pCDM8-ICAM-1 HYG, and pBJ-B7 HYG.

LFA-3 cDNA was obtained from a Raji cDNA library by PCR amplification using LFA-3 specific primers. The Raji cDNA library was constructed in the pCD-SRα vector as described previously. Matsui, et al. (1991) *Science*, 254:1788–1791. The following primers were used for cloning of the transmembrane form of LFA-3: sense: 5'-GGCTGCAGCGACGAGCCATGGTTGCTGGGAGC GA-CGCG-3' (nt 1-30) (SEQ ID NO: 16) and antisense: 5'-TTCATCTTCTGGTACCAATCAAT-TGGAGTTGGTTC-3' (nt 780–745) (SEQ ID NO: 17). The LFA-3 sense primer was designed with PstI site and the LFA-3 antisense primer with Kpnl site for convenient subcloning of the amplified products. Amplification was carried out under the following conditions: 1 μg of HindIII digested plasmid DNA of the Raji library was amplified in a 50 μl reaction containing 25 nmole of each primer, 125 mM of each dGTP, dATP, dCTP, and dTTP (Pharmacia, Uppsala, Sweden), 50 mM KCl, 10 mM Tris-HCl, pH 8.3, 1.5 mM MgCl$_2$, 1 mg/ml gelatin, and 5 units Taq polymerase (IBI, New Haven, Conn.). The mixtures were incubated in a Perkin-Elmer/Cetus DNA Thermal cycler for 20 cycles (denaturation 30s 94° C., annealing 30s 55° C., extension 60s 72° C.). An aliquot of 5 μl was removed and subjected to a second round of amplification under the same conditions. The reaction was extracted with CHCl$_3$ and loaded on 1% agarose gels. The amplified product with the expected size of 785 bp was cut from the gel after separation, isolated by absorption on silica using a Geneclean kit (Bio 101, La Jolla, Calif.), cut with PstI and KpnI and subcloned in Bluescript II KS (+) (Stratagene, La Jolla, Calif.).

A number of clones containing LFA-3 were isolated by standard techniques and 4 clones were sequenced by the dideoxy termination method using a Sequenase DNA sequencing kit (USB, Cleveland, Ohio). All 4 clones were 100% identical to the published sequence. The PstI-KpnI fragment of one of these clones was isolated and subcloned in the pCD-SRα 296 expression vector Matsui, et al.

pCDM8-ICAM-1 (Blanchard, et al., *J. Immunol.*, 138:2417 (1987)) was a gift of Dr. Brian Seed (Massachusetts General Hospital, Boston, Mass.). The aminocyclitol phosphotransferase gene which encodes for hygromycin-B resistance was placed under control of the SV40 promoter and polyadenylation signals and inserted in the SfiI sites of pCD-SRα-LFA-3 and pCDM8-ICAM-1 by standard techniques, yielding pCD-SRα-LFA-3 HYG and pCDM8-ICAM-1 HYG, respectively. pB7-B7-HYG contains human B7 under control of the SRα promotor, Makgoba, et al. (1988) *Nature* 331:86–88, and was a gift of Dr. L. Lanier (DNAX Research Institute).

L cells expressing HLA-DR3 or CD32 were transfected with pCD-SRα-LFA-3-HYG, pCDM8-ICAM-1-HYG, or pBJ-B7-HYG by lipofection (BRL, Gaithersburg, Md.) according to the manufacturer's procedures. Cells were split 48 hr after transfection and medium containing 200 μg/ml Hygromycin-B (Lilly, Indianapolis, Ind.) was added and changed every three days. After 12 days individual hygromycin-B resistant colonies were visible. These cells were pooled, stained for expression of LFA-3, ICAM-1, or B7 by indirect immunofluorescence and purified by two successive rounds of positive sorting on a FACS-Star Plus. The cotransfected cell lines were maintained in RPMI-1640 supplemented with 200 μg/ml hygromycin-B and 10% FCS.

Figure 4:
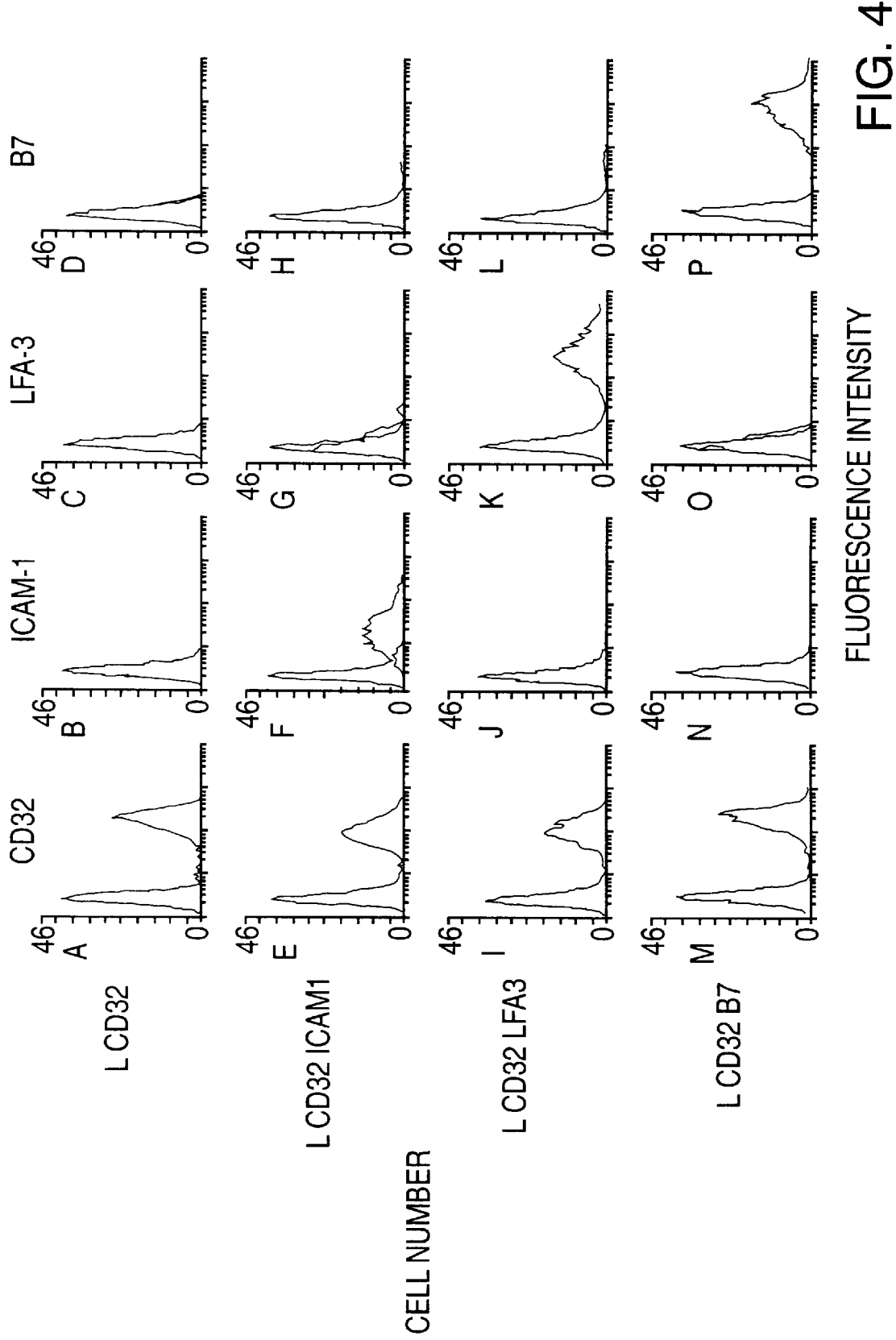
FIG. 4 is a FACS analysis of the phenotype of mouse L cells transfected with human CD32, ICAM-1, LFA3, or B7 genes.

For FACS analysis, cells were incubated in V-bottom microtiter plates (Flow Laboratories, McLean, Va.) with purified mAb (10 μg/ml) for 30 min at 4° C. After two washes with PBS containing 0.02 mM sodium azide and 1% BSA (Sigma, St. Louis, Mo.), the cells were incubated with 1/40 dilution of FITC labelled F(ab')2 fragments of goat anti-mouse antibody (TAGO, Inc., Burlingame, Calif.) for 30 min at 4° C. After three additional washes, the labeled cell samples were analyzed by flow microfluorimetry (FMF) on a FACScan (Becton Dickinson, Sunnyvale, Calif.). FACS analysis of the phenotype of these cell lines is shown in FIG. 4. The anti-LFA-3 mAb TS 2/9 is described in Krensky, et al. (1984) *J. Immunol.* 132:2180–2182. The anti-ICAM-1 mAb LB2 and the anti-B7 mAb L307 are described in Azuma, et al. (1992) *J. Exp. Med.* 175:353–360.

Figure 5:
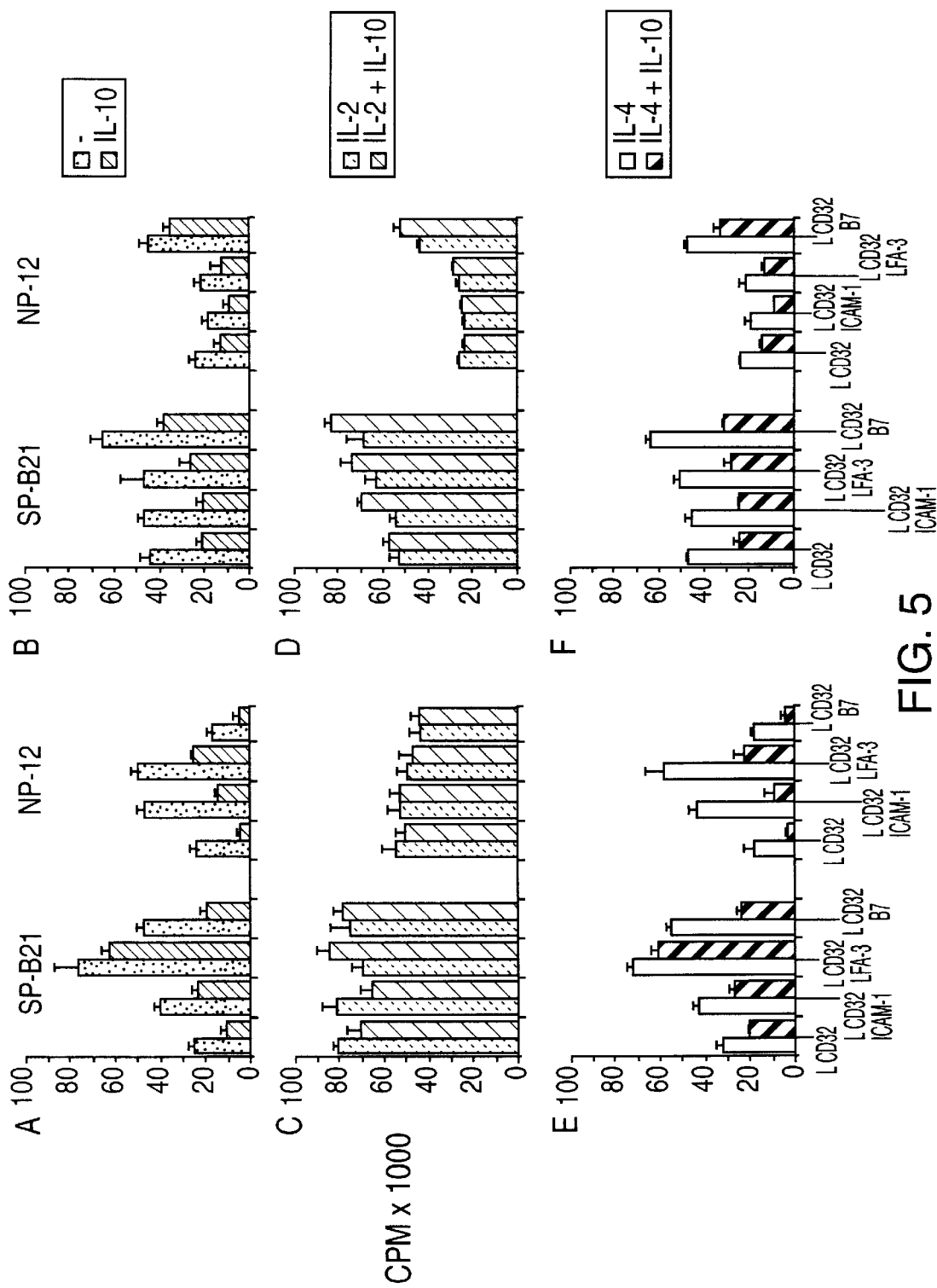
FIG. 5 has 6 panels, A through F. Panel A shows the proliferation of T cell clones SP-B21 and NP 12 when the clones are stimulated by anti-CD3 mAbs presented by CD32 transfected L cells which coexpress ICAM-1, LFA-3, or B7. Panel B shows the proliferation of T cell clones SP-B21 and NP 12 when the clones are stimulated by anti-CD2 mAbs presented by CD32 transfected L cells which coexpress ICAM-1, LFA-3, or B7. Panel C shows that IL-2 at low concentrations completely reverses the inhibitory effects of IL-10 on the proliferation of T cell clones SP-B21 and NP-12 activated by anti-CD3. Panel D shows that IL-2 at low concentrations completely reverses the inhibitory effects of IL-10 on the proliferation of T cell clones SP-B21 and NP12 activated by anti-CD2. Panel E shows that IL-4 added at concentrations of 200 U/ml cannot reverse the inhibitory effects of IL-10 on T cell proliferation activated by anti-CD3. Panel F shows that IL-4 added at concentrations of 200 U/ml cannot reverse the inhibitory effects of IL-10 on T cell proliferation as activated by anti-CD2.

In these experiments the T cell clones were activated by anti-CD3 or anti-CD2 mAbs crosslinked on L cells coexpressing CD32 and ICAM-1, LFA-3, or B7 in the absence or presence of IL-10. As shown in FIG. 5, the proliferation of T cell clones SP-B21 and NP 12 was enhanced when clones were stimulated by anti-CD3 mAbs presented by CD32 transfected L cells which coexpressed ICAM-1 and LFA-3. Coexpression of LFA-3 was more efficient in enhancing proliferation of T cell clones as compared to ICAM-1 or B7 and resulted consistently in a 2 to 4 fold increase in proliferation. Only a moderate enhancement in proliferation was observed by coexpression of ICAM-1. B7 generally did not affect the proliferation of T cell clones.

IL-10 inhibited the proliferative responses of T cell clones following activation by anti-CD3 mAbs crosslinked on L cells transfected with CD32 even in the presence of ICAM-1, LFA-3, and B7. However, the inhibition by IL-10 of the proliferation of T cell clones activated by L CD32 cells expressing LFA-3 was less pronounced.

Proliferation of T cell clones could also be induced by a mitogenic combination of anti-CD2 mAbs crosslinked on L CD32 cells, as shown in FIG. 5, panel B for T cell clones SP-B21 and NP-12. In these experiments, T cell clones (2×10$^4$ cells/well) were stimulated by the anti-CD2 mAbs X11-1 (0.5 mg/ml) and D66 (0.5 mg/ml), in 200 μl round-bottom plates (Linbro, Flow Laboratories, Mc. Lean, Va.) as described above. The production of these antibodies is described in Brottier (1985) *J. Immunol.* 135:1624–1631, which is incorporated herein by reference.

T cell proliferation was not affected when ICAM-1 or LFA-3 were coexpressed. However, a moderate enhancement of proliferation was observed when L cells coexpressing CD32 and B7 were used. The anti-CD2 induced proliferation of T cell clones was also inhibited by 30–50% in the presence of IL-10 when L cells expressing CD32 and ICAM-1, LFA-3, or B7 were used. IL-10 did not affect the expression of LFA-1, CD2, or CD28 by the T cell clones. Taken together these results indicate that the direct inhibitory effects of IL-10 on T cell proliferation were not a result of changes in costimulatory signals provided by ICAM-1, LFA-3, or B7.

Example 7

IL-2, but not IL-4, can Reverse the Inhibition of T Cell Proliferation by IL-10

To determine whether addition of IL-2 or IL-4 could reverse the inhibition of T cell proliferation induced by IL-10, T cell clones were activated by anti-CD3- or anti-CD2 mAbs crosslinked on L cells expressing CD32 and ICAM-1, LFA-3, or B7 in the presence of IL-2 or IL-4. IL-2 was added at 20 U/ml and IL-4 at 200 U/ml. Purified human r-IL-4 (specific activity 2×10$^7$ U/mg) was provided by Schering-Plough Research (Bloomfield, N.J.).

As shown in FIG. 5, panels C and D, addition of IL-2 at low concentrations could completely reverse the inhibitory effects of IL-10 on the proliferation of T cell clones SP-B21 and NP-12. However, IL-4 added at concentrations of 200 U/ml could not reverse the inhibitory effects of IL-10 on T cell proliferation (FIG. 5, panels E and F). Culturing T cell clones for up to 72 hrs in the presence of IL-10 did not result in a downregulation of IL-2 receptor α or β chain expression. In addition, activation of T cell clones with PHA in the presence of IL-10 had no effect on the induction of IL-2 receptor α and β chain expression. The anti-IL-2Rα mAb BB10 is described in Herve, et al. (1990) *Blood* 75:1017–1023. The anti-IL-2Rβ mAb Tu 27 is described in Takeshita (1989) *J. Exp. Med.* 169:1323–1332. Taken together these results indicate that the inhibition of T cell proliferation by IL-10 could be reversed by IL-2, but not by IL-4, and may result from an inhibition of IL-2 production.

Example 8

IL-10 Inhibits IL-2, but not IL-4, IL-5, IFN-γ, and GM-CSF Production by Human T Cell Clones To determine whether the direct inhibitory effect of IL-10 on the proliferation of T cell clones was due to an inhibition of IL-2 production, T cell clones 837, SP-B21, 827, HY-06, CR 253, NP 12, and NP 44 were activated by anti-CD3 mAbs crosslinked on L cells transfected with CD32 and ICAM-1, LFA-3, or B7 in the absence or presence of IL-10 for 24 hrs and the production of IL-2, IL-4, IL-5, IFN-γ, and GM-CSF was measured by cytokine specific ELISA. The sensitivity of these ELISA's was: IL-2, 10 pg/ml; IL-4, 50 pg/ml; IL-5, 50 pg/ml; IFN-γ, 300 pg/ml; and GM-CSF, 50 pg/ml.

T cell clones were collected for lymphokine production assays 10–12 days after stimulation with feeder cells as described above. Cells were incubated at 37° C. in an humidified atmosphere of 5% $CO_2$ for 24 hrs, culture supernatants were harvested, spun at 250×g, aliquoted, and stored at −20° C. prior to testing.

As shown in Table 2, polyclonal activation of T cell clones 827, SP-B21, and NP 44 resulted in high levels of lymphokine production according to their lymphokine production profiles. IL-10 strongly inhibited the production of IL-2 by these clones at all modes of activation tested, whereas the production of IL-4, IL-5, IFN-γ, and GM-CSF was not affected. IL-10 was able to inhibit IL-2 production by these T cell clones following activation by anti-CD3+ TPA and following $Ca^{++}$ ionophore+TPA, indicating that the mechanism of inhibition does not involve T cell receptor/ CD3 signal transduction pathways and that this mechanism acts downstream of protein kinase C activation.

TABLE 2

Effect of IL-10 on lymphokine production by T cell clones 827, HY-06, and NP44 following activation by anti-CD3 mAbs and TPA, PHA and TPA, or ConA

| | | Lymphokine production (ng/ml) | | | | | | | | | |
|---|---|---|---|---|---|---|---|---|---|---|---|
| | | IL-2 | | IL-4 | | IL-5 | | IFN-γ | | GM-CSF | |
| T cell clone | Stimulus | − | + | − | + | − | + | − | + | − | + |
| 827 | medium | ND | ND | ND | ND | ND | ND | ND | ND | ND | ND |
| | CD3 + TPA | 10.6 | 4.9 | 6.1 | 6.4 | 2.4 | 2.9 | 26.9 | 21.0 | 15.4 | 15.2 |
| | PHA + TPA | 17.8 | 5.7 | 5.1 | 4.0 | 0.8 | 0.6 | 32.8 | 39.3 | 14.3 | 15.5 |
| | ConA | 3.4 | 1.4 | 2.3 | 2.4 | ND | ND | 32.6 | 33.7 | 14.0 | 15.2 |
| HY-06 | medium | ND | ND | ND | ND | ND | ND | ND | ND | ND | ND |
| | CD3 + TPA | 1.3 | 0.2 | ND | ND | ND | ND | 23.9 | 25.5 | 10.0 | 13.2 |
| | PHA + TPA | 5.0 | 2.0 | ND | ND | ND | ND | 17.6 | 19.9 | 16.4 | 13.1 |
| | ConA | 5.1 | 0.2 | ND | ND | ND | ND | 12.8 | 14.9 | 14.2 | 13.3 |
| NP44 | medium | ND | ND | ND | ND | ND | ND | ND | ND | ND | ND |
| | CD3 + TPA | 0.5 | ND | 18.6 | 19.6 | 6.3 | 5.9 | 1.5 | 1.1 | 9.1 | 8.8 |
| | PHA + TPA | 1.3 | 0.3 | 35.4 | 33.5 | 8.4 | 7.9 | 1.4 | 1.6 | 13.1 | 14.6 |
| | ConA | 0.3 | ND | 20.1 | 18.7 | 7.8 | 7.3 | 2.6 | 2.6 | 18.9 | 18.9 |

T cell clones ($10^6$ cells/ml) were activated by anti-CD3 mAbs (0.5 μg/ml) and TPA (1 ng/ml), PHA (200 ng/ml) and TPA or ConA (10 μ/ml) in the absence or presence of IL-10 (100 U/ml) for 24 hours and the production of IL-2, IL-4, IL-5, IFN-g, and GM-CSF was determined by cytokine specific ELISA's. ND: not detected (less than sensitivity of respective ELISA)

Figure 6:
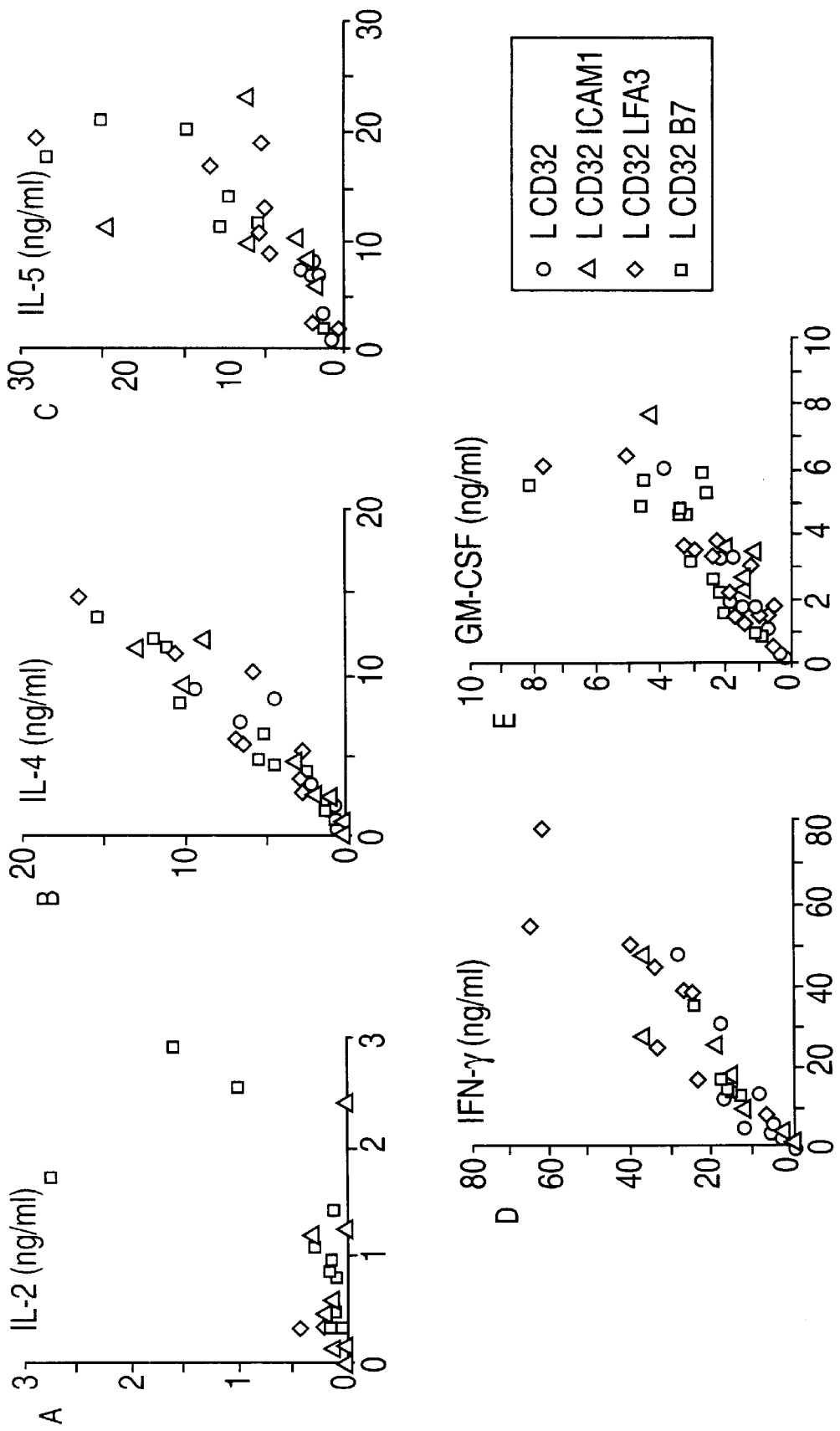
FIG. 6 shows that activation of human T cell clones results in the production of IL-2, IL-4, IL-5, GM-CSF, and IFN-γ according to their appropriate Th cell subset cytokine production profiles and that IL-10 has significant inhibitory effect on the production of IL-2 but not on the production of IL-4, IL-5, GM-CSF, and IFN-γ.

As shown in FIG. 6, activation of T cell clones resulted in the production of IL-2, IL-4, IL-5, GM-CSF, and IFN-γ according to their appropriate Th cell subset cytokine production profiles. Generally the highest levels of cytokine production were measured when T cell clones were activated by L cells expressing CD32 and LFA-3 or B7. In fact, the production of IL-2 was detected predominantly in supernatants of T cell clones activated by anti-CD3 on L CD32-LFA-3 and L CD32-B7 transfectants. IL-10 strongly inhibited the production of IL-2 by the T cell clones. Interestingly, the production of IL-4 was not affected by IL-10 whereas the production of IL-5, GM-CSF, and IFN-γ was only slightly inhibited by IL-10. Thus IL-10 specifically inhibited the IL-2 production by activated human T cell clones.

Example 9
IL-10 Inhibits IL-2 Production by Human T Cell Clones following Polyclonal Activation To further determine whether IL-10 was able to directly act on human T cell clones to inhibit lymphokine production, T cell clones 827, SP-B21, and NP 44 were activated by Tetradecanoylphorbol acetate (TPA) (Calbiochem), anti-CD3 mAbs, and TPA, PHA, PHA, and TPA, or a mitogenic combination of anti-CD2 mAbs in the absence of accessory cells. T cell clones were stimulated at concentrations of 1×$10^6$ cells/ml, PHA (100 ng/ml), anti-CD3 mAb SPV-T3b (1 μg/ml), and TPA (1 ng/ml).

Example 10
IL-10 Inhibits IL-2 Production by Human T Cell Clones at the mRNA Level To determine at what level IL-10 inhibited the production of IL-2, the expression IL-2, IL-4, IL-5, and IFN-γ mRNA was analyzed by Northern blots in T cell clones NP-12, HY-06, 827, SP-A3, 837, and SP-B21 following activation by anti-CD3 mAbs and TPA in the absence or presence of IL-10. Total RNA was isolated by the method of Chirgwin, et al. (1979) *Biochem.* 18:5294–5299. Northern analyses were performed as described in de Waal Malefyt (1989) *J. Immunol.* 142:3634–3642, which is incorporated herein by reference. The following probes were used for northern analysis: 285 bp PstI - XbaI fragment (nt 1–285) of pCD-hIL-2, which is described in Yokota, et al. (1987) *In Lymphokines* 13; 318 bp NheI - EcoRI fragment of pCD-hIL-4 (nt 106–424), which is described in Yokota, et al. (1986) *Proc. Natl. Acad. Sci. USA* 83:5894–5898; 1100 bp PstI - HincII fragment of pCD-hIFN-γ (nt 5–1106) Yokota, supra; and 1200 bp PstI fragment of pAL described in de Waal Malefyt, et al. (1990) *J. Immunol.* 145:2297–2303.

Figure 7:
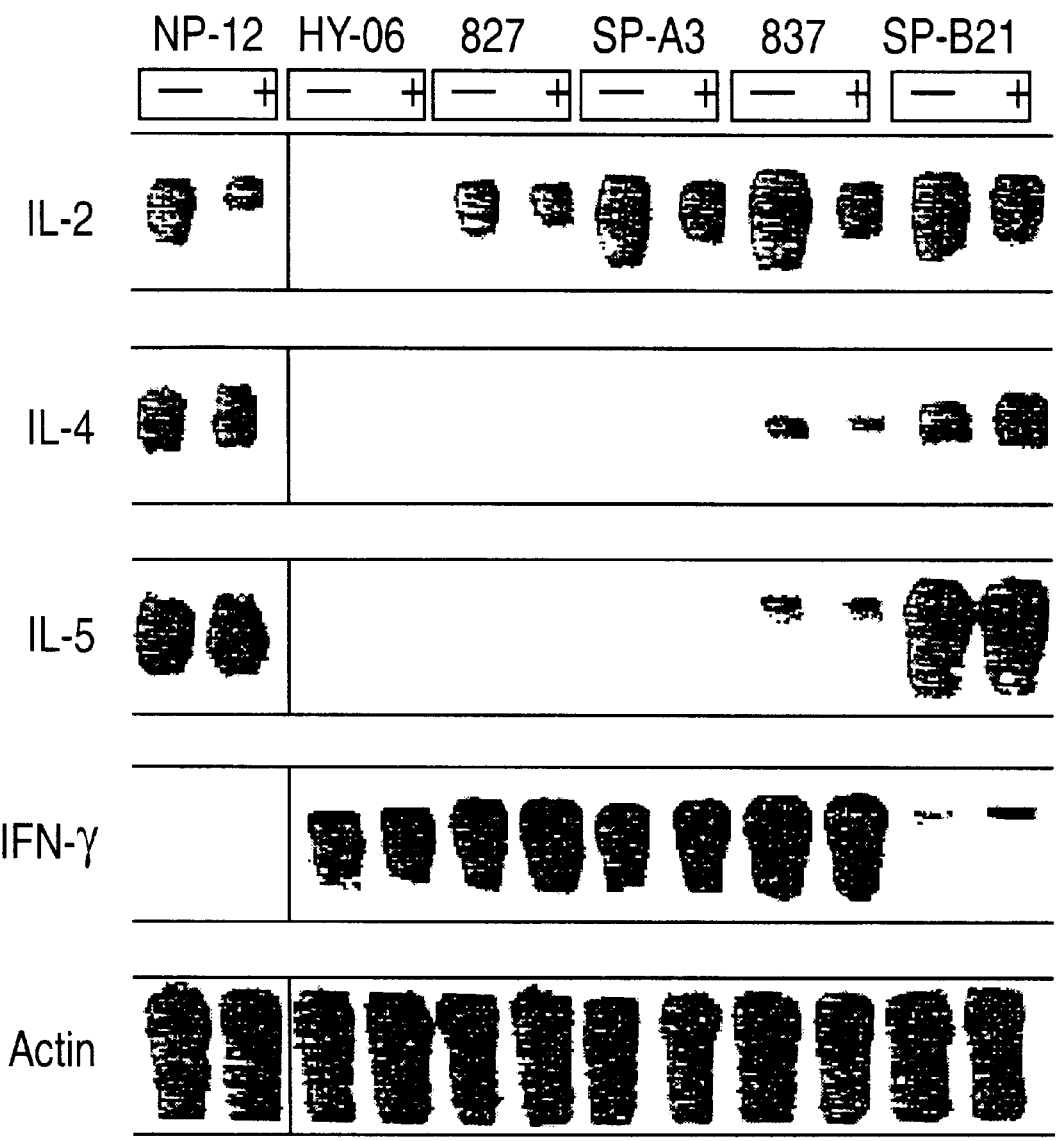
FIG. 7 shows that IL-10 strongly inhibits the levels of IL-2 mRNA expressed in T cell clones, but does not affect the expression of IL-4 and IL-5 by Th0- and Th2-like clones or the expression of IFN-γ by Th0- and Th1-like clones.

As shown in FIG. 7, IL-10 strongly inhibited the levels of IL-2 mRNA expressed in these clones, but did not affect the expression of IL-4 and IL-5 by Th0- and Th2-like clones or the expression of IFN-γ by Th0- and Th1-like clones. These results indicate that IL-10 specifically inhibits the production of IL-2 by human T cell clones at the mRNA level.

Example 11
IL-10 Inhibits IL-2 Production by T Cells Isolated from Peripheral Blood Cells Whether IL-10 could inhibit proliferation and IL-2 production by resting T cells was determined. T cells were isolated from peripheral blood and activated by anti-CD3 or anti-CD2 mAbs crosslinked on CD32 transfected L cells alone or CD32 L cells which coexpressed ICAM-1, LFA-3, or B7. Total PBMNC were isolated from buffy coats of healthy donors by centrifugation over Ficoll-Hypaque (Sigma Diagnostics, St. Louis, Mo.) density gradients as described by Boyum (1968) *Scan. J. Clin. Lab. Invest.* 21 (Suppl 97): 77–89, which is incorporated herein by reference. T cells were purified from PBMNC following plastic adherence, passage over nylon wool columns, and negative selection by magnetic depletion. Briefly, 100×10$^6$ PBMNC were cultured for 30 min at 37° C. in a 100 mm tissue culture dish (Becton Dickinson, Lincoln Park, N.J.) in Yssel's medium supplemented with 1% human AB serum. Non-adherent cells were removed and passed over a nylon wool (Robbins Scientific, Sunnyvale, Calif.) column (Julius, et al. (1973) *Eur. J. Immunol.* 3:645–649). Cells were subsequently incubated with saturating concentrations of anti-CD14 (Leu M3), CD16 (Leu 11a), CD19 (Leu 12), and CD56 (Leu 19) mAbs for 30 min at 4° C., washed and incubated with sheep anti-mouse IgG coated magnetic beads (Dynabeads M450, Dynal A. S., Oslo, Norway) at a bead to cell ratio of 40:1. The mixture was incubated with gentle shaking for 30 min at 4° C. and rosetted cells were removed with the magnetic particle concentrator according to manufacturer's recommendations. The T cell populations were 97–99% CD2$^+$, CD3$^+$. Anti-CD14 (Leu-M3), CD16 (Leu 11a), CD19 (Leu 12), and CD56 (Leu 19) mAbs and control mAbs of the appropriate isotypes were purchased from Becton Dickinson, Mountain View, Calif.

PBMNC T cells (2×10$^5$ cells/well) were stimulated by anti-CD3 or anti-CD2 mAbs crosslinked on LFcγRII cell transfectants as described in the previous section. Culture supernatants were harvested after 24 hrs of incubation at 37° C.

Figure 8:
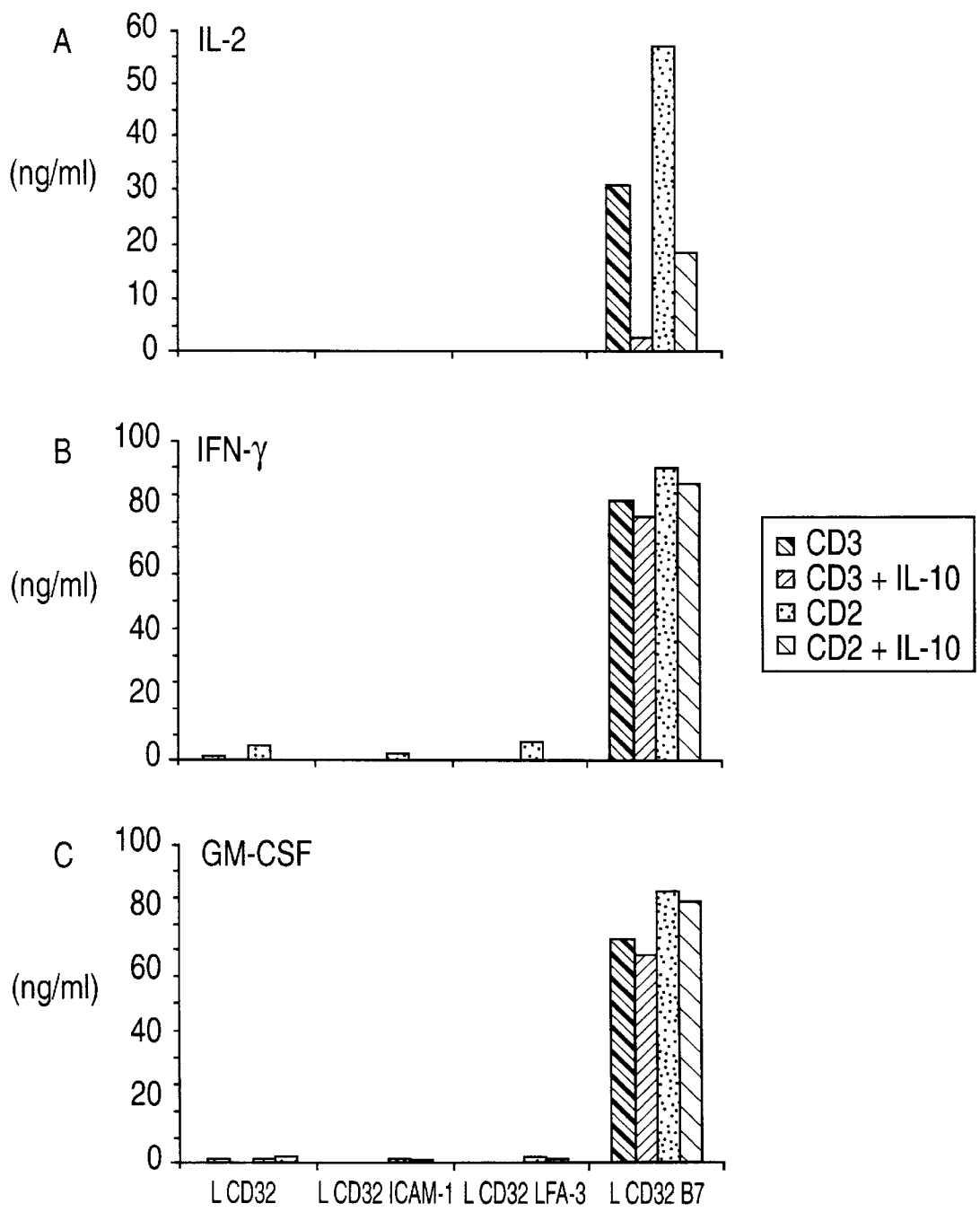
FIG. 8 shows that resting T cells are completely dependent on the presence of the B7 antigen on the CD32 L cells for activation and lymphokine production in combination with anti-C3 and anti-CD2 mAbs. IL-10 is able to inhibit IL-2 production but not production of IFN-γ or GM-CSF.

As shown in FIG. 8, resting T cells were completely dependent on the presence of the B7 antigen on the CD32 L cells for activation. Both anti-CD3 or anti-CD2 mAbs crosslinked on CD32 L cells were ineffective in inducing T cell proliferation and lymphokine production. In addition, these cells remained ineffective following cotransfection of ICAM-1 or LFA-3 into these cells. However, anti-CD2 or anti-CD3 mAbs crosslinked to CD32 L cells that had been cotransfected with B7 induced strong T cell proliferation and high levels of IL-2, IFN-γ and GM-CSF production. IL-10 did not significantly inhibit the proliferation of the resting T cells under these conditions. In contrast, IL-10 did inhibit the production of IL-2, but not the production of IFN-γ and GM-CSF by these cells (FIG. 8). However, the levels of IL-2 produced in the presence of IL-10 were still sufficient to induce maximal proliferation at the time point test (Day 3). Collectively these results indicate that engagement of CD28 or CTLA-4 on the T cells by interaction with B7 on the accessory cell is absolutely required for induction of proliferation and lymphokine production by resting T cells and that IL-10 is still able to inhibit IL-2 production under these conditions.

Figure 9:
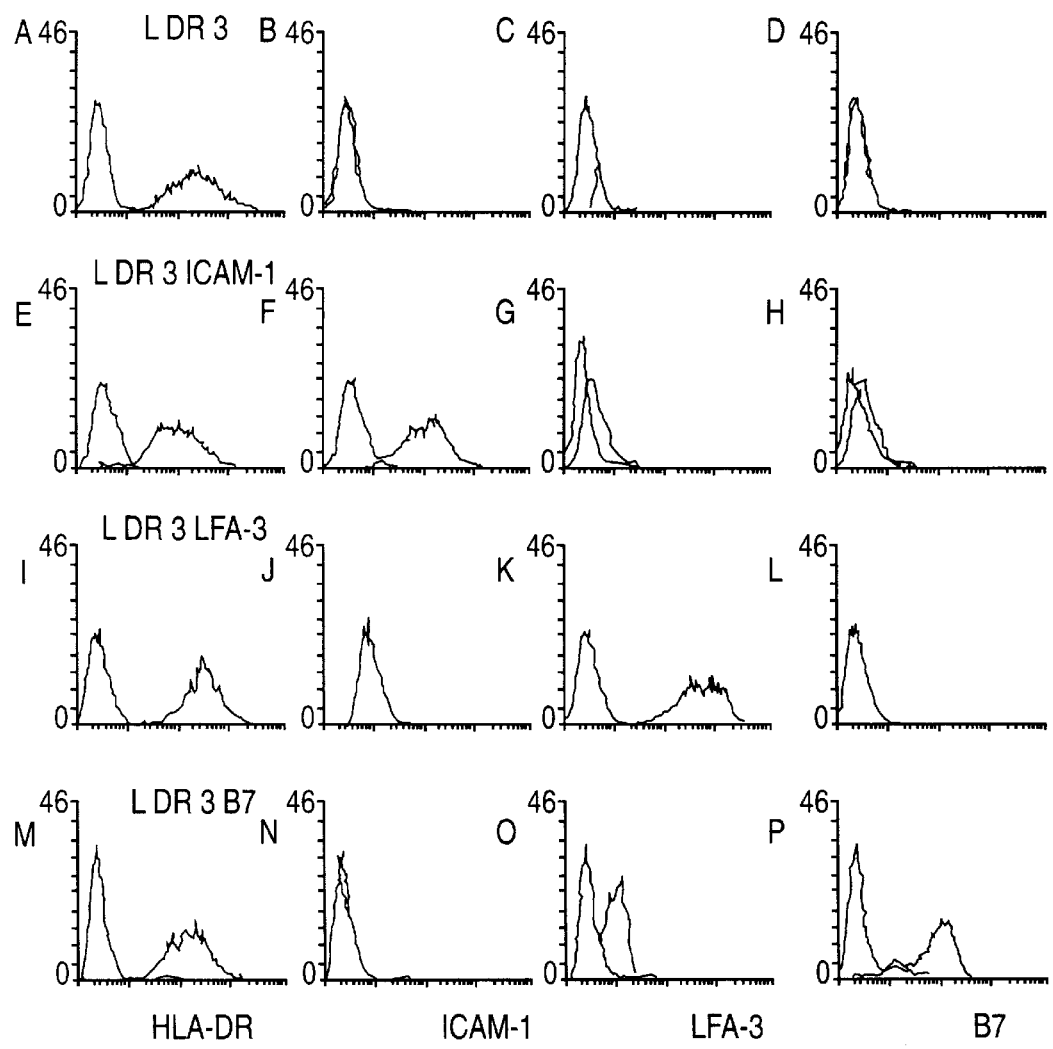
FIG. 9 shows the phenotype of L cells transfected with HLA-DR3 and ICAM-1, LFA3, or B7. Expression of class II MHC (HLA-DR), ICAM-1, LFA-3, and B7 was determined on L cells stably transfected with HLA-DR3, ICAM-2, LFA-3, or B7.

Example 12
IL-10 Inhibits Antigen Specific T Cell Proliferation when Mouse L Cells Transfected with Human HLA Molecules are used as APC The effects of IL-10 on the antigen specific proliferation of the Tetanus Toxoid (TT) specific T cell clone 827 and M. Leprae 65 kD hsp pt [2–12] specific T cell clone HY-06 were examined when mouse L cells transfected with HLA-DR3 or HLA-DR3 and ICAM-1, LFA3, or B7, as described above, were used as antigen presenting cells. The FACS profiles of the expression of HLA-DR, ICAM-1, LFA3, and B7 by the L cell transfectants are shown in FIG. 9. IL-10 had no effect on the constitutive expression of class II MHC on these cells.

Tetanus Toxin was provided by Dr. B. Bizzini (Institute Pasteur, Paris, France) and used at a final concentration of 1 μg/ml. Hsp pt [2–12] was made by a solid phased peptide synthesis methodology and checked using analytical reverse phase HPLC and amino acid and analysis. The peptides were used at a final concentration of 0.5 μg/ml.

Figure 10:
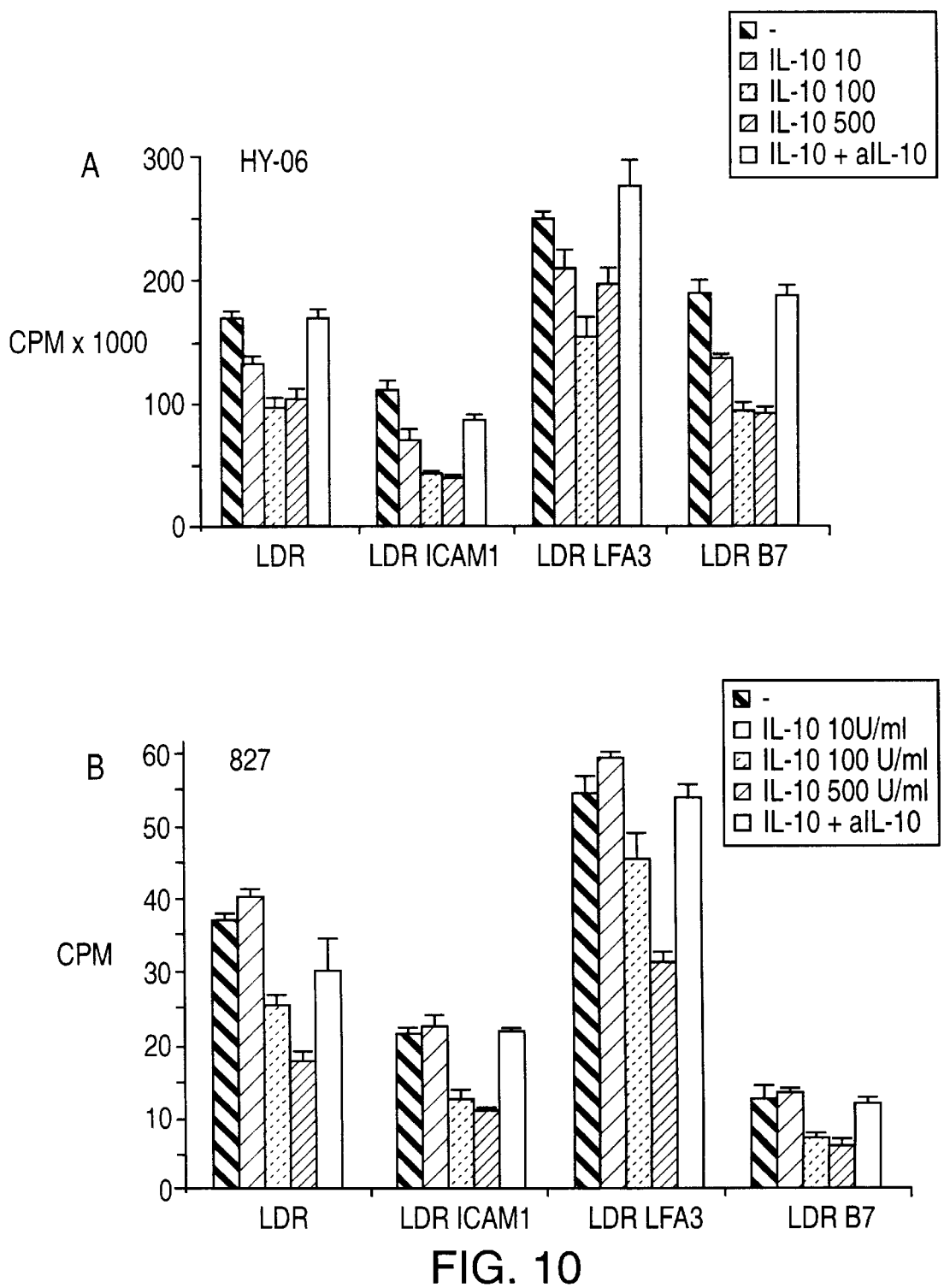
FIG. 10 has two panels, A and B. Panel A shows the effect of IL-10 on the antigen specific proliferation of T cell clone HY-06. T cell clones ($2\times10^4$ cells/well) were activated by pt [2–12] (0.5 µg/ml) or Tetanus Toxin (1 µg/ml) in the presence of increasing concentrations of IL-10 (10–500 U/ml) or in the presence of IL-10 (10–500 100 U/ml) and neutralizing mAb 19F1 (10 µg/ml) with L cell transfectants ($2\times10^4$ cells/well) as APC. Proliferative responses were determined at 72 hrs by $^3$H-TdR incorporation. Results are presented as mean ±SD of triplicate cultures. Panel B shows the effect of IL-10 on the antigen specific proliferation of T cell clone 827. T cell clones ($2\times10^4$ cells/well) were activated by pt [2–12] (0.5 µg/ml) or Tetanus Toxin (1 µg/ml) in the presence of increasing concentrations of IL-10 (10–500 U/ml) or in the presence of IL-10 (100 U/ml) and neutralizing mAb 19F1 (10 µg/ml) with L cell transfectants ($2\times10^4$ cells/well) as APC. Proliferative responses were determined at 72 hrs by $^3$H-TdR incorporation. Results are presented as mean ±SD of triplicate cultures.

The stimulation of T cell clones 827 and HY-06, proliferation assays and cytokine measurements were performed as described above. IL-10 inhibited the antigen specific proliferation of HY-06 (FIG. 10, panel A) and 827 (FIG. 10, panel B) with L cells transfected with HLA-DR3 as antigen presenting cells (APC) in a dose dependent fashion. IL-10 added at 10 U/ml had inhibitory activity and up to 30–50% inhibition of proliferation was obtained at 100 U/ml and 500 U/ml. These results were confirmed when L cells transfected with HLA-DR and ICAM-1, LFA3 or B7 were used as APC (see FIG. 10, panels A and B). The proliferative responses of T cell clones 827 and HY-06 increased when L cells cotransfected with LFA3 were used and the inhibitory effect of IL-10 was less pronounced. The inhibition of the proliferative responses of 827 and HY-06 by IL-10 was completely reversed by the neutralizing anti-IL-10 mAb 19F1, indicating the specificity of the inhibition. These results indicate that IL-10 inhibits antigen specific proliferative responses of 827 and HY-06 when HLA-DR transfected mouse L cells are used as APC.

Figure 11:
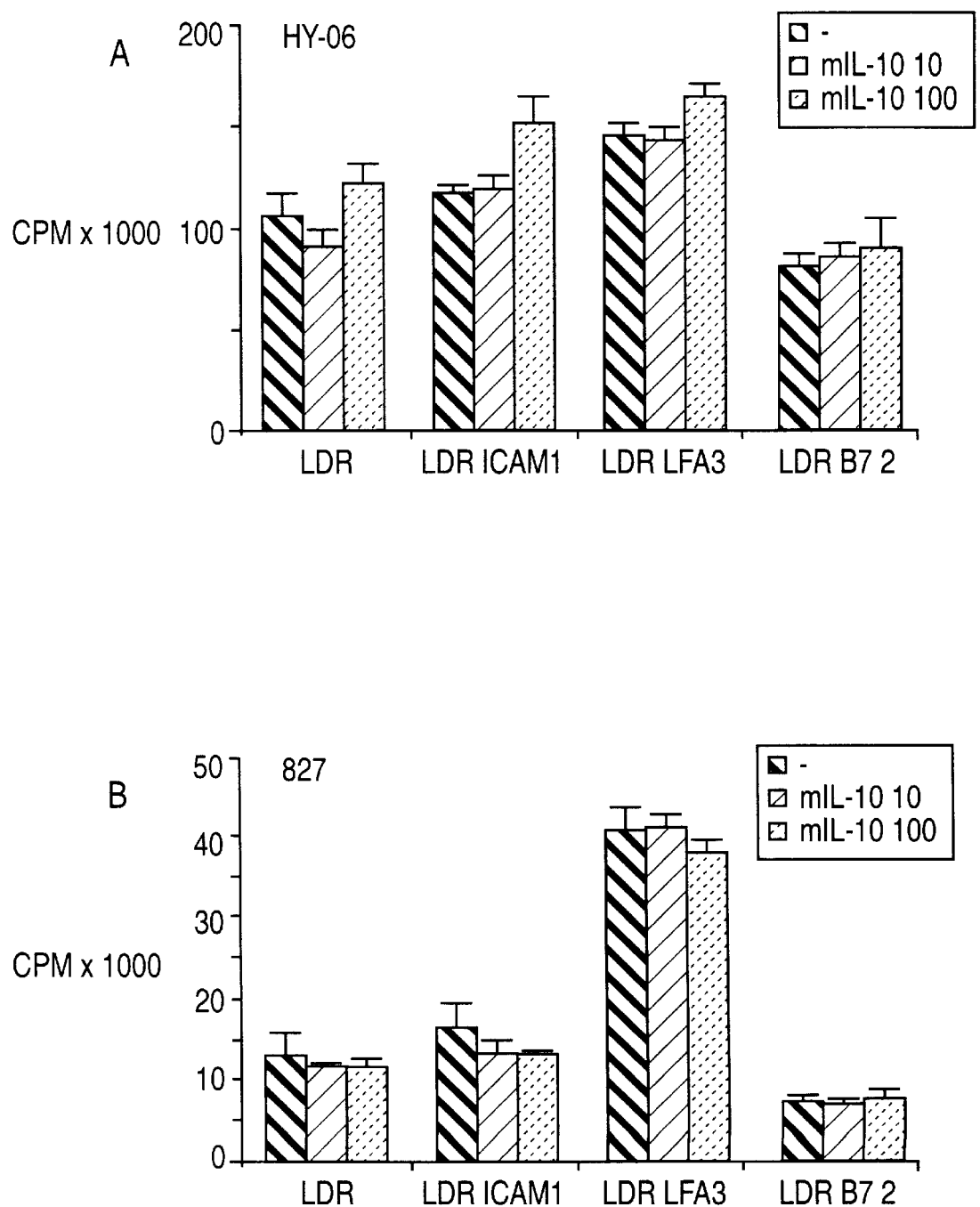
FIG. 11 has two panels, A and B. Panel A shows the effect of mouse-IL-10 on the antigen specific proliferation of T cell clones HY-06. T cell clones ($2\times10^4$ cells/well) were activated by pt [2–12] (0.5 µg/ml) or Tetanus Toxin (1 µg/ml) in the presence of increasing concentrations of mouse IL-10 (10–500 U/ml) with L cell transfectants ($2\times10^4$ cells/well) as APC. Proliferative responses were determined at 72 hrs by $^3$H-TdR incorporation. Results are presented as mean ±SD of triplicate cultures. Panel B shows the effect of mouse-IL-10 on the antigen specific proliferation of T cell clone 827. T cell clones ($2\times10^4$ cells/well) were activated by pt [2–12] (0.5 µg/ml) or Tetanus Toxin (1 µg/ml) in the presence of increasing concentrations of mouse IL-10 (10–500 U/ml) with L cell transfectants ($2\times10^4$ cells/well) as APC. Proliferative responses were determined at 72 hrs by $^3$H-Tdr incorporation. Results are presented as mean ±SD of triplicate cultures.

The inhibition of antigen specific proliferation by IL-10 was found to be at the T cell level. To determine this, T cell clones 827 and HY-06 were activated by TT and pt [2–12] in the presence of human or murine IL-10 to investigate whether IL-10 is acting on the antigen presenting L cells or directly on the T cell clones. As discussed above, human IL-10 is active on human and mouse cells, but murine IL-10 is only active on mouse cells. As shown in FIG. 11, murine IL-10 was not able to inhibit the antigen specific proliferation of 827 and HY-06 when L cells transfected with HLA-DR alone or cotransfected with ICAM-1, LFA3, or B7 were used as APC. These results indicate that IL-10 has a direct effect on the proliferation of human T cell clones.

Figure 12:
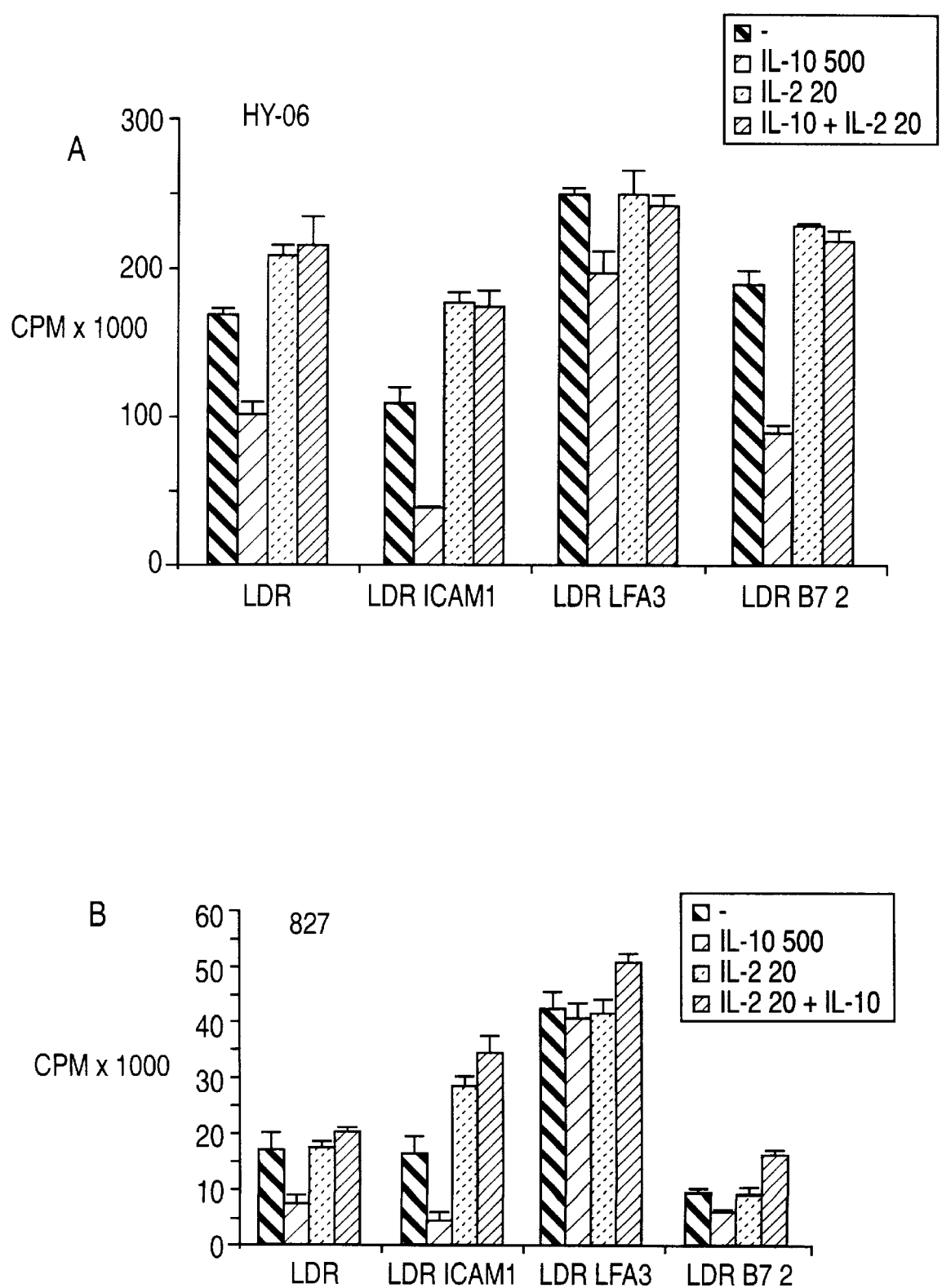
FIG. 12 has two panels, A and B. Panel A shows the effect of IL-10 on the antigen specific proliferation of T cell clone HY-06. T cell clones ($2\times10^4$ cells/well) were activated by pt [2–12] (0.5 µg/ml) or Tetanus Toxin (1 µg/ml) in the absence or presence of IL-10 (500 U/ml) and/or IL-2 (20 U/ml) with L cell transfectants ($2\times10^4$ cells/well) as APC. Proliferative responses were determined at 72 hrs by $^3$H-TdR incorporation. Results are presented as mean ±SD of triplicate cultures. Panel B shows the effect of IL-10 on the antigen specific proliferation of T cell clone 827. T cell clones ($2\times10^4$ cells/well) were activated by pt [2–12] (0.5 µg/ml) or Tetanus Toxin (1 µg/ml) in the absence or presence of IL-10 (500 U/ml) and/or IL-2 (20 U/ml) with L cell transfectants ($2\times10^4$ cells/well) as APC. Proliferative responses were determined at 72 hrs by $^3$H-TdR incorporation. Results are presented as mean ±SD of triplicate cultures.

T cell clones 827 and HY-06 were activated by TT or pt [2–12] with L cells expressing HLA-DR alone or in combination with ICAM-1, LFA3, or B7 in the presence or absence of IL-10 and IL-2 to examine whether the addition of exogenous IL-2 could reverse the inhibitory effects of IL-10. FIG. 12, panels A and B, show that low concentrations of IL-2 could reverse the inhibitory effects of IL-10 on antigen specific proliferation of T cell clones 827 and HY-06.

Figure 13:
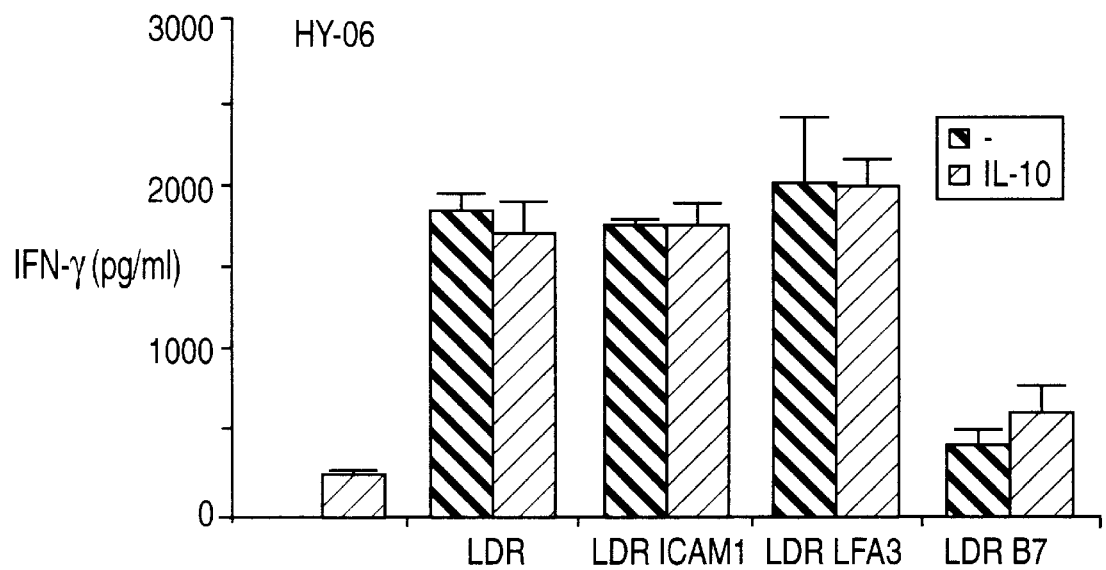
FIG. 13 shows the effect of IL-10 on the production of IFN-γ and IL-2 by T cell clone HY-06. T cell clone ($2\times10^5$ cells/well) were activated by pt [2–12] (0.5 µg/ml) in the absence or presence of IL-10 (100 U/ml) with L cell transfectants ($2\times10^4$ cells/well) as APC and production of IFN-γ and IL-2 was determined by cytokine specific ELISAs.
Figure 13:
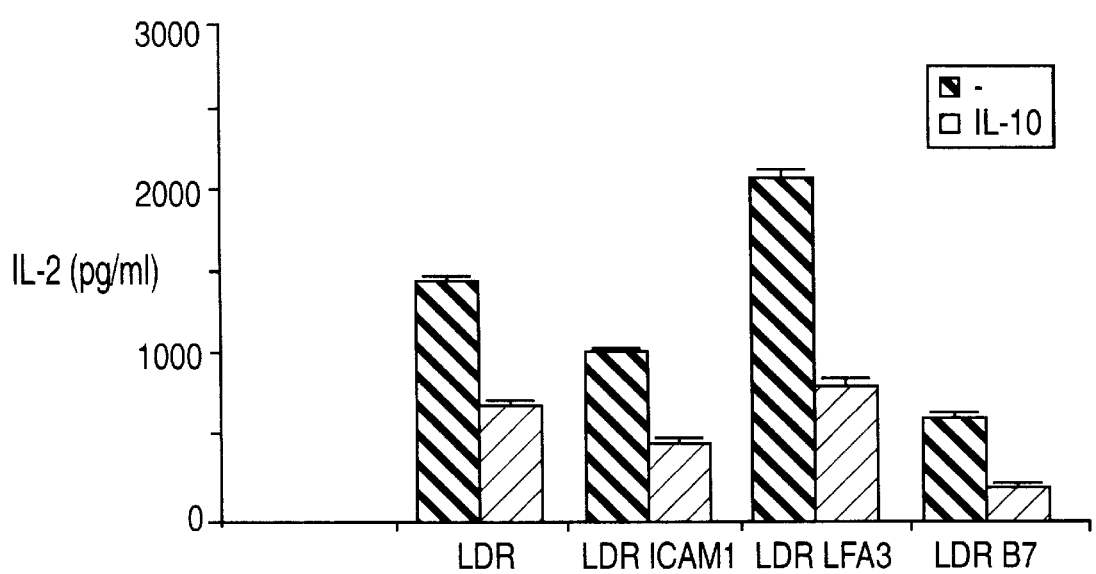

T cell clone HY-06 was activated by pt [2–12] with L cells expressing HLA-DR3 alone or in combination with ICAM-1, LFA3, or B7 in the presence or absence of IL-10 and the production of IL-2 and IFN-γ was determined in the culture supernatants harvested at 24 hours. FIG. 13, panels A and B, shows that IL-10 inhibited the production of IL-2, but not of IFN-γ by T cell clone HY-06 following antigen specific activation. Taken together these results indicate that IL-10 inhibits antigen specific T cell proliferation by a specific inhibition in the production of IL-2.

Example 13
Effect of IL-10 on B Cell Lymphocytic Leukemia Cells

Recent studies have established that IL-10 induces proliferation and most notably differentiation of normal human B lymphocytes. The effects of IL-10 on the growth and the survival of B-CLL cells activated or not via their antigen receptor were studied. IL-10 reduced by 30–90% the DNA synthesis of 12 B-CLL samples stimulated by anti-IgM antibodies or particles of Staphylococcus aureus strain Cowan I. In addition, IL-10 was found to inhibit by 54–84% the spontaneous [$^3$H]-TdR incorporation observed in 3 on 12 B-CLL samples. In contrast to IL-4, IL-10 did not inhibit the [$^3$H]-TdR uptake obtained in response to IL-2 alone. However, it inhibited the IL-2 mediated DNA synthesis of anti-IgM activated B-CLL cells. Furthermore, IL-10 decreased the viable cell recovery of all the five B-CLL samples tested which did not spontaneously proliferate in vitro. The decrease of viable cell recovery followed IL-10 induced apoptosis of B-CLL cells. The apoptosis mediated by IL-10 was specific as it was reverted by a neutralizing anti-IL-10 antibody. It was not reduced to one particular subpopulation of the leukemic clone. Addition of IL-2 was found to prevent the IL-10 mediated apoptosis of B-CLL cells.

Thus, IL-10 inhibits the DNA synthesis and most notably the survival of B-CLL cells, findings which call for considering IL-10 in the immunotherapy of chemoresistant B cell chronic lymphocytic leukemias.

The production of antibodies of high affinity and high specificity is the result of multiple genetic alterations of the B lymphocyte immunoglobulin loci. These modifications happen at different stages of the B lymphocyte history which occurs both in the bone marrow and in the secondary lymphoid organs. These various events are sometimes accompanied by abnormal B cell development resulting in multiple types of leukemias, one of the most common ones in western countries being the chronic lymphocytic leukemia.

The B lymphocytes involved in this disease constantly express CD5 antigen, surface IgM with or without IgD, CD23, and the bcl-2 protooncogene. A major fraction of the neoplastic population is frozen in the $G_0$ phase of the cell cycle. For all these characteristics and on the basis of morphological analysis, B-CLL cells have been considered to represent the neoplastic counterpart of the CD5 resting B lymphocytes or the mantle zone like-B lymphocytes. However, when considering the responsiveness to cytokines, discrepancies between B-CLL cells and normal B cells have been observed in vitro. Indeed, while normal B cells need a first external activation signal to proliferate in response to IL-2, about 50% of B-CLL cells show a spontaneous proliferative response to IL-2. Furthermore, IL-4 not only lacks growth-promoting activity, but displays a potent inhibitory activity on B-CLL proliferation observed upon surface Ig triggering with or without IL-2.

Recently, IL-10 has been found to enhance both the proliferation and the differentiation of normal B cells stimulated by crosslinking of either their surface Igs or their CD40 antigens. In contrast, the present study demonstrates that IL-10 inhibits DNA synthesis and survival of B-CLL cells activated or not through their antigen receptors.

Reagents

Insolubilized anti-IgM antibodies were purchased from Bio-Rad Laboratories (Richmond, Calif.) and were used at the final concentration of 10 μg/ml. Formalinized particles of Staphylococcus aureus strain Cowan I (SAC) were purchased as Pansorbin from Calbiochem-Behring Corporation (La Jolla, Calif.) and were used at the final concentration of 0.005% (v/v).

Antibodies

Monoclonal and polyclonal antibodies used for the phenotyping of the leukemic B cell preparations were purchased from the following manufacturers: Becton-Dickinson Monoclonal Center (Mountain View, Calif.): fluorescein-conjugated anti-CD5 (Leu 1), anti-CD19 (Leu 12), anti-CD20 (Leu 16), anti-CD14 (Leu M3), anti-CD10 (Calla), anti-HLA DQ and anti-HLA DR monoclonal antibodies; Immunotech (Marseille, France): fluorescein-conjugated anti-CD3 (IOT3) and anti-CD2 (IOT11) monoclonal antibodies; Dako (Glostrup, Denmark): FITC-conjugated F(ab)'$_2$ fragments of goat anti-human IgM, IgD, IgA, and IgG antibodies; and Kallestad (Austin, Tex.): FITC-conjugated F(ab)'$_2$ fragments of goat anti-human lambda or kappa light chains antibodies. The anti-CD23 Mab 25 and the neutralizing anti-IL-10 purified antibody were produced in the laboratory as described in Bonnefoy, et al. (1987) *J. Immunol.* 138:2970–2978 and Burdin, et al. (1993) *J. Exp. Med.* 177:295–304. Three μg/ml of anti-IL-10 antibody were determined to totally inhibit the effect of 10 ng/ml of IL-10 in an inhibition assay of IFN-γ production. A polyclonal anti-C4 antibody, produced and purified in the same conditions as the anti-IL-10, was used as unrelated control antibody.

Flow Cytometric Analysis

Cell surface staining was performed as described by Defrance, et al. (1987) *J. Immunol.* 139:1135–1141, and samples were analyzed with a FACScan® (Becton-Dickinson, Sunnyvale, Calif.). Propidium iodide (2 μg/ml) was added in each sample prior to flow cytometric analysis in order to gate-out dead cells. The negative control was performed with an isotype-matched unrelated monoclonal antibody. Apoptosis was determined by measurement of the incorporation of DNA-binding fluorophores Hoechst 33342 and propidium iodide. Cells were incubated 5 min with 10 μM Hoechst 33342 and 32 μM propidium iodide immediately before analysis with a double laser equiped FACStar-plus®. Analyses permitted delineation into three different populations. Permeabilisation of cell membranes allowed dead cell to incorporate propidium iodide; the DNA fragmentation induceed an increase of Hoechst binding; finally, viable cells did not incorporate propidium iodide and Hoechst. The validity of this method was confirmed by fluorescent microscopy on the cells sorted from each population.

Factors

Purified recombinant IL-2 (3×10$^6$ U/mg, Amgen Biologicals, Thousand Oaks, Calif.) and IL-4 (1×10$^7$ U/mg, Schering-Plough Research Institute, Kenilworth, N.J.) were routinely used at the final concentration of 20 U/ml and 100 U/ml, respectively. Recombinant highly purified IL-10 from CHO transfected cells, was obtained from Schering-Plough Research Institute and routinely used at a final concentration of 100 ng/ml.

Patients

Pathological samples were provided by Dr. A. Bussel (Hopital Saint-Louis, Paris), Dr. J. F. Rossi (Institut du Cancer-Val d'Aurelle, Montpellier), and Dr. P. Bryon (Hopital Edouard Herriot, Lyon). This study included 12 patients, 6 women and 6 men, aged 26 to 85, having the clinical and immunophenotype criteria for B-CLL. See Fluckiger, et al. (1992) *Blood* 80:3173–3181. Six patients were classified as early clinical stages (Binet's stage A, Rai's stages I and II), 6 patients were classified as advanced clinical stages (Binet's stages B and C, Rai's stages III and IV). See, e.g., Binet, et al. (1977) *Cancer* 40:855–864 and Rai, et al. (1975) *Blood* 46:219–234. Patient BAR was treated by corticoids and patient FLA was treated by chemotherapy at the time of the study. All other patients had not received any chemotherapy in the 3 months preceding this study. Ten samples were obtained from blood and 2 were obtained from spleen (POT and SOU).

Purification of B-CLL Cells

Mononuclear cells were separated by standard Ficoll/Hypaque gradient method and were next submitted to E rosetting with sheep red blood cells. Non rosetting cells (E$^-$fraction) were labeled with anti-T cell (anti-CD2 and anti-CD3 from Aster Laboratories, La Gaude, France) and anti-monocyte (anti-CD14 from Immunotech) monoclonal antibodies and subsequently incubated with magnetic beads coated with anti-mouse IgG antibodies (Dynal, Oslo, Norway). Residual non B cells were removed by applying a magnetic field for 5 min.

B Cell Cultures

Purified leukemic B cells were cultured in Iscove's medium (Flow Laboratories, Irvine, Calif.) enriched with 50 μg/ml human transferrin (Sigma Chemical, St Louis, Mo.), 0.5% bovine serum albumin (Sigma), 5 μg/ml bovine insulin (Sigma), 5% selected heat inactivated fetal calf serum, 100 U/ml penicillin, 100 μg/ml streptomycin (all from Flow Laboratories) and $10^{-5}$ M of β mercaptoethanol (Sigma). $10^5$ B-CLL cells were cultured in round-bottomed microtiter trays under a final volume of 100 μl. Polyclonal B cell activators and cytokines were added at the onset of the culture. DNA synthesis was determined by pulsing cells with tritiated thymidine [$^3$H]-TdR for the final 16 h of the culture period. Due to the heterogeneity of the responses of the B-CLL samples, DNA synthesis was assessed at three different time points (4, 5, and 6 days after onset of the culture). The results presented correspond to the time point which provided the maximal stimulation indices. Each culture point was performed in triplicate.

IL-10 Inhibits the DNA Synthesis of B-CLL Cells Activated via their Antigen Receptors In order to examine the response of B-CLL cells to IL-10, twelve B-CLL specimens were cultured with SAC or anti-IgM beads without or with IL-10. Table 3 shows that the DNA synthesis induced by anti-Ig reagents was very heterogeneous depending on the B-CLL sample. According to Wilcoxon rank tests, IL-10 significantly reduced the SAC (p 0.0022) or anti-IgM (p 0.0051) induced proliferative response, with a mean inhibitory effect of 70%. One of the 12 B-CLL samples (POT) was not inhibited when stimulated by SAC, however, its anti-IgM induced DNA synthesis was inhibited by IL-10. The inhibitory effects of IL-10 on B-CLL cells were compared to those of IL-4 (see Table 3). After SAC activation, both IL-10 and IL-4 displayed similar inhibitory effects on B-CLL DNA synthesis on 8 out of 12 B-CLL samples. After anti-IgM stimulation, IL-10 inhibited the DNA synthesis of 10 on 12 B-CLL samples while IL-4 inhibited only 6 on 12 samples.

TABLE 3

IL-10 inhibits the anti-IgM or SAC induced DNA synthesis of B-CLL cells

| B-CLL | [$^3$H]TdR uptake (cpm × $10^{-3}$) | | | | | |
|---|---|---|---|---|---|---|
| | SAC | | | anti-IgM | | |
| | no CK | IL-10 | IL-4 | no CK | IL-10 | IL-4 |
| BAE | 44.1 | 5.5 | 2.9 | 7.4 | 2.1 | 1.2 |
| BAI | 0.7 | 0.3 | 0.9 | 65.4 | 17.8 | 63.9 |
| BAR | 77.1 | 7.9 | 19.2 | 2.6 | 0.4 | 1.3 |
| BOL | 49.7 | 25.1 | 20.7 | 1.4 | 0.5 | 0.4 |
| FLA | 1.4 | 1.3 | 1.5 | 18.3 | 1.4 | 28.7 |
| GER | 1.9 | 0.2 | 0.07 | 2.1 | 0.09 | 0.09 |
| LES | 3.2 | 0.7 | 1.1 | 0.8 | 0.3 | 0.3 |
| MAG | 17.6 | 0.7 | 0.9 | 0.3 | 0.3 | 0.3 |
| PIG | 0.8 | 0.05 | 0.1 | 22.8 | 2.9 | 2.6 |
| PON | 4.9 | 0.5 | 2.5 | 0.2 | 0.2 | 0.2 |
| POT | 53.1 | 48.7 | 27.8 | 2.6 | 0.5 | 1.7 |
| SQU | 0.2 | 0.1 | 0.3 | 4.3 | 1.8 | 4.2 |

1 × $10^5$ B-CLL cells were costimulated with either SAC or anti-IgM and without or with IL-10 or IL-4. [$^3$H]TdR uptake was measured at day 3, 4, and 5. The values displayed were those from the day of the peak response to the activator. Standard deviations never exceeded 10% of the mean value of the triplicate determination.

Figure 14:
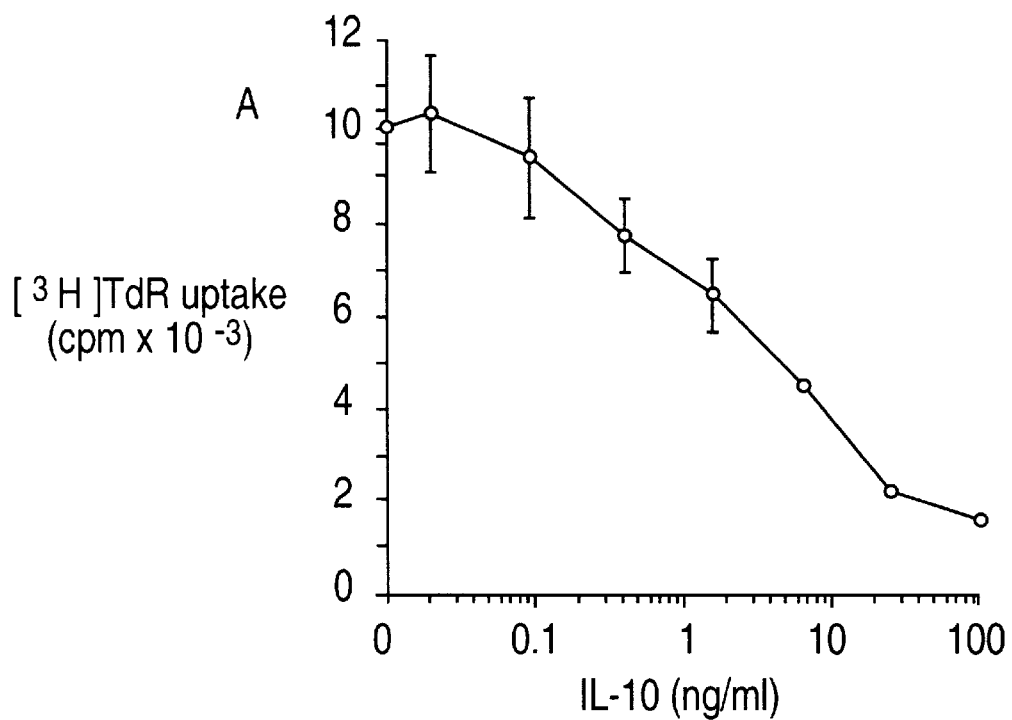
FIG. 14 shows that the inhibitory effect of IL-10 on the anti-IgM induced DNA synthesis of B-CLL cells is dose dependent and persistent. $1\times10^5$ cells of the leukemic sample FLA were cultured together with insolubilized anti- IgM antibodies (10 μg/ml) and without or with IL-10. Panel A: serial dilutions of IL-10 were used and [$^3$H]-TdR uptake was assessed at day 4. Panel B: 100 ng/ml of IL-10 was used and [$^3$H]-TdR uptake was measured after 3, 4, and 5 days of culture. Results are expressed as mean ±SD of triplicate determination. Two experiments performed with other B-CLL samples yielded similar results.
Figure 14:
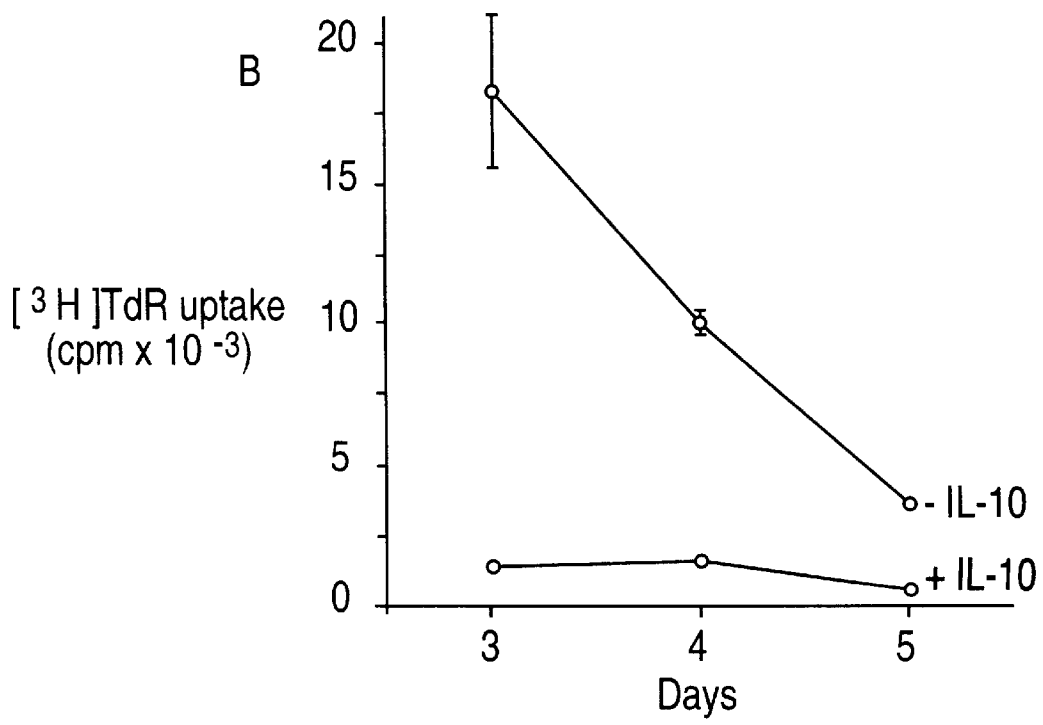

As shown on FIG. 14, panel A (representative of 3 independent experiments), the effect of IL-10 was dose dependent. The 50% inhibition was obtained with 1–3 ng/ml and maximal inhibition with 10–100 ng/ml of IL-10. It did not vary with time since IL-10 never enhanced [$^3$H]-TdR uptake of B-CLL cells in pulses performed daily on cultures ranging from day 3 to day 5 (FIG. 14, panel B).

IL-10 Inhibits Spontaneous DNA Synthesis of B-CLL Cells

Figure 15:
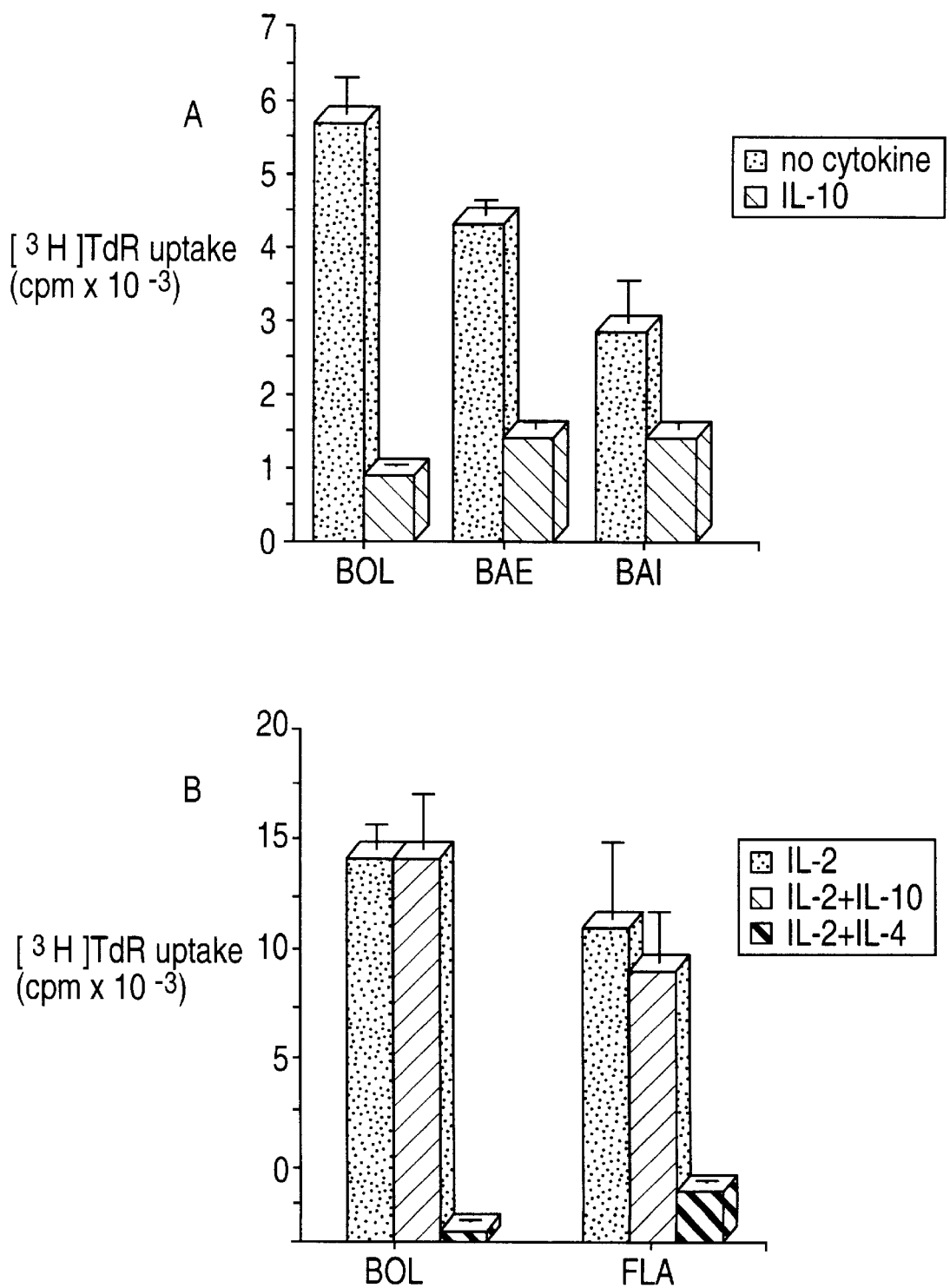
FIG. 15 shows that IL-10 inhibits spontaneous and IL-2 dependent DNA synthesis of B-CLL cells. $1 \times 10^5$ B-CLL cells were cultured for 3 days in complete medium without or with the following cytokines: (Panel A) IL-10 (100 ng/ml), (Panel B) IL-2 (20 U/ml) alone or together with IL-10 (100 ng/ml) or IL-4 (100 U/ml). DNA synthesis was determined by [$^3$H]-TdR uptake assay. Results are expressed as mean ±SD of triplicate determination.

The twelve B-CLL specimens were then incubated during 3 days in complete medium with or without IL-10. Three B-CLL samples (FIG. 15, panel A) were found to spontaneously incorporate significant amounts of [$^3$H]-TdR (2800 to 5700 cpm) after three days of culture, and in all three cases, IL-10 significantly reduced this response (54 to 84% inhibition). The inhibitory activity of IL-10 was dose dependent, with efficient concentrations comparable to those described. The IL-10 dependent inhibition of [$^3$H]TdR uptake was observed from day 2 to day 7. The poor [$^3$H]TdR uptake observed in the eight other B-CLL cases (1000 cpm) was not significantly affected by IL-10. Then, whether IL-10, like IL-4, could alter the IL-2 dependent DNA synthesis of B-CLL cells was tested. Two of the 6 B-CLL samples tested proliferated in response to IL-2 alone. In contrast to IL-4, IL-10 did not inhibit the spontaneous response to IL-2 (FIG. 15, panel B).

Trypan blue dye exclusion assays were performed on five B-CLL samples cultured for four days and which poorly incorporated [$^3$H]TdR in absence of exogenous activator. Table 4 demonstrates that the viable B-CLL cell recovery was reduced after exposure to IL-10. The loss of viable cells in response to IL-10 was particularly striking for samples GER, LES, and PON. In contrast, IL-2 had no effect or slightly increased cell counts of the 2 B-CLL samples which spontaneously proliferated in response to IL-2 (PON and FLA). Moreover, addition of IL-2 prevented the decrease of cell number induced by IL-10.

TABLE 4

IL-10 decreases the recovery of viable unstimulated B-CLL cells

| B-CLL | Viable cell recovery (× $10^{-5}$) | | | |
|---|---|---|---|---|
| | no cytokine | IL-10 | IL-2 | IL-10 + IL-2 |
| BAR | 1.6 | 0.8 | 1.9 | 2.3 |
| GER | 1.3 | 0.5 | 1.8 | 1.0 |
| LES | 1.7 | 0.5 | 2.8 | 2.1 |
| FLA | 3.7 | 1.6 | 5.1 | 3.3 |
| PON | 2.9 | 0.8 | 4.8 | 3.7 |

$5 \times 10^5$ (FLA and PON) or $2.5 \times 10^5$ (LES, BAR and GER) B-CLL cells were seeded in supplemented Iscove medium without or with IL-10 (100 ng/ml) or IL-2 (20 U/ml) or combination of IL-10 and IL-2. Viable cell recovery was determined by Trypan blue dye exclusion after 4 days of incubation.

IL-10 Enhances the Apoptosis of B-CLL Cells

Figure 16:
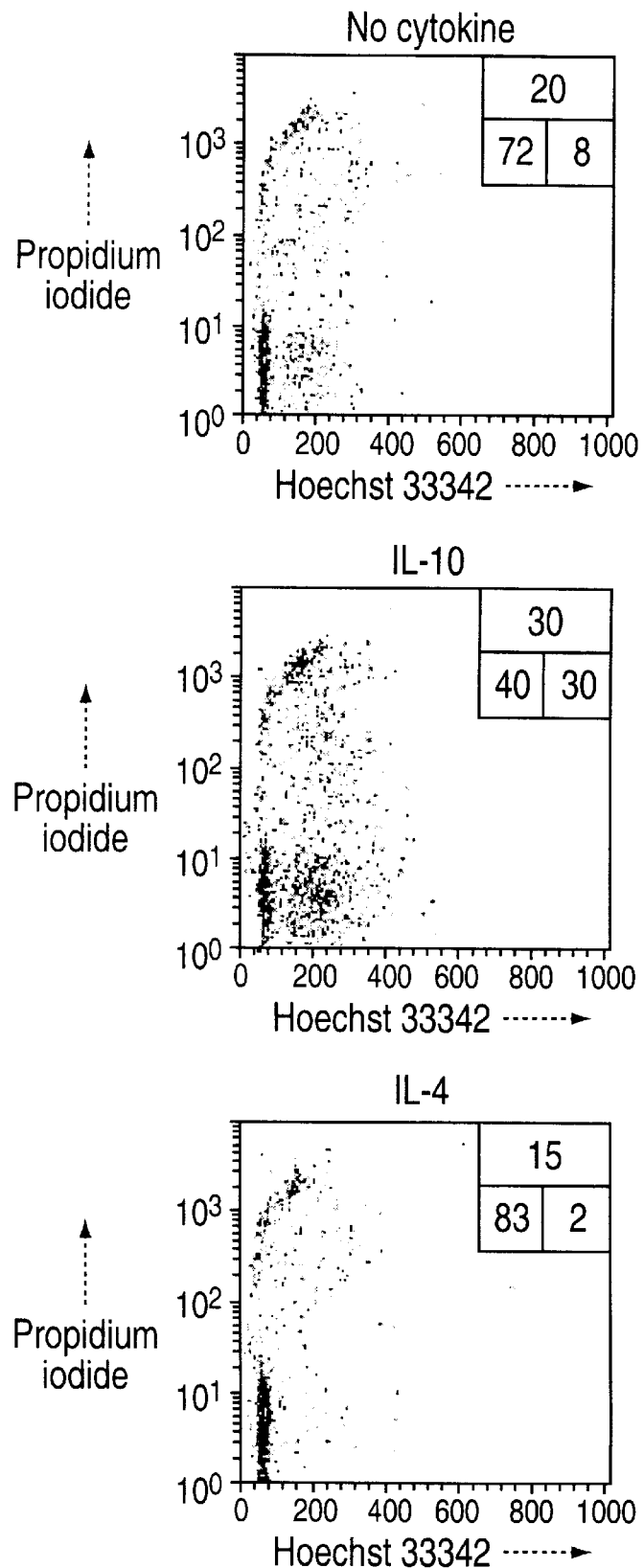
FIG. 16 shows that IL-10 increases the spontaneous apoptosis of B-CLL cells. $5 \times 10^5$ B-CLL cells were cultured without or with IL-10 (100 ng/ml) or IL-4 (100 U/ml). After 24 h, cells were incubated 5 min with Hoechst 33342 (10 μM) and propidium iodide (32 μM). Discrimination of necrotic and apoptotic cells was performed by multiparametric flow cytometry. Ordinates: propidium iodide; abscissa: Hoechst 33342. Numbers indicate the percentage of positive cells in the three populations. The upper dot plot corresponds to necrotic cells, the lower left to viable cells and the lower right to apoptotic cells.

To further document the deleterious effect of IL-10 on cell viability, it was tested whether B-CLL cells, exposed to IL-10, were dying from necrosis or apoptosis. Thus, after a 24 hour incubation with IL-10 or IL-4, B-CLL cells were incubated with Hoechst 33342 and propidium iodide to discriminate necrotic cells from apoptotic cells by flow cytometry. Cells incorporating only Hoechst 33342 were undergoing apoptosis whereas those incorporating propidium iodide and Hoechst 33342 were undergoing necrosis. Viable cells incorporated neither of these dyes. As shown by FACS analysis (FIG. 16), IL-10 increased the spontaneous apoptosis of the FLA B-CLL cells from 8 to 30%. This was confirmed by microscopic examination of Giemsa stained smears. On the 5 B-CLL samples tested, IL-10 enhanced by two-three fold the percentage of cells undergoing apoptosis while IL-4 inhibited it in 3 cases on 4 (Table 5).

TABLE 5

IL-2 prevents IL-10 induced apoptosis of B-CLL cells
% of apoptotic cells

| B-CLL | no cytokine | IL-4 | IL-10 | IL-2 | IL-10 + IL-2 | anti-IgM | anti-IgM + IL-10 |
|---|---|---|---|---|---|---|---|
| PON | 8 | 2 | 13 | 6 | 3 | 3 | 8 |
| FLA | 9 | 2 | 25 | 7 | 4 | 3 | 11 |
| PIG | 6 | 2 | 15 | 4 | 8 | ND | ND |
| MAG | 8 | 8 | 14 | 6 | 11 | ND | ND |
| BAR | 3 | 2 | 5 | 2 | 1 | 2 | 6 |

$5 \times 10^5$ B-CLL cells were cultured with or without IL-10 (100 ng/ml) or IL-2 (20 U/ml) or IL-4 (100 U/ml) or anti-IgM antibodies (10 µg/ml) or combination of IL-2 and IL-10 or anti-IgM and IL-10. After 24 hours, B-CLL cells were incubated with Hoechst 33342 (10 µM) and propidium iodide (32 µM) during 5 min before analysis on FACStar ®.

Figure 17:
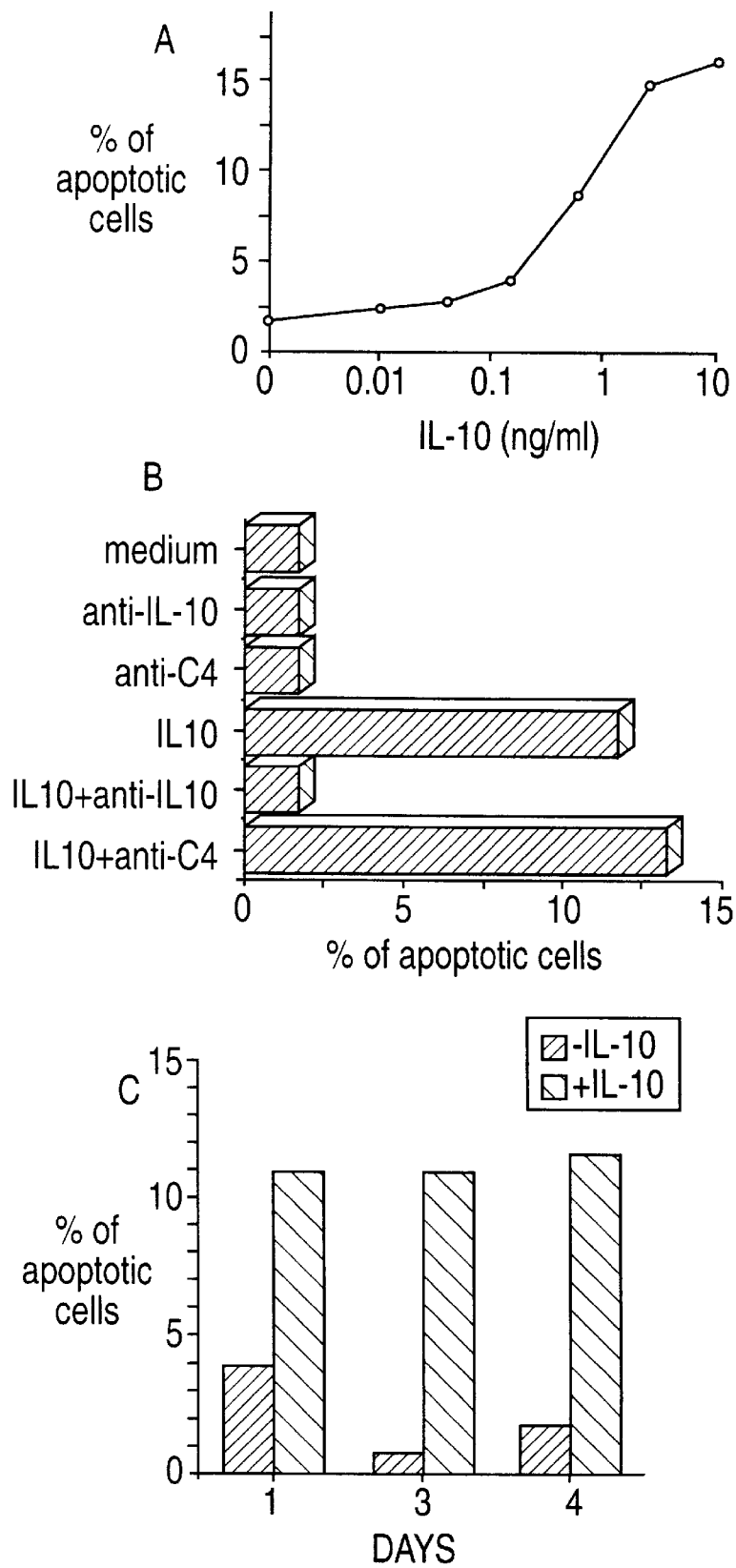
FIG. 17 shows that the effect of IL-10 on B-CLL apoptosis is dose dependent and specific. $5 \times 10^5$ B-CLL cells were cultured: (Panel A) for 24 h without or with serial dilutions of IL-10; (Panel B) for 24 h with IL-10 (10 ng/ml) or anti-IL-10 Ab (3 μg/ml) or anti-C4 Ab (3 μg/ml) as a control, or combination of IL-10 and anti-IL-10 Ab or IL-10 and anti-C4 Ab; (Panel C) for various periods of time, without or with IL-10 (10 ng/ml). The proportion of apoptotic cells was determined by FACS analysis after staining with Hoechst 33342 and propidium iodide.

IL-10 promoted the B-CLL apoptosis in a dose dependent manner, 50% of the maximal effect being obtained with 0.6 ng/ml of IL-10 with a plateau at 3 ng/ml of IL-10 (FIG. 17, panel A). The induction of B-CLL cell apoptosis was specific to IL-10 as a neutralizing anti-IL-10 purified antibody reverted it (FIG. 17, panel B). Similarly, the decrease in cell number observed after 4 days of culture with IL-10 was also reverted by the addition of the anti-IL-10 antibody.

Figure 18:
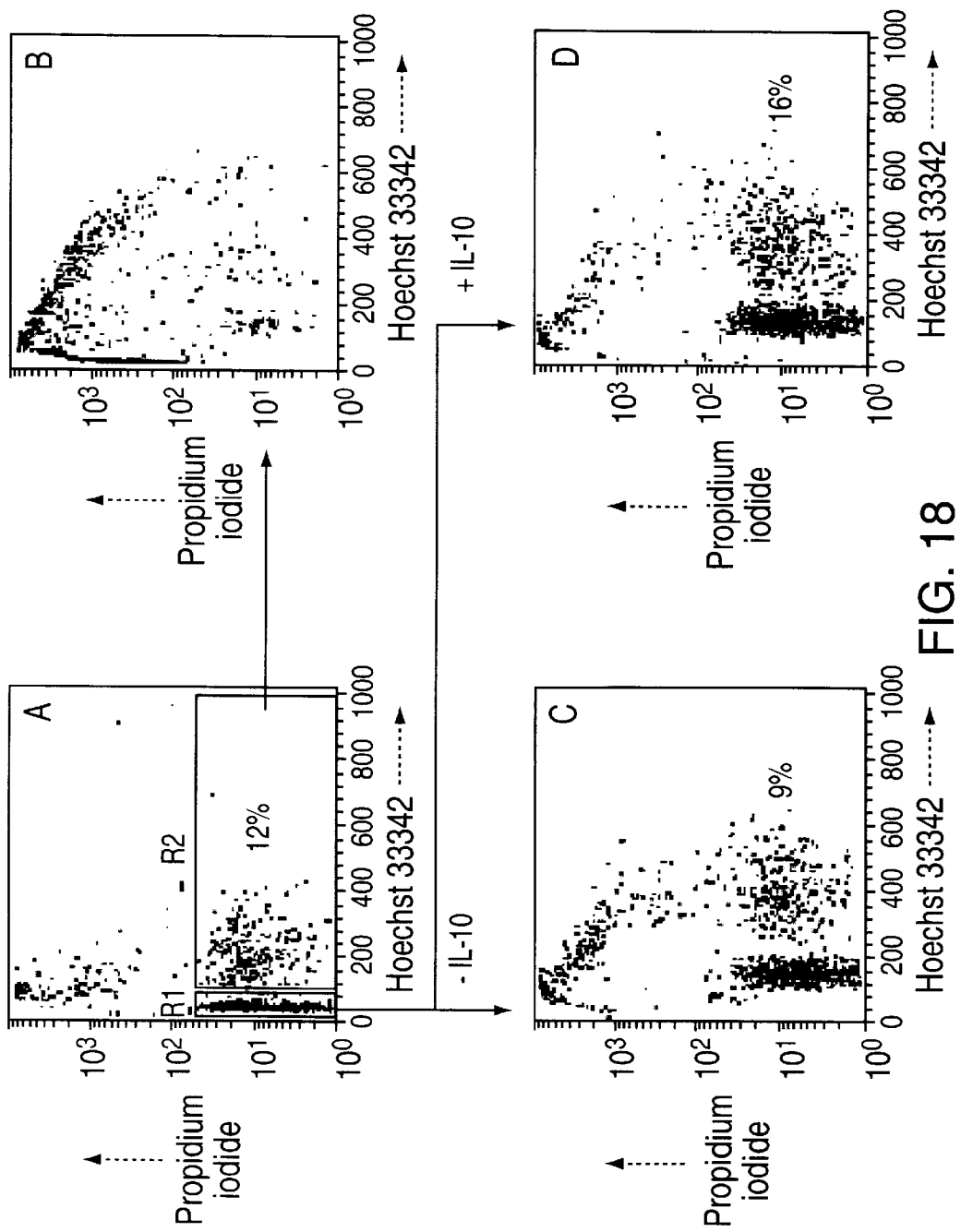
FIG. 18 shows that IL-10 progressively induces apoptosis of B-CLL cells. $10^6$ B-CLL cells were cultured without or with IL-10. After 2 days, they were stained with Hoechst 33342 and propidium iodide and analysed by FACStar-plus®. Viable (R1) and apoptotic (R2) cells from B-CLL sample PON cultured with IL-10 (Panel A) were sorted. Viable cells were recultured without (Panel C) or with (Panel D) IL-10 and apoptotic cells were incubated in medium only (Panel B). After 24 h, a second staining with Hoechst 33342 and propidium iodide was performed on the three populations.

The percentage of apoptotic cells observed in response to IL-10 appeared to be stable when tested daily over a 4 day culture period (FIG. 17, panel C). As apoptotic cells disintegrated in culture, this suggested that IL-10 progressively turned on the apoptosis of most B-CLL cells rather than recruited a small subpopulation. To test this hypothesis, B-CLL cells, cultured for 48 h with IL-10, were stained with Hoechst 33342 and propidium iodide (FIG. 18, panel A). Viable cells were sorted and recultured for 24 h without or with IL-10. As shown in FIG. 18, the spontaneous apoptosis of IL-10 preincubated viable cells (9%, FIG. 18, panel C) was enhanced by readdition of IL-10, to reach 16% (FIG. 18, panel D). Furthermore, the sorted IL-10 induced apoptotic cells were found to incorporate propidium iodide following reculture in complete medium without IL-10 (FIG. 18, panel B). This indicates further loss of membrane integrity, most likely before cellular disintegration.

IL-2, as previously described, did not significantly modify the spontaneous apoptosis of B-CLL cells (Table 5). Consistent with the previous observation that IL-10 did not inhibit the IL-2 dependent [$^3$H]TdR uptake (FIG. 15, panel B), combination of IL-2 with IL-10 resulted in a decrease of the IL-10 induced apoptosis. Moreover, in 2 cases on 5 (PON and FLA), the level of apoptosis observed in response to the combination of IL-10 and IL-2 was lower than the level of spontaneous apoptosis. Anti-IgM activation decreased the relative number of B-CLL cells undergoing apoptosis. IL-10 induced anti-IgM activated B-CLL cells to undergo apoptosis, thus explaining the initial inhibition of B-CLL DNA synthesis.

Taken together, these results demonstrate that IL-10 decreases the survival of B-CLL cells by inducing their apoptosis.

As IL-10 was shown to induce the proliferation and differentiation of normal B lymphocytes, it was investigated here whether it would also affect B-CLL cells.

An important finding of the present study is the observation that IL-10 can decrease the survival of B-CLL cells in culture through induction of apoptosis. This phenomenon appeared to be a continuous process where IL-10 progressively induced cultured cells into successive steps towards death. This was initially monitored by the exclusive incorporation of Hoechst 33342, indicating chromatin condensation and DNA fragmentation. Then, as shown by sorting experiments, incorporation of propidium iodide was observed, which indicated significant membrane alteration, corresponding to a late degeneration by in vitro "secondary necrosis". These alterations resulted in a decrease of the number of viable cells in culture which could in some B-CLL cases be very striking. Indeed, virtually all B-CLL cells disappeared from the cultures after five days thus contrasting with the well known prolonged in vitro survival of these cells. It was not clear why some cells of a given leukemic clone were entering into apoptosis early in the culture while others did it late. It could possibly be related to the age of the B-CLL cells at the time of their isolation from the patient. As noted earlier with ionomycin or glucocorticoids induced apoptosis of B-CLL cells, there was a variability in the amount of IL-10 induced cell death in different B-CLL samples which was not related to a particular phenotype. Nevertheless, all B-CLL cells tested were found to enter apoptosis in response to IL-10 thus indicating the constitutive expression of functional receptors on these cells and a homogeneity in response. This is at variance with IL-2 which spontaneously acts on half of the samples. Interestingly, IL-2 was however able to totally overcome the apoptotic effects of IL-10. This was observed not only on cells which spontaneously synthesized DNA in response to IL-2, but also on samples which failed to do so. This is best explained by the capacity of IL-10 to upregulate the expression of high affinity IL-2 receptors on B-CLL cells. These IL-2 receptors will then be available to transmit a survival signal to the B-CLL cells as was shown earlier with ionomycin treated normal B lymphocytes. This further indicates that the survival signal provided by IL-2 prevails over the apoptotic signals of IL-10. In contrast to IL-2, anti-IgM antibodies were not able to counteract the apoptotic effects of IL-10. Indeed, the apoptosis of B-CLL cells observed in the presence of both IL-10 and anti-IgM may in fact explain the inhibitory effects of IL-10 on the DNA synthesis induced following antigen receptor crosslinking.

The IL-10 induced inhibition of viability observed with B-CLL cells contrasts with the stimulation of viability observed on resting normal murine B cells. Several reasons may account for this discrepancy, the most likely being the neoplastic status of the B-CLL cells. Accordingly, IL-10 was not found to increase the spontaneous apoptosis of normal human tonsillar B cells.

Again, this contrasts with the stimulatory effects of IL-10 on normal B lymphocytes activated through their antigen receptors. Such a difference in the proliferative response of normal and leukemic B cells was observed previously with IL-4. It had earlier been ascribed to an impairment of the antigen receptor associated signal transduction specific to the B-CLL cells, but the present study indicates a presently unexplained difference even on resting cells.

The inhibitory effect of IL-10 on B-CLL cell viability thus contrasts with the protective effects of IL-4 and IFN-γ. In fact, these two cytokines were also found to inhibit the IL-10 induced apoptosis of B-CLL cells. It should be worth studying whether the effects of IL-10 on B-CLL cells are due to an alteration of the secretion of IFN-γ or any other autocrine cytokine.

The inhibitory effects of IL-10 on B-CLL cell survival and DNA synthesis calls for considering IL-10 in the immunotherapy of chemoresistant B cell chronic lymphocytic leukemias. The direct effect of IL-10 on B-CLL cells may be further strengthened by its inhibitory effect on the production of IFN-γ. This may permit therapy to decrease the levels of serum IFN-γ which is thought to significantly contribute to the in vivo survival of B-CLL cells.

The descriptions of the foregoing embodiments of the invention have been presented for purpose of illustration and description. They are not intended to be exhaustive or to limit the invention to the precise forms disclosed, and obviously many modifications and variations are possible in light of the above teachings. The embodiments were chosen and described in order to best explain the principles of the invention to thereby enable others skilled in the art to best utilize the invention in various embodiments and with various modifications as are suited to the particular use contemplated. It is intended that the scope of the invention be defined by the claims appended hereto.

Applicants have deposited separate cultures of *E. coli* MC1061 carrying pH5C, pH15C, and pBCRF1(SRα) with the American Type Culture Collection, 10801 University Boulevard, Manassas, Va. 20110-2289, under accession numbers 68191, 68192, and 68193, respectively. These deposits were made under conditions as provided under ATCC®'s agreement for Culture Deposit for Patent Purposes, which assures that the deposit will be made available to the US Commissioner of Patents and Trademarks pursuant to 35 USC 122 and 37 CFR 1.14, and will be made available to the public upon issue of a U.S. patent, which requires that the deposit be maintained. Availability of the deposited strain is not to be construed as a license to practice the invention in contravention of the rights granted under the authority of any government in accordance with its patent laws.

All references cited herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method of reducing the growth of a tumor cell in a mammal, comprising administering a therapeutically effective amount of interleukin-10 to the mammal.

2. The method of claim 1, wherein the tumor cell is a plasmacytoma.

3. The method of claim 1, wherein the tumor cell is a leukemia.

4. The method of claim 3, wherein the tumor cell is a lymphocytic leukemia.

5. The method of claim 3, wherein the leukemia is a B cell lymphocytic leukemia.

6. The method of claim 2, wherein the interleukin-10 is a viral interleukin-10 or a human interleukin-10.

7. The method of claim 2, wherein the interleukin-10 is recombinantly produced.

8. The method of claim 7, wherein the interleukin-10 is produced using a nucleotide sequence from a plasmid deposited with the ATCC® under accession number 68191 or 68192.

9. The method of claim 1, further comprising administering a therapeutically effective dose of a second biologically active agent.

10. The method of claim 1, wherein the step of administering is carried out by intravenous delivery.

11. The method of claim 1, wherein the IL-10 induces apoptosis in the tumor cell.

12. The method of claim 1, wherein the therapeutically effective amount is between about 2.5 and about 1000 g/kg/day.

13. The method of claim 1, wherein the therapeutically effective dose is between about 700 ng/kg/day and about 16g/kg/day.

14. The method of claim 1, wherein the interleukin-10 is encapsulated in a liposome.

* * * * *